(12) United States Patent
Köhler

(10) Patent No.: US 7,049,118 B2
(45) Date of Patent: May 23, 2006

(54) REGULATION OF HUMAN SERINE-THREONINE PROTEIN KINASE

(75) Inventor: Rainer H. Köhler, Beverly, MA (US)

(73) Assignee: Bayer Healthcare AG, Leverkusen (DE)

( * ) Notice: Subject to any disclaimer, the term of this patent is extended or adjusted under 35 U.S.C. 154(b) by 254 days.

(21) Appl. No.: 10/451,375

(22) PCT Filed: Dec. 27, 2001

(86) PCT No.: PCT/EP01/15320

§ 371 (c)(1),
(2), (4) Date: Nov. 18, 2003

(87) PCT Pub. No.: WO02/053749

PCT Pub. Date: Jul. 11, 2002

(65) Prior Publication Data

US 2005/0261482 A1    Nov. 24, 2005

Related U.S. Application Data

(60) Provisional application No. 60/308,098, filed on Jul. 30, 2001, provisional application No. 60/306,468, filed on Jul. 20, 2001, provisional application No. 60/259,215, filed on Jan. 3, 2001.

(51) Int. Cl.
- *C12N 9/20* (2006.01)
- *C12N 1/20* (2006.01)
- *C12N 15/12* (2006.01)
- *C07H 21/04* (2006.01)
- *A61K 38/46* (2006.01)

(52) U.S. Cl. .................... 435/194; 435/252.3; 435/320; 435/1; 435/6; 530/350; 536/23.2

(58) Field of Classification Search ................ 435/194, 435/252.3, 320.1, 6; 530/350; 536/23.2
See application file for complete search history.

(56) References Cited

U.S. PATENT DOCUMENTS 5,962,265 A   10/1999   Norris et al.

2004/0110180 A1*  6/2004  Recipon et al. ................ 435/6

FOREIGN PATENT DOCUMENTS

| EP | 0 889 127 | 1/1999 |
|---|---|---|
| WO | WO 00/15770 | 3/2000 |
| WO | WO 00/60062 | 10/2000 |
| WO | WO 00/73469 | 12/2000 |
| WO | WO 01/38503 | 5/2001 |

OTHER PUBLICATIONS

Bossemeyer et al. (1993) Phosphotransferase and substrate binding mechanism of the cAMP-dependent protein kinase catalytic subunit from porcine heart as deduced from the 2.0 A structure of the complex with Mn2+ adenylylimidodiphosphate and inhibitor peptide PKI(5-24). EMBOJ12(3):849-59.

Hanks and Hunter (1995). The eukaryotic protein kinase superfamily: kinase (catalytic) domain structure and classification. FASEB J 9(8): 576-96.

Johnson et al. (1998) The structural basis for substrate recognition and control by protein kinases. FEBS Lett 430(1-2):1-11.

Wang et al.(2001) Isolation and characterization of cDNAs for the kinase HIPK2(1). Biochim Biophys Acta 1518(1-2):168-72.

Kim et al. (1998) Homeodomain-interacting protein kinases, a novel family of co-repressors for homeodomain transcription factors. J Biol Chem 273(40):25875-9.

Database EMBL "Online" Sep. 17, 1999 Doe Joint Genome Institut: "Homo sapiens chromosome 19 clone CTC-492K19" retrieved from EMBL, Database accession No. AC010271.7.

* cited by examiner

*Primary Examiner*—Maryam Monshipouri
(74) *Attorney, Agent, or Firm*—Banner & Witcoff, Ltd.

(57) ABSTRACT

Reagents that regulate human serine-threonine protein kinase and reagents which bind to human serine-threonine protein kinase gene products can play a role in preventing, ameliorating, or correcting dysfunctions or diseases including, but not limited to, cancer, diabetes, COPD, and peripheral and central nervous system disorders.

15 Claims, 24 Drawing Sheets

Fig. 1

```
tcggagactg actgctacga catcatcgag gtcttgggca
aggggacctt cggggaggta gccaagggct ggcggcggag
cacgggcgag atggtggcca tcaagatcct caagaatgac
gcctaccgca accgcatcat caagaacgag ctgaagctgc
tgcactgcat gcgaggccta gaccctgaag aggcccacgt
catccgcttc cttgagttct tccatgacgc cctcaagttc
tacctggtct ttgagctgct ggagcaaaac cttttcgagt
tccagaagga gaacaacttc gcgcccctcc ccgcccgcca
catccgtaca gtcaccctgc aggtgctcac agccctggcc
cggctcaagg agctggctat catccacgct gatctcaagc
ctgagaacat catgctggtg gaccagaccc gctgcccctt
cagggtcaag gtgattgact cggatccgc cagcattttc
agcgaggtgc gctacgtgaa ggagccatac atccagtcgc
gcttctaccg ggcccctgag atcctgctgg ggctgccctt
ctgcgagaag gtggacgtgt ggtccctggg ctgcgtcatg
gctgagctgc acctgggctg gcctctctac cccggcaaca
acgagtacga ccaggtgcgc tacatctgcg aaacccaggg
cctgcccaag ccacacctgt tgcacgccgc ctgcaaggcc
caccacttct tcaagcgcaa ccccacccct gacgctgcca
acccctggca gctcaagtcc tcggctgact acctggccga
gacgaaggtg cgcccattgg agcgccgcaa gtatatgctc
aagtcgttgg accagattga gacagtgaat ggtggcagtg
tggccagtcg gctaaccttc cctgaccggg aggcgctggc
ggagcacgcc gacctcaaga gcatggtgga gctgatcaag
cgcatgctga cctgggagtc acgaacgc atcagcccca
gtgctgccct gcgccacccc ttcgtgtcca tgcagcagct
gcgcagtgcc cacgagacca cccac
```

Fig. 2

```
SETDCYDIIE VLGKGTFGEV AKGWRRSTGE MVAIKILKND
AYRNRIIKNE LKLLHCMRGL DPEEAHVIRF LEFFHDALKF
YLVFELLEQN LFEFQKENNF APLPARHIRT VTLQVLTALA
RLKELAIIHA DLKPENIMLV DQTRCPFRVK VIDFGSASIF
SEVRYVKEPY IQSRFYRAPE ILLGLPFCEK VDVWSLGCVM
AELHLGWPLY PGNNEYDQVR YICETQGLPK PHLLHAACKA
HHFFKRNPHP DAANPWQLKS SADYLAETKV RPLERRKYML
KSLDQIETVN GGSVASRLTF PDREALAEHA DLKSMVELIK
RMLTWESHER ISPSAALRHP FVSMQQLRSA HETTH
```

Fig. 3

MASHVQVFSPHTLQSSAFCSVKKLKVEPSSNWDMTGYGSHSKVYSQSKNIPPS
QPASTTVSTSLPIPNPSLPYEQTIIFPGSTGHIVVTSASSTSVTGQVLGGPHN
LMRRSTVSLLDTYQKCGLKRKSEEIENTSSVQIIEEHPPMIQNNASGATVATA
TTSTATSKNSGSNSEGDYQLVQHEVLCSMTNTYEVLEFLGRGTFGQVVKCWKR
GTNEIVAIKILKNHPSYARQGQIEVSILARLSTESADDYNFVRAYECFQHKNH
TCLVFEMLEQNLYDFLKQNKFSPLPLKYIRPVLQQVATALMKLKSLGLIHADL
KPENIMLVDPSRQPYRVKVIDFGSASHVSKAVCSTYLQSRYYRAPEIILGLPF
CEAIDMWSLGCVIAELFLGWPLYPGASEYDQIRYISQTQGLPAEYLLSAGTKT
TRFFNRDTDSPYPLWRLKTPDDHEAETGIKSKEARKYIFNCLDDMAQVNMTTD
LEGSDMLVEKADRREFIDLLKKMLTIDADKRITPIETLNHPFVTMTHLLDFPH
STHVKSCFQNMEICKRRVNMYDTVNQSKTPFITHVAPSTSTNLTMTFNNQLTT
VHNQPSAASMAAVAQRSMPLQTGTAQICARPDPFQQALIVCPPGFQGLQASPS
KHAGYSVRMENAVPIVTQAPGAQPLQIQPGLLAQQAWPGGAQQILLPPAWQQL
TGVATHTSVQHAAVIPETMAGTQQLADWRNTHAHGSHYNPIMQQPTLLTGHVT
LPAAQPLNVGVAHVMRQQPTSTTSSRKSKQHQPSMRNVSTCEVTSSQSTSSPQ
RSKRVKENTPPRCAMVHSSPACSTSVTCGWGDVASSTTRERQRQTIVIPDTPS
PTVSVITISSDTDEEEQKHAPTSTVSKQRKNVISCVTVHDSPYSDSSSNTSP
YSVQQRTGHNGTNTLDTKGALENHCTGNPRTIIVPPLKTQASEVLVECDSLGP
AVSTGHHSSSFKCKSSSTVTSTSGHSSGSSSGAIAYRQQRPGPHFQQQQPLNL
SQAQPHMATDRTGSHRRQQAYITPTMAQAPYTFPHNSPSHGTVHPHLAAAAHL
PTQPHLYTYTAPTALGSTGTVAHLVASQGSARHTVQHTAYPASIVHQVPVSMG
PRVLPSPTIHPSQYPAQFAHQTYISASPASTVYTGYPLSPAKVNQYPYI

Fig. 4

MAPVYEGMASHVQVFSPHTLQSSAFCSVKKLKVEPSSNWDMTGYGSHSKVYSQ
SKNIPPSQPASTTVSTSLPVPNPSLPYEQTIVFPGSTGHIVVTSASSTSVTGQ
VLGGPHNLMRRSTVSLLDTYQKCGLKRKSEEIENTSSVQIIEEHPPMIQNNAS
GATVATATTSTATSKNSGSNSEGDYQLVQHEVLCSMTNTYEVLEFLGRGTFGQ
VVKCWKRGTNEIVAIKILKNRPSYARQGQIEVSILARLSTESADDYNFVRAYE
CFQHKNHTCLVFEMLEQNLYDFLKQNKFSPLPLKYIRPVLQQVATALMKLKSL
GLIHADLKPENIMLVDPSRQPYRVKVIDFGSASHVSKAVCSTYLQSRYYRAPE
IILGLPFCEAIDMWSLGCVIAELFLGWPLYPGASEYDQIRYISQTQGLPAEYL
LSAGTKTTRFFNRDTDSPYPLWRLKTPDDHEAETGIKSKEARKYIFNCLDDMA
QVNMTTDLEGSDMLVEKADRREFIDLLKKMLTIDADKRITPIETLNHPFVTMT
HLLDFPHSTHVKSCFQNMEICKRRVNMYDTVNQSKTPFITHVAPSTSTNLTMT
FNNQLTTVHNQAPSSTSATISLANPEVSILNYPSTLYQPSAASMAAVAQRSMP
LQTGTAQICARPDPFQQALIVCPPGFQGLQASPSKHAGYSVRMENAVPIVTQA
PGAQPLQIQPGLLAQQAWPSGTQQILLPPAWQQLTGVATHTSVQHATVIPETM
AGTQQLADWRNTHAHGSHYNPIMQQPALLTGHVTLPAAQPLNVGVAHVMRQQP
TSTTSSRKSKQHQSSVRNVSTCEVSSSQAISSPQRSKRVKENTPPRCAMVHSS
PACSTSVTCGWGDVASSTTRERQRQTIVIPDTPSPTVSVITISSDTDEEEQK
HAPTSTVSKQRKNVISCVTVHDSPYSDSSSNTSPYSVQQRAGHNNANAFDTKG
SLENHCTGNPRTIIVPPLKTQASEVLVECDSLVPVNTSHHSSSYKSKSSSNVT
STSGHSSGSSSGAITYRQQRPGPHFQQQQPLNLSQAQQHITTDRTGSHRRQQA
YITPTMAQAPYSFPHNSPSHGTVHPHLAAAAAAAHLPTQPHLYTYTAPAALGS
TGTVAHLVASQGSARHTVQHTAYPASIVHQVPVSMGPRVLPSPTIHPSQYPAQ
FAHQTYISASPASTVYTGYPLSPAKVNQYPYI

Fig. 5 agcggagagccgactcaacagcgctggaacccattcggtggggcctggggccc
ctcatcccaagccaggagggtttctggggaggggtgcagcccctggcagactg
acagtgtggcctgggggtttggggtgccagggaagcaggggccaacctcata
ggaggagacacgagtgcggttctctttcccccactgggggcctgctgtgtca
gcagccaggcgggaggcctgggcggcagagccagtggtacagggcctgggca
gggcggtgtctggcagcagcggcaccatgtccatccagtcggagactgac
tgctacgacatcatcgaggtcttgggcaaggggaccttcggggaggtagccaa
gggctggcggcggagcacgggcgagatggtggccatcaagatcctcaagaatg
acgcctaccgcaaccgcatcatcaagaacgagctgaagctgctgcactgcatg
cgaggcctagaccctgaagaggcccacgtcatccgcttccttgagttcttcca
tgacgccctcaagttctacctggtctttgagctgctggagcaaaaccttttcg
agttccagaaggagaacaacttcgcgcccctccccgcccgccacatccgtaca
gtcaccctgcaggtgctcacagccctggcccggctcaaggagctggctatcat
ccacgctgatctcaagcctgagaacatcatgctggtggaccagacccgctgcc
ccttcagggtcaaggtgattgacttcggatccgccagcattttcagcgaggtg
cgctacgtgaaggagccatacatccagtcgcgcttctaccgggcccctgagat
cctgctggggctgcccttctgcgagaaggtggacgtgtggtccctgggctgcg
tcatggctgagctgcacctgggctggcctctctaccccggcaacaacgagtac
gaccaggtgcgctacatctgcgaaacccagggcctgcccaagccacacctgtt
gcacgccgcctgcaaggccaccacttcttcaagcgcaaccccaccctgacg
ctgccaaccctggcagctcaagtcctcggctgactacctggccgagacgaag
gtgcgcccattggagcgccgcaagtatatgctcaagtcgttggaccagattga
gacagtgaatggtggcagtgtggccagtcggctaaccttcctgaccggggagg
cgctggcggagcacgccgacctcaagagcatggtggagctgatcaagcgcatg
ctgacctgggagtcacacgaacgcatcagcccagtgctgccctgcgccaccc
cttcgtgtccatgcagcagctgcgcagtgcccacgagaccacccac

Fig. 6

SGEPTQQRWNPFGGAWGPSSQARRVSGEGCSPWQTDSVAWGFGGAREAGANLI
GGDTSAVLFPPLGGLLCQQPGGRPGRQSQWYRGLGRAVSGSSGTMSTIQSETD
CYDIIEVLGKGTFGEVAKGWRRSTGEMVAIKILKNDAYRNRIIKNELKLLHCM
RGLDPEEAHVIRFLEFFHDALKFYLVFELLEQNLFEFQKENNFAPLPARHIRT
VTLQVLTALARLKELAIIHADLKPENIMLVDQTRCPFRVKVIDFGSASIFSEV
RYVKEPYIQSRFYRAPEILLGLPFCEKVDVWSLGCVMAELHLGWPLYPGNNEY
DQVRYICETQGLPKPHLLHAACKAHHFFKRNPHPDAANPWQLKSSADYLAETK
VRPLERRKYMLKSLDQIETVNGGSVASRLTFPDREALAEHADLKSMVELIKRM
LTWESHERISPSAALRHPFVSMQQLRSAHETTH

Fig. 7

CTGAGAAGTCGGTACATGTGGTGCCACAGCAGGAGTGCCCAGGCCCTAGCCCT
GCACAATGGTCAACCCTGCCCCCTTCTCCATGCCCCGCCAGGTGCGCCCATTG
GAGCGCCGAAAGTATATGCTCAAGTCGTTGGACCAGATTGAGACAGTGCATGG
TGGCAGTGTGGCCAGTCGGCTAACCTTCCCTGACCGGGGAGGCGCTGGCGGAC
ACACGCCGACCTCAAGAGCATGGTAGACCTGAGCAAGCCAGG

Fig. 8

CACGAGGCCCAGCTCCAAAAAAAAAAAGAAAGAAAGAAATCTGGTACAAGAG
GAAAAACTGGAGAATTGAAGCAGCAAGAGAGCTTCAAGTCAGATCATGGGCAG
AAGCCAGGGCAATACTATTTGGCTCCCACAACAGGTGATTTTGGGAGCCCTGA
GTCCAGATACATGTCCGGCTGGTGTCTCCCACACCCCACCAGGTACGCCCACT
GGAGCGCCGCAAGTACATGCTCAAATCCTTGGACCAAATTGAGACGGTGAATG
GTGGCGGCGCTGTGAATCGGTTGAGTTTTCCAGACCGGGAGGCACTGGCTGGA
ACACGCGGACCTCAAGAGCATGGTGGAGCTGATTAAACGCATGCTGACATGGG
AGT

Fig. 9

AGCGGATCATCCCAAGCCAGGAGGGTTTCTGGGGAGGGGTGCAGCCCCTGGCA
GACTGACAGTGTGGCCTGGGGGTTTGGGGGTGCCAGGGAAGCAGGGGCCAACC
TCATAGGAGGAGACACGAGTGCGGTTCTCTTTCCCCCACTGGGGGGCCTGCTG
TGTCAGCAGCCAGGCGGGAGGCCTGGGCGGCAGAGCCAGTGGTACAGGGGCCT
GGGCAGGGCGGTGTCTGGCAGCAGCGGCACCATGTCCACCATCCAGTCGGAGA
CTGACTGCTACGACATCATCGAGGTCTTGGGCAAGGGGACCTTCGGGGAGGTA
GCCAAGGGCTGGCGGCGGAGCACGGGCGAGATGGTGGCCATCAAGATCCTCAA
GAATGACGCCTACCGCAACCGCATCATCAAGAACGAGCTGAAGCTGCTGCACT
GCATGCGAGGCCTAGACCCTGAAGAGGCCCACGTCATCCGCTTCCTTGAGTTC
TTCCATGACGCCCTCAAGTTCTACCTGGTCTTTGAGCTGCTGGAGCAAAACCT
TTTCGAGTTCCAGAAGGAGAACAACTTTCGGCGCCCTCCCCGCCCGCCACAT
CCGTACAGTCACCCTGCAGGTGCTCACAGCCCTGGCCCGGCTCAAGGAGCTGG
CTATCATCCACGCTGATCTCAAGGCCTGAGAACATCATGCTGGTGGACCAGAC
CCGCTGCCCCCTTCAGGGTCAAGGTGATTGACTTCGGATCCGGCAGCATTTTC
AGCGAGGTGCGCTACGTGAAGGAGCCATAAATCAGGTCGAGCTTCTACACGGG
GCCCTGAGATC

Fig. 10

AGCGGAGAGCCACTCAACAGCGCTGGAACCCATTCGGTGGGGCCTGGGGCCCC
TCATCCCAAGCCAGGAGGGTTTCTGGGGAGGGGTGCAGCCCCTGGCAGACTGA
CAGTGTGGCCTGGGGGTTTGGGGGTGCCAGGGAAGCAGGGGCCAACCTCATAG
GAGGAGACACGAGTGCGGTTCTCTTTCCCCCACTGGGGGGCCTGCTGTGTCAG
CAGCCAGGCGGGAGGCCTGGGCGGCAGAGCCAGTGGTACAGGGGCCTGGGCAG
GGCGGTGTCTGGCAGCAGCGGCACCATGTCCACCATCCAGTCGGAGACTGACT
GCTACGACATCATCGAGGTCTTGGGCAAGGGGACCTTCGGGGCAGGTAGCCAA
GGGCTGGCGGCGGAGCACGGGCGAGATGGTGGCCATCAAGATCCTCAAGACTG
ACGCCTACCGCAACCGCATCATCAAAACACGAGCTGAAGCTGCTGCACTGCAT
GCGAGGCCTAGACCCTGACCGACGGCCCACGTCATCCGCTTCCTTGAGTTCTT
CCATGACGCCCTCAAGTTCTACCTGGTCTTCGAGCTGCTGGAGCAAAACCTTT
CCGAGTTCCAGAAGGAGAACAA

Fig. 11

AGCGGACTCAACAGCGCTGGAACCCATTCGGTGGGGCCTGGGGCCCCTCATCC
CAAGCCAGGAGGGTTTCTGGGGAGGGGTGCAGCCCCTGGCAGACTGACAGTGT
GGCCTGGGGGTTTGGGGGTGCCAGGAAGCAGGGGCCAACCTCATAGGAGGAGA
CACGAGTGCGGTTCTCTTTCCCCCACTGGGGGGCCTGCTGTGTCAGCAGCCAG
GCGGGAGGCCTGGGCGGCAGAGCCAGTGGTACAGGCGCCTGGGCAGGGCGGTG
TCTGGCAGCAGCGGCACCATGTCCACCATCCAGTCGGAGACTGACTGCTACGA
CATCATCGAGGTCTTGGGCAAGGGGACCTTCGGGGAGGTAGCCAAGGGCTGGC
GGCGGAGCACGGGCGAGATGGTGGCCATCAAGATCCTCAAGAATGACGCCTAC
CGCAACCGCGATCATCAAGAACGAGCTGAAGCTGCTGCACTGCATGCGAGGCC
TAGACCCTGAAGAGGCCCACGTCATCCGCTTCCTTGAGTTCTTCCATGACGCC
CTCAAGTTCTACCTGGTCTTTGAGCTGCTGGAGCAAAAGCTTTTCGAGTTCCA
GAAGGAGAACAACCTTGGGCCC

Fig. 12 msgggpsgggpggsgrartssfaepggggggggggpggsasgpggtgggkasv
gamgggvgasssgggpggsggggsggpgagtsfpppgvklgrdsgkvttvvat
lgqgpersqevaytdikvigngsfgvvyqarlaetrelvaikkvlqdkrfknr
elqimrkldhcnivrlryffyssgekkdelylnlvleyvpetvyrvarhftka
kltipilyvkvymyqlfrslayihsqgvchrdikpqnllvdpdtavlklcdfg
sakqlvrgepnvsyicsryyrapelifgatdytssidvwsagcvlaelllgqp
ifpgdsgvdqlveiikvlgtptreqiremnpnytefkfpqikahpwtkvfksr
tppeaialcsslleytpssrlspleacahsffdelrclgtqlpnnrplpplfn
fsagelsiqpslnailipphlrspagttltpssqaltetptssdwqstdatp
tltnss

Fig. 13

BLASTP - alignment of 426_prot against trembl|AF144573|AF144573 1
product: "Mx-interacting protein kinase PKM"; Mesocricetus auratus
Mx-interacting protein kinase PKM mRNA, complete cds.
This hit is scoring at : 5e-92 (expectation value)
Alignment length (overlap) : 356
Identities : 50%
Scoring matrix : BLOSUM62 (used to infer consensus pattern)
Database searched : nrdb

```
Q:  1   SETDCYDIIEVLGKGTFGEVAKGWRRSTGEMVAIKILKNDAYRNRIIKNELKLLHCMRGL
        S T.:Y::E.LG:GTFG:V.K W:R.T.E:VAIKILKN..   R   : E::L :  :
H:187   SMTNTYEVLEFLGRGTFGQVVKCWKRGTNEIVAIKILKNHPSYARQGQIEVSILARLSTE
        The protein-kinase-ATP region (prosite) is shown in bold
        The ATP binding site is labeled bold in all lanes DPEEAHVIRFLEFFHDALKFYLVFELLEQNLFEFQKENNFAPLPARHIRTVTLQVLTALA
        .:: :::R .E F .      LVFE:LEQNL::F K:N.F:PLP.:::IR.V. QV.TAL.
        SADDYNFVRAYECFQHKNHTCLVFEMLEQNLYDFLKQNKFSPLPLKYIRPVLQQVATALM RLKELAIIHADLKPENIMLVDQTRCPFRVKVIDFGSASIFSEVRYVKEPYIQSRFYRAPE
        :LK.L.:IHADLKPENIMLVD.:R P:RVKVIDFGSAS .S:   V..Y:QSR:YRAPE
        KLKSLGLIHADLKPENIMLVDPSRQPYRVKVIDFGSASHVSKA--VCSTYLQSRYYRAPE
        The protein-kinase-ST region (prosite) is shown in bold
        The active site aspartic acid is shown bold in all lanes ILLGLPFCEKVDVWSLGCVMAELHLGWPLYPGNNEYDQVRYICETQGLPKPHLLHAACKA
        I:LGLPFCE.:D:WSLGCV:AEL.LGWPLYPG :EYDQ:RYI.:TQGLP.:LL.A..K.
        IILGLPFCEAIDMWSLGCVIAELFLGWPLYPGASEYDQIRYISQTQGLPAEYLLSAGTKT HHFFKRNPHPDAANP-WQLKSSADYLAETKVRPLERRKYMLKSLDQIETVNGGSVASRLT
        .FF.R:    D:. P W:LK:. D: AET ::. E.RKY:...LD..:.VN   ....
        TRFFNRD--TDSPYPLWRLKTPDDHEAETGIKSKEARKYIFNCLDDMAQVN-----MTTD
```

Fig. 13 (continued)

```
FPDREALAEHADLKSMVELIKRMLTWESHERISPSPSAALRHPFVSMQQLRSAHETTH    355
...:.L.E.AD ..:.:L:K:MLT :.:.:RI:P ..L.HPFV:M..L  .:TH
LEGSDMLVEKADRREFIDLLKKMLTIDADKRITPIETLNHPFVTMTHLLDFPHSTH      533
```

The eukaryotic protein kinase domain region identified by pfam homology is underlined.

Fig. 14

HMMPFAM - alignment of 426_prot against pfam|hmm|pkinase
Eukaryotic protein kinase domain
This hit is scoring at : 177.1
Scoring matrix : BLOSUM62 (used to infer consensus pattern)

```
Q:   6 YDIIEVLGKGTFGEVAKGWRRsTGEMVAIKILknDAYRNriiKNELKLLHCMRgldpeEA
       Y:::E LG:G:FG:V K. .: FG:V K.  : TG::VA:KILK .: :  .E:::L. :. .:
H:   1 yelleklGeGsFGkVykakhk.tgkivAvKilk.kesls...lrEiqilkrls......Hp HVIRFLEFFH-DALKFYLVFELLEQ-NLFEFQKENNfaPLPARHIRTVTLQVLTALARLK     232
     :::R.L .F. .  YLV.E.:E    :LF:: :.N.    PL.:.:..::LQ:L..L. L.
     NIvrllgvfedtddhlylvmEymeggGdlfdylrrng.plsekeakkialQilrGleYLH     217

ELAIIHADLKPENIMLVDQtrcpFRVKVIDFGSASIFsevrYVKEPYIQSRFYR-APEI-
     ..I:H.DLKPENI:L:.   .VK:.DFG A.:   : :    :Y. APE:
     sngivHRDLkpeNIlden....gtvKiaDFGLArli...ekittfvGTpwYmmAPEvi LLGLPFCEKVDVWSLGCVMAELHLGWPLYP-------GNnEYDQVRyICeTQGLPKPH
     LG  : ...KVDVWSLG.::  EL .G PL:P       G:  E.DQ:  I   LP
     legrgysskvDvWSlGviLyElltggplfpgadlpaftggd.evdqli.if.vlklPfsd
```

HMMPFAM - alignment of 426_prot against pfam|hmm|pkinase
Eukaryotic protein kinase domain
This hit is scoring at : 16.1
Scoring matrix : BLOSUM62 (used to infer consensus pattern)

```
Q: 317 ELIKRMLTWESHERI---SPSAALRHPFV     342
       :L:K:.L. :..:R       ...:L.HP::
H: 250 dLlkkcLnkDPskRpGsatakeilnhpwf     278
```

Fig. 15

```
BLASTP - alignment of 426 prot against pdb|1JST|1JST-A
cyclin-dependent kinase-2(cdk2)cyclin afragment: residues 173-432;
This hit is scoring at : 2e-28 (expectation value)
Alignment length (overlap) : 222
Identities : 32 %
Scoring matrix : BLOSUM62 (used to infer consensus pattern)
Database searched : nrdb Q:   9 IEVLGKGTFGEVAKGWRRSTGEMVAIKILKNDAYRNRIIKNELKLLHCMRGLDPEEAHVI
       :E :G:G:G V K.  : TGE:VA:K :: D.   .:  .::  .:::: L:   .::::
H:   7 VEKIGEGTYGVVYKARNKLTGEVVALKKIRLDTETEGVPSTAIREISLLKELN--HPNIV RFLEFFHDALKFYLVFELLEQNLFEFQKENNFAPLPARHIRTVTLQVLTALARLKELAII
       ::L:..H.  K.YLVFE.L.Q:L :F...:  :P. I:..:.Q:L..LA  ..  .::
       KLLDVIHTENKLYLVFEFLHQDLKKFMDASALTGIPLPLIKSYLFQLLQGLAFCHSHRVL HADLKPENIMLVDQTRCPFRVKVIDFGSASIFSEVRYVKEPYIQSRFYRAPEILLGLP-F
       H.DLKP:N::   :   .:K: .DFG A.F.   .   .    . :YRAPEILLG...  :
       HRDLKPQNLLINTEG----AIKLADFGLARAFGVPVRTYXHEVVTLWYRAPEILLGCKYY CEKVDVWSLGCVMAELHLGWPLYPGNNEYDQVRYICETQGLP            229
       ...VD:WSLGC::.AE:     .L:PG::E.DQ:   I .T G.P
       STAVDIWSLGCIFAEMVTRRALFPGDSEIDQLFRIFRTLGTP            222
```

Fig. 16

BLASTN - alignment of 426 DNA against embl AC010271 AC010271

TBLASTN - alignment of 426 prot against embl AC010271 AC010271

Genewise analysis of target #426 using genomic sequence AC011471.5 and the hamst r protein as template(AF144573_1).
genewise output
Score 349.88 bits over entire alignment
Scores as bits over a synchronous coding model
Warning: The bits scores is not probabilistically correct for single seqs
See WWW help for more info

```
AF144573_1    187  SMTNTYEVLEFLGRGTFGQVVKCWKRGTNEIVAIKILKNHPSYARQGQI
                   S  T+  Y+++E LG+GTFG+V K W+R T E+VAIKILKN  R   +
                        SETDCYDIIEVLGKGTFGEVAKGWRRSTGEMVAIKILKNDAYRNRIIKN
AC010271.6  75384  tgagttgaaggtgagatgggagtccaaggaggaacaaggtcacaaaa
                   cacagaattattgagctgatcagggggcgcgcgcggacagagttaa
                   ggtccccccgccgacgcgggcgcgcgccgcccgtcccccccgc AF144573_1    236  EVSILARLSTESADDYNFVRAYECFQHKNHTCLVFEMLEQNLYDFLKQN
                   E+  +L     +         ++   +R  E F    LVFE+LEQNL++F K+N
                        ELKLLHCMRGLDPEEAHVIRFLEFFHDALKFYLVFELLEQNLFEFQKEN
AC010271.6  75531  gcacctacgcgcggcgactgttcggcattcgtccgcactgtcaga
                   atattagtgtacaacattgttattactatattttaaattataaaa
                   ggggccgacactagccccccgcctcccgccctggggactcgcgggc
```

Fig. 16 (continued)

```
AF144573_1    285  KFSPLPLKYIRPVLQQVATALMKLKSLGLIHADLKPENIMLVDPSRQPY
                   F+PLP  ++IR V   QV TAL  +LK L  +IHADLKPENIMLVD +R P+
                   NFAPLPARHIRTVTLQVLTALARLKELAIIHADLKPENIMLVDQTRCPF
AC010271.6  75678  atgcccgccacagaccgcagcgccagcgacggcacgaaacggcactct
                   atcctccgatgctctattcctcgtaatcttacatacaatttaacggct
                   ccgcccccctaccgggcacgcgcgggtcccctcgtgccgggcgcccc AF144573_1    334  RVK                    VIDFGSASHVSKA--VCSTYLQS
                   RVK                    VIDFGSAS    S+    V    Y+QS
                   RVK                    VIDFGSASIFSEVRYVKEPYIQS
AC010271.6  75825  agaGTGAGTA Intron 1 CAGgagtgtgaataggctgagctact
                   gta<0-----[75834:81131]-0>ttatgccgttgataacatac
                   gcg                              gtccaccctccggaccggggaccgg AF144573_1    358  RYYRAPEIILGLPFCEAIDMWSLGCVIAELFLGWPLYPGASEYDQIRYI
                   R+YRAPEI+LGLPFCE +D+WSLGCV+AEL LGWPLYPG +EYDQ+RYI
                   RFYRAPEIILGLPFCEKVDVWSLGCVMAELHLGWPLYPGNNEYDQVRYI
AC010271.6  81201  cttcgcgaccgccttgagggttcgtgaggcccgtcctcgaagtgcgcta
                   gtagccattttgtctgaatatgctggttcatatggctacgaaaaatgat
                   cccgctgcgggggcccggcggcccgtgcgctgccccccgccgggccc
```

Fig. 16 (continued)

```
AF144573_1    407    SQTQGLPAEYLLSAGTKTKTTRFFNRDT--DSPYPLWRLKTPDDHEAETG
                     +TQGLP  +LL A   K   FF R+    D+  P W+LK+   D+ AET
AC010271.6   81348   CETQGLPKPHLLHAACKAHHFFKRNPHPDAANP-WQLKSSADYLAETK
                     tgacgccaccctcgtagccttacaccgggac tccattggtcggaa
                     gacagtcacattacgacaattagacacaca gatacccaatcaca
                     cacgcgcgacggccccgcccctctccc   ggcgcgtccgggg
AF144573_1    453                                 IKSKEARKYIFNCLDDMAQVN---MT
                                                   ++  E  RKY++ +   LD +  VN
AC010271.6   81489   GTAAGGG Intron 2   CAGgcctgccatacattgcagagaggagg
                     <0-----[81489:84102]-0>tgctaggaattactaatactagggtc
                                           gcaggccgtgcggggcgtgagttctgc VRPLERRKYMLKSLDQIETVNGGSVA
AF144573_1    476    TDLEGSDM--LVEKADRREFIDLLKKMLTIDADKRITPIETLNHPFVTM
                     + L   D    L E AD  +  +++L+K+MLT  ++  +RI+P  L   HPFV+M
AC010271.6   84181   SRLTFPDREALAEHADLKSMVELIKRMLTWESHERISPSAALRHPFVSM
                     accatcgcggcgggcaacaggcaaaggcaacacatgtcgcaacaggcccctgta
                     ggtctcagactcaacatagttattagttcgacaagtgcgcctgacttct
                     tgacctcggggggcgggcgcgggggacacccccctcgcgcccgcg AF144573_1    523    THLLDFPHSTH
                     L        +TH
AC010271.6   84328   QQLRSAHETTH
                     cccagcgaac
                     aatggcaacca
                     gggctcccgccc
```

Fig. 16 (continued)

```
//
Gene 1
Gene 75384 84360
  Exon 75384 75833
  Exon 81132 81488
  Exon 84103 84360
//
>AC010271.6.[75384:84360].sp.tr
SETDCYDIIEVLGKGTFGEVAKGWRRSTGEMVAIKILKNDAYRNRIIKNELKLLHCMRGL
DPEEAHVIRFLEFFHDALKFYLVFELLEQNLFEFQKENNFAPLPARHIRTVTLQVLTALA
RLKELAIIHADLKPENIMLVDQTRCPFRVKVIDFGSASIFSEVRYVKEPYIQSRFYRAPE
ILLGLPFCEKVDVWSLGCVMAELHLGWPLYPGNNEYDQVRYICETQGLPKPHLLHAACKA
HHFFKRNPHPDAANPWQLKSSADYLAETKVRPLERRKYMLKSLDQIETVNGGSVASRLTF
PDREALAEHADLKSMVELIKRMLTWESHERISPSAALRHPFVSMQQLRSAHETTH
//
>AC010271.6.[75384:84360].sp
TCGGAGACTGACTGCTACGACATCATCGAGGTCTTGGGCAAGGGGACCTTCGGGGAGTA
GCCAAGGGCTGGCGGCGGAGCACGGGCGAGATGGTGGCCATCAAGATCCTCAAGAATGAC
GCCTACCGCAACCGCATCATCAAGAACGAGCTGAAGCTGCTGCACTGCATGCGAGGCCTA
GACCCTGAAGAGAGCCACGTCATCCGCTTCCTTGAGTTCTTCCATGACGCCCTCAAGTTC
TACCTGGTCTTTGAGCTGCTGGAGCAAAACCTTTTCGAGTTCCAGAAGGAGAACAACTTC
GCGCCCCTCAAGCACCGTATCCACGCTACACGCTCAAGCCTGAGAACATCATGCTGGTG
CGGCTCAAGGAGCTGCTGCCCCTTCAAGGTCAAGGTGACCATCAAGCCAGCATTTC
GACCAGAGCCCGTGCGCTACGTGAAGGAGCCATACATCCAGTCGCTTCTACCGGGCTGAG
AGCGAGGTGCGCTGGAGCTGCACCTGGGCTGCGTGATGGCCGAACTGCATCTGGGC
ATCCTGCTGCTGGGCTGGCCCTTCTACCCCGGCCACACACAGAGTACGACCAGGTGCGC
GCTGAGCTGCACCTGGAACCCAGGCGTGCAACCCTGTTGCACCCCTGCAGTCAAGTCC
TACATCTGCGAAACCCAGGGCCTGCCAAGCCCACCCTGACGCTGCCAACCCTGCAGTCAAGTCC
CACCACTTCTTCAAGCGCAACCCTGGCCGAGAACAGTGAAAGTGCGCCCAAGTCGGCTAACCTTC
TCGGCTGACTACCTGGCCGAGACAAGGTGCGCCGAGACAGTCGGAGGCCGCAAGTCGCTATATGCTC
AAGTCGTTGGACCAGATTGAGACAGTGAATGGTGGCAGTGTGGCCAGTCGGCTAACCTTC
CCTGACCGGGAGGCGCTGGCGGAGCACGCCGACCTGCAGAGACATGGTGGAGCTGATCAAG
CGCATGCTGACCTGGGAGTCACACGAACGCATCAGCCCCAGTGCTGCCCTGCGCCACCCC
```

Fig. 16 (continued)

TTCGTGTCCATGCAGCAGCTGCGCAGTGCCACGAGACCACCCAC
//

| | | | | | | | | |
|---|---|---|---|---|---|---|---|---|
| AC010271.6 | GeneWise | match | 75384 | 84360 | 349.88 | + | . | . AF144573_1 |
| AC010271.6 | GeneWise | cds | 75384 | 75833 | 0.00 | + | 0 | AF144573_1 |
| AC010271.6 | GeneWise | intron | 75834 | 81131 | 0.00 | + | . | AF144573_1 |
| AC010271.6 | GeneWise | cds | 81132 | 81488 | 0.00 | + | 0 | AF144573_1 |
| AC010271.6 | GeneWise | intron | 81489 | 84102 | 0.00 | + | . | AF144573_1 |
| AC010271.6 | GeneWise | cds | 84103 | 84360 | 0.00 | + | 0 | AF144573_1 |

Fig. 17

BLASTP - alignment of 426 protc against swissnew|P49840|KG3A_HUMAN
GLYCOGEN SYNTHASE KINASE-3 ALPHA (EC 2.7.1.37) (GSK-3 ALPHA)
//:trembl|AC006486|AC006486_1 gene: "GSK3A"; product: "KG3A_HUMAN";
Homo sapiens chromosome 19, BAC CIT-B-147B23 (BC85722), complete sequence.

This hit is scoring at : 9e-30 (expectation value)
Alignment length (overlap) : 397
Identities : 29 %
Scoring matrix : BLOSUM62 (used to infer consensus pattern)
Database searched : nrdb_1_;

```
Q:  13  GGAWGPSSQARRVSGEGCSPWQTDSVAWGFG------GAREAGANLIGGDTSAVLFPPLG
        GG. GP...A. .G.G ..:.:: G.G .:G. :G.  GG. :.: FPP
H:  31  GGGGGPGGSASGPGGTGGGKASVGAMGGGVGASSSGGPGGSGGGPGAGTSFPP--

GLLCQQPGGRPGRQSQWYRGLGLIGRAVSGSSGTMSTIQSETDCYDIIEVLGKGTFGEVAKGW
        PG : GR.S    G .V .:  G  .:S:. Y. I:V.G.G:FG V :.
        ------PGVKLGRDS----GKVTTVVATLG-QGPERSQEVAYTDIKVIGNGSFGVVYQAR

RRSTGEMVAIK-ILKNDAYRNRIIKNELKLLHCMRGLDPEEAHVIRFLEFFH------DA
        .T E:VAIK :L::.::NR ::    KL HC                :::R.   FF:   D.
        LAETRELVAIKKVLQDKRFKNRELQIMRKLDHC------------NIVRLRYFFYSSGEKKDE

LKFYLVFELLEQNLFEFQKENNFAPL--PARHIRTVTLQVLTALARLKELAIIHADLKPE
        L. LV.E.:.:.:..:::   A.L P. :.::..::.:Q:..:.:LA .:..:.H.D:KP:
        LYLNLVLEYVPETVYRVARHFTKAKLTIPILYVKVYMYQLFRSLAYIHSQGVCHRDIKPQ

NIMLVDQTRCPFFRVKVIDFGSASIFSEVRYVKEP---YIQSRFYRAPEILLGLP-FCEKV
        N::. :T..  :K: .DFGSA.          EP      YI SR:YRAPE:::G. .:.::
        NLLVDPDTAV---LKLCDFGSAKQLVR----GEPNVSYICSRYYRAPELIFGATDYTSSI
```

Fig. 17 (continued)

```
DVWSLGCVMAELHLGWPLYPGNNEYDQVRYICETQGLPKPHLLH--------AACKA
DVWS.GCV:AEL LG P::PG:: .DQ:  I.:. G.P.:.         ..:KA
DVWSAGCVLAELLLGQPIFPGDSGVDQLVEIIKVLGTPTREQIREMNPNYTEFKFPQIKA

HHF---FKRNPHPDAANPWQLKSSADYLAETKVRPLE          376
H : FK.. P:A.      .:S .:Y..:::.PLE
HPWTKVFKSRTPPEAIA--LCSSLLEYTPSSRLSPLE          396
```

Fig. 18

BLASTP - alignment of 426 protc against swissnew|Q9H2X6|HIK2_HUMAN
HOMEODOMAIN-INTERACTING PROTEIN KINASE 2 (EC 2.7.1.-).
//:tremblnew|AF208291|AF208291_1 product: "protein kinase HIPK2".
Homo sapiens protein kinase HIPK2 mRNA, complete cds.
This hit is scoring at : 3e-92 (expectation value)
Alignment length (overlap) : 372
Identities : 48 %
Scoring matrix : BLOSUM62 (used to infer consensus pattern)
Database searched : nrdb_1_j

```
Q:  92 SGSSGTMSTIQSETDC-----YDIIEVLGKGTFGEVAKGWRRSTGEMVAIKILKNDAYRN
       S.S.G....:Q.E..C      Y:::E.LG:GTFG:V.K W:R.T.E:VAIKILKN.
H: 178 SNSEGDYQLVQHEVLCSMTNTYEVLEFLGRGTFGQVVKCWKRGTNEIVAIKILKNRPSYA

RIIKNELKLLHCMRGLDPEEAHVIRFLEFFHDALKFYLVFELLEQNLFEFQKENNFAPLP
       R E::L .: :::L :  :  ::R .E F...   LVFE:LEQNL::F K:N.F:PLP
       RQGQIEVSILARLSTESADDYNFVRAYECFQHKNHTCLVFEMLEQNLYDFLKQNKFSPLP

ARHIRTVTLQVLTALARLKELAIIHADLKPENIMLVDQTRCPFRVKVIDFGSASIFSEVR
       .::IR.V. QV.TAL..LK.L.:IHADLKPENIMLVD..:R P:RVKVIDFGSAS .S::
       LKYIRPVLQQVATALMKLKSLGLIHADLKPENIMLVDPSRQPYRVKVIDFGSASHVSKA-

YVKEPYIQSRFYRAPEILLGLPFCEKVDVWSLGCVMAELHLGWPLYPGNNEYDQVRYICE
       V .Y:QSR:YRAPEI:LGLPFCE.:D:WSLGCV:AEL.LGWPLYPG :EYDQ:RYI.:
       -VCSTYLQSRYYRAPEILLGLPFCEAIDMWSLGCVIAELFLGWPLYPGASEYDQIRYISQ

TQGLPKPHLLHAACKAHHFFKRNPHPDAANP-WQLKSSADYLAETKVRPLERRKYMLKSL
       TQGLP..:LL.A..K..FF.R:  .D:  P W:LK:. D: AET :: .E.RKY:...L
       TQGLPAEYLLSAGTKTTRFFNRD--TDSPYPLWRLKTPDDHEAETGIKSKEARKYIFNCL

DQIETVNGGSVASRLTFPDREALAEHADLKSMVELIKRMLTWESHERISPSAALRHPFVS
       D..::           .L.E.AD ..:.:L:K:MLT :::RI:P .L.HPFV:
       DDMAQVN-----MTTDLEGSDMLVEKADRREFIDLLKKMLTIDADKRITPIETLNHPFVT
```

Fig. 18 (continued)

```
MQQLRSAHETTH   457
M.L..:TH
MTHLLDFPHSTH
```

Fig. 19

```
BLASTP - alignment of 426_protc against pdb|1CM8|1CM8-A
phosphorylated map kinase p38-gamma(stress-activated protein kinase-3, erk6, erk5).
This hit is scoring at : 2e-17 (expectation value)
Alignment length (overlap) : 333
Identities : 25 %
Scoring matrix : BLOSUM62 (used to infer consensus pattern)
Database searched : nrdb_1_;

Q: 130 TGEMVAIKIL-----KNDAYRNRIIKNELKLLHCMRGLDPEEAHVIRFLEFF------HDA
        TG..VAIK L    :::::R.:  EL:LL. MR    .:VI .L:.F       .D
H:  36 TGAKVAIKKLYRPFQSELFAKRAYR-ELRLLKHMR-----HENVIGLLDVFTPDETLDDF

LKFYLVFELLEQNLFEFQKENNFAPLPARHIRTVTLQVLTALARLKELAIIHADLKPENI
       .FYLV..:..:L...:K...  L.. .I :..Q:L..L. :..:.IIH.DLKP N:
       TDFYLVMPFMGTDLGKLMKHEK---LGEDRIQFLVYQMLKGLRYIHAAGIIHRDLKPGNL

MLVDQTRCPFRVKVIDFGSASIFSEVRYVKEPYIQSRFYRAPEILLG-LPFCEKVDVWSL
       .:...:    :K::DFG A.   :  .. :. :R:YRAPE::L. : .:.VD:WS:
       AVNEDCE-----LKILDFGLAR---QADSEMXGXVVTRWYRAPEVILNWMRYTQTVDIWSV

GCVMAELHLGWPLYPGNNEYDQVRYICETQGLPKPHLLHAACKAHHFFKRNPHPDAANPW
       GC:MAE: .G .L:.G:...DQ:::.DQ:: I....G.P..::
       GCIMAEMITGKTLFKGSDHLDQLKEIMKVTGTPPAEFVQ--------------------

QLKSSADYLAETKVRPLERRKYMLKSLDQIETVNGGSVASRLTFPDREALAEHADLKSMV
             E...YM K.L.::E. :  .S.:::              .V
       -------RLQSDEAKNYM-KGLPELEKKDFASILTNAS------------PLAV

ELIKRMLTWESHERISPSAALRHP-FVSMQQLR        450
       .L:::ML. :::.R:...AL.HP F S:.Q::
       NLLEKMLVLDAEQRVTAGEALAHPYFESLHQVQ
``` human serine/threonine kinase relative expression in cancer tissues.

human serine/threonine kinase relative expression in obesity and diabetes tissues.

SEQUENCE LISTING

<160> NUMBER OF SEQ ID NOS: 14

<210> SEQ ID NO 1
<211> LENGTH: 1065
<212> TYPE: DNA
<213> ORGANISM: Homo sapiens

<400> SEQUENCE: 1

```
tcggagactg actgctacga catcatcgag gtcttgggca aggggacctt cggggaggta      60
gccaagggct ggcggcggag cacgggcgag atggtggcca tcaagatcct caagaatgac     120
gcctaccgca accgcatcat caagaacgag ctgaagctgc tgcactgcat gcgaggccta     180
gaccctgaag aggcccacgt catccgcttc cttgagttct tccatgacgc cctcaagttc     240
tacctggtct ttgagctgct ggagcaaaac cttttcgagt tccagaagga gaacaacttc     300
gcgcccctcc ccgcccgcca catccgtaca gtcaccctgc aggtgctcac agccctggcc     360
```

-continued

```
cggctcaagg agctggctat catccacgct gatctcaagc ctgagaacat catgctggtg    420
gaccagaccc gctgcccctt cagggtcaag gtgattgact tcggatccgc cagcattttc    480
agcgaggtgc gctacgtgaa ggagccatac atccagtcgc gcttctaccg ggcccctgag    540
atcctgctgg ggctgccctt ctgcgagaag gtggacgtgt ggtccctggg ctgcgtcatg    600
gctgagctgc acctgggctg gcctctctac cccggcaaca acgagtacga ccaggtgcgc    660
tacatctgcg aaacccaggg cctgcccaag ccacacctgt tgcacgccgc ctgcaaggcc    720
caccacttct tcaagcgcaa ccccacccct gacgctgcca accctggca gctcaagtcc    780 tcggctgact acctggccga dacgaaggtg cgcccattgg agcgccgcaa gtatatgctc    840
aagtcgttgg accagattga dacagtgaat ggtggcagtg tggccagtcg gctaaccttc    900
cctgaccggg aggcgctggc ggagcacgcc gacctcaaga gcatggtgga gctgatcaag    960
cgcatgctga cctgggagtc acacgaacgc atcagcccca gtgctgccct gcgccaccc    1020 ttcgtgtcca tgcagcagct gcgcagtgcc cacgagacca cccac                   1065
```

<210> SEQ ID NO 2
<211> LENGTH: 355
<212> TYPE: PRT
<213> ORGANISM: Homo sapiens

<400> SEQUENCE: 2

```
Ser Glu Thr Asp Cys Tyr Asp Ile Ile Glu Val Leu Gly Lys Gly Thr
  1               5                  10                  15

Phe Gly Glu Val Ala Lys Gly Trp Arg Arg Ser Thr Gly Glu Met Val
             20                  25                  30

Ala Ile Lys Ile Leu Lys Asn Asp Ala Tyr Arg Asn Arg Ile Ile Lys
         35                  40                  45

Asn Glu Leu Lys Leu Leu His Cys Met Arg Gly Leu Asp Pro Glu Glu
     50                  55                  60

Ala His Val Ile Arg Phe Leu Glu Phe Phe His Asp Ala Leu Lys Phe
 65                  70                  75                  80

Tyr Leu Val Phe Glu Leu Leu Glu Gln Asn Leu Phe Glu Phe Gln Lys
                 85                  90                  95

Glu Asn Asn Phe Ala Pro Leu Pro Ala Arg His Ile Arg Thr Val Thr
            100                 105                 110

Leu Gln Val Leu Thr Ala Leu Ala Arg Leu Lys Glu Leu Ala Ile Ile
        115                 120                 125

His Ala Asp Leu Lys Pro Glu Asn Ile Met Leu Val Asp Gln Thr Arg
    130                 135                 140

Cys Pro Phe Arg Val Lys Val Ile Asp Phe Gly Ser Ala Ser Ile Phe
145                 150                 155                 160

Ser Glu Val Arg Tyr Val Lys Glu Pro Tyr Ile Gln Ser Arg Phe Tyr
                165                 170                 175

Arg Ala Pro Glu Ile Leu Leu Gly Leu Pro Phe Cys Glu Lys Val Asp
            180                 185                 190

Val Trp Ser Leu Gly Cys Val Met Ala Glu Leu His Leu Gly Trp Pro
        195                 200                 205

Leu Tyr Pro Gly Asn Asn Glu Tyr Asp Gln Val Arg Tyr Ile Cys Glu
    210                 215                 220

Thr Gln Gly Leu Pro Lys Pro His Leu Leu His Ala Ala Cys Lys Ala
225                 230                 235                 240

His His Phe Phe Lys Arg Asn Pro His Pro Asp Ala Ala Asn Pro Trp
                245                 250                 255
```

```
Gln Leu Lys Ser Ser Ala Asp Tyr Leu Ala Glu Thr Lys Val Arg Pro
            260                 265                 270

Leu Glu Arg Arg Lys Tyr Met Leu Lys Ser Leu Asp Gln Ile Glu Thr
            275                 280                 285

Val Asn Gly Gly Ser Val Ala Ser Arg Leu Thr Phe Pro Asp Arg Glu
            290                 295                 300

Ala Leu Ala Glu His Ala Asp Leu Lys Ser Met Val Glu Leu Ile Lys
305                 310                 315                 320

Arg Met Leu Thr Trp Glu Ser His Glu Arg Ile Ser Pro Ser Ala Ala
            325                 330                 335

Leu Arg His Pro Phe Val Ser Met Gln Gln Leu Arg Ser Ala His Glu
            340                 345                 350

Thr Thr His
        355

<210> SEQ ID NO 3
<211> LENGTH: 1162
<212> TYPE: PRT
<213> ORGANISM: Mesocricetus auratus

<400> SEQUENCE: 3

Met Ala Ser His Val Gln Val Phe Ser Pro His Thr Leu Gln Ser Ser
1               5                   10                  15

Ala Phe Cys Ser Val Lys Lys Leu Lys Val Glu Pro Ser Ser Asn Trp
            20                  25                  30

Asp Met Thr Gly Tyr Gly Ser His Ser Lys Val Tyr Ser Gln Ser Lys
        35                  40                  45

Asn Ile Pro Pro Ser Gln Pro Ala Ser Thr Thr Val Ser Thr Ser Leu
    50                  55                  60

Pro Ile Pro Asn Pro Ser Leu Pro Tyr Glu Gln Thr Ile Ile Phe Pro
65                  70                  75                  80

Gly Ser Thr Gly His Ile Val Val Thr Ser Ala Ser Ser Thr Ser Val
            85                  90                  95

Thr Gly Gln Val Leu Gly Gly Pro His Asn Leu Met Arg Arg Ser Thr
            100                 105                 110

Val Ser Leu Leu Asp Thr Tyr Gln Lys Cys Gly Leu Lys Arg Lys Ser
            115                 120                 125

Glu Glu Ile Glu Asn Thr Ser Ser Val Gln Ile Ile Glu Glu His Pro
            130                 135                 140

Pro Met Ile Gln Asn Asn Ala Ser Gly Ala Thr Val Ala Thr Ala Thr
145                 150                 155                 160

Thr Ser Thr Ala Thr Ser Lys Asn Ser Gly Ser Asn Ser Glu Gly Asp
                165                 170                 175

Tyr Gln Leu Val Gln His Glu Val Leu Cys Ser Met Thr Asn Thr Tyr
            180                 185                 190

Glu Val Leu Glu Phe Leu Gly Arg Gly Thr Phe Gly Gln Val Val Lys
            195                 200                 205

Cys Trp Lys Arg Gly Thr Asn Glu Ile Val Ala Ile Lys Ile Leu Lys
            210                 215                 220

Asn His Pro Ser Tyr Ala Arg Gln Gly Gln Ile Glu Val Ser Ile Leu
225                 230                 235                 240

Ala Arg Leu Ser Thr Glu Ser Ala Asp Asp Tyr Asn Phe Val Arg Ala
            245                 250                 255

Tyr Glu Cys Phe Gln His Lys Asn His Thr Cys Leu Val Phe Glu Met
```

-continued

```
                260                 265                 270
Leu Glu Gln Asn Leu Tyr Asp Phe Leu Lys Gln Asn Lys Phe Ser Pro
            275                 280                 285
Leu Pro Leu Lys Tyr Ile Arg Pro Val Leu Gln Val Ala Thr Ala
        290                 295                 300
Leu Met Lys Leu Lys Ser Leu Gly Leu Ile His Ala Asp Leu Lys Pro
305                 310                 315                 320
Glu Asn Ile Met Leu Val Asp Pro Ser Arg Gln Pro Tyr Arg Val Lys
                325                 330                 335
Val Ile Asp Phe Gly Ser Ala Ser His Val Ser Lys Ala Val Cys Ser
            340                 345                 350
Thr Tyr Leu Gln Ser Arg Tyr Tyr Arg Ala Pro Glu Ile Ile Leu Gly
        355                 360                 365
Leu Pro Phe Cys Glu Ala Ile Asp Met Trp Ser Leu Gly Cys Val Ile
    370                 375                 380
Ala Glu Leu Phe Leu Gly Trp Pro Leu Tyr Pro Gly Ala Ser Glu Tyr
385                 390                 395                 400
Asp Gln Ile Arg Tyr Ile Ser Gln Thr Gln Gly Leu Pro Ala Glu Tyr
                405                 410                 415
Leu Leu Ser Ala Gly Thr Lys Thr Thr Arg Phe Phe Asn Arg Asp Thr
            420                 425                 430
Asp Ser Pro Tyr Pro Leu Trp Arg Leu Lys Thr Pro Asp Asp His Glu
        435                 440                 445
Ala Glu Thr Gly Ile Lys Ser Lys Glu Ala Arg Lys Tyr Ile Phe Asn
    450                 455                 460
Cys Leu Asp Asp Met Ala Gln Val Asn Met Thr Thr Asp Leu Glu Gly
465                 470                 475                 480
Ser Asp Met Leu Val Glu Lys Ala Asp Arg Arg Glu Phe Ile Asp Leu
                485                 490                 495
Leu Lys Lys Met Leu Thr Ile Asp Ala Asp Lys Arg Ile Thr Pro Ile
            500                 505                 510
Glu Thr Leu Asn His Pro Phe Val Thr Met Thr His Leu Leu Asp Phe
        515                 520                 525
Pro His Ser Thr His Val Lys Ser Cys Phe Gln Asn Met Glu Ile Cys
    530                 535                 540
Lys Arg Arg Val Asn Met Tyr Asp Thr Val Asn Gln Ser Lys Thr Pro
545                 550                 555                 560
Phe Ile Thr His Val Ala Pro Ser Thr Ser Thr Asn Leu Thr Met Thr
                565                 570                 575
Phe Asn Asn Gln Leu Thr Thr Val His Asn Gln Pro Ser Ala Ala Ser
            580                 585                 590
Met Ala Ala Val Ala Gln Arg Ser Met Pro Leu Gln Thr Gly Thr Ala
        595                 600                 605
Gln Ile Cys Ala Arg Pro Asp Pro Phe Gln Gln Ala Leu Ile Val Cys
    610                 615                 620
Pro Pro Gly Phe Gln Gly Leu Gln Ala Ser Pro Ser Lys His Ala Gly
625                 630                 635                 640
Tyr Ser Val Arg Met Glu Asn Ala Val Pro Ile Val Thr Gln Ala Pro
                645                 650                 655
Gly Ala Gln Pro Leu Gln Ile Gln Pro Gly Leu Leu Ala Gln Gln Ala
            660                 665                 670
Trp Pro Gly Gly Ala Gln Gln Ile Leu Leu Pro Pro Ala Trp Gln Gln
        675                 680                 685
```

-continued

```
Leu Thr Gly Val Ala Thr His Thr Ser Val Gln His Ala Val Ile
    690             695                 700
Pro Glu Thr Met Ala Gly Thr Gln Gln Leu Ala Asp Trp Arg Asn Thr
705                 710                 715                 720
His Ala His Gly Ser His Tyr Asn Pro Ile Met Gln Gln Pro Thr Leu
                725                 730                 735
Leu Thr Gly His Val Thr Leu Pro Ala Ala Gln Pro Leu Asn Val Gly
            740                 745                 750
Val Ala His Val Met Arg Gln Gln Pro Thr Ser Thr Ser Ser Arg
        755                 760                 765
Lys Ser Lys Gln His Gln Pro Ser Met Arg Asn Val Ser Thr Cys Glu
770                 775                 780
Val Thr Ser Ser Gln Ser Thr Ser Ser Pro Gln Arg Ser Lys Arg Val
785                 790                 795                 800
Lys Glu Asn Thr Pro Pro Arg Cys Ala Met Val His Ser Ser Pro Ala
                805                 810                 815
Cys Ser Thr Ser Val Thr Cys Gly Trp Gly Asp Val Ala Ser Ser Thr
                820                 825                 830
Thr Arg Glu Arg Gln Arg Gln Thr Ile Val Ile Pro Asp Thr Pro Ser
        835                 840                 845
Pro Thr Val Ser Val Ile Thr Ile Ser Ser Asp Thr Asp Glu Glu
    850                 855                 860
Glu Gln Lys His Ala Pro Thr Ser Thr Val Ser Lys Gln Arg Lys Asn
865                 870                 875                 880
Val Ile Ser Cys Val Thr Val His Asp Ser Pro Tyr Ser Asp Ser Ser
                885                 890                 895
Ser Asn Thr Ser Pro Tyr Ser Val Gln Gln Arg Thr Gly His Asn Gly
                900                 905                 910
Thr Asn Thr Leu Asp Thr Lys Gly Ala Leu Glu Asn His Cys Thr Gly
            915                 920                 925
Asn Pro Arg Thr Ile Ile Val Pro Pro Leu Lys Thr Gln Ala Ser Glu
    930                 935                 940
Val Leu Val Glu Cys Asp Ser Leu Gly Pro Ala Val Ser Thr Gly His
945                 950                 955                 960
His Ser Ser Ser Phe Lys Cys Lys Ser Ser Thr Val Thr Ser Thr
                965                 970                 975
Ser Gly His Ser Ser Gly Ser Ser Ser Gly Ala Ile Ala Tyr Arg Gln
            980                 985                 990
Gln Arg Pro Gly Pro His Phe Gln Gln Gln Gln Pro Leu Asn Leu Ser
        995                 1000                1005
Gln Ala Gln Pro His Met Ala Thr Asp Arg Thr Gly Ser His Arg
    1010                1015                1020
Arg Gln Gln Ala Tyr Ile Thr Pro Thr Met Ala Gln Ala Pro Tyr
    1025                1030                1035
Thr Phe Pro His Asn Ser Pro Ser His Gly Thr Val His Pro His
    1040                1045                1050
Leu Ala Ala Ala Ala His Leu Pro Thr Gln Pro His Leu Tyr Thr
    1055                1060                1065
Tyr Thr Ala Pro Thr Ala Leu Gly Ser Thr Gly Thr Val Ala His
    1070                1075                1080
Leu Val Ala Ser Gln Gly Ser Ala Arg His Thr Val Gln His Thr
    1085                1090                1095
```

```
Ala Tyr Pro Ala Ser Ile Val His Gln Val Pro Val Ser Met Gly
    1100            1105            1110

Pro Arg Val Leu Pro Ser Pro Thr Ile His Pro Ser Gln Tyr Pro
    1115            1120            1125

Ala Gln Phe Ala His Gln Thr Tyr Ile Ser Ala Ser Pro Ala Ser
    1130            1135            1140

Thr Val Tyr Thr Gly Tyr Pro Leu Ser Pro Ala Lys Val Asn Gln
1145            1150            1155

Tyr Pro Tyr Ile
    1160

<210> SEQ ID NO 4
<211> LENGTH: 1198
<212> TYPE: PRT
<213> ORGANISM: Homo sapiens

<400> SEQUENCE: 4

Met Ala Pro Val Tyr Glu Gly Met Ala Ser His Val Gln Val Phe Ser
1               5                   10                  15

Pro His Thr Leu Gln Ser Ser Ala Phe Cys Ser Val Lys Lys Leu Lys
                20                  25                  30

Val Glu Pro Ser Ser Asn Trp Asp Met Thr Gly Tyr Gly Ser His Ser
            35                  40                  45

Lys Val Tyr Ser Gln Ser Lys Asn Ile Pro Pro Ser Gln Pro Ala Ser
    50                  55                  60

Thr Thr Val Ser Thr Ser Leu Pro Val Pro Asn Pro Ser Leu Pro Tyr
65                  70                  75                  80

Glu Gln Thr Ile Val Phe Pro Gly Ser Thr Gly His Ile Val Val Thr
                85                  90                  95

Ser Ala Ser Ser Thr Ser Val Thr Gly Gln Val Leu Gly Gly Pro His
            100                 105                 110

Asn Leu Met Arg Arg Ser Thr Val Ser Leu Leu Asp Thr Tyr Gln Lys
        115                 120                 125

Cys Gly Leu Lys Arg Lys Ser Glu Glu Ile Glu Asn Thr Ser Ser Val
130                 135                 140

Gln Ile Ile Glu Glu His Pro Pro Met Ile Gln Asn Asn Ala Ser Gly
145                 150                 155                 160

Ala Thr Val Ala Thr Ala Thr Ser Thr Ala Thr Ser Lys Asn Ser
                165                 170                 175

Gly Ser Asn Ser Glu Gly Asp Tyr Gln Leu Val Gln His Glu Val Leu
            180                 185                 190

Cys Ser Met Thr Asn Thr Tyr Glu Val Leu Glu Phe Leu Gly Arg Gly
        195                 200                 205

Thr Phe Gly Gln Val Val Lys Cys Trp Lys Arg Gly Thr Asn Glu Ile
    210                 215                 220

Val Ala Ile Lys Ile Leu Lys Asn Arg Pro Ser Tyr Ala Arg Gln Gly
225                 230                 235                 240

Gln Ile Glu Val Ser Ile Leu Ala Arg Leu Ser Thr Glu Ser Ala Asp
                245                 250                 255

Asp Tyr Asn Phe Val Arg Ala Tyr Glu Cys Phe Gln His Lys Asn His
            260                 265                 270

Thr Cys Leu Val Phe Glu Met Leu Glu Gln Asn Leu Tyr Asp Phe Leu
        275                 280                 285

Lys Gln Asn Lys Phe Ser Pro Leu Pro Leu Lys Tyr Ile Arg Pro Val
    290                 295                 300
```

-continued

```
Leu Gln Gln Val Ala Thr Ala Leu Met Lys Leu Lys Ser Leu Gly Leu
305                 310                 315                 320

Ile His Ala Asp Leu Lys Pro Glu Asn Ile Met Leu Val Asp Pro Ser
                325                 330                 335

Arg Gln Pro Tyr Arg Val Lys Val Ile Asp Phe Gly Ser Ala Ser His
            340                 345                 350

Val Ser Lys Ala Val Cys Ser Thr Tyr Leu Gln Ser Arg Tyr Tyr Arg
        355                 360                 365

Ala Pro Glu Ile Ile Leu Gly Leu Pro Phe Cys Glu Ala Ile Asp Met
370                 375                 380

Trp Ser Leu Gly Cys Val Ile Ala Glu Leu Phe Leu Gly Trp Pro Leu
385                 390                 395                 400

Tyr Pro Gly Ala Ser Glu Tyr Asp Gln Ile Arg Tyr Ile Ser Gln Thr
                405                 410                 415

Gln Gly Leu Pro Ala Glu Tyr Leu Leu Ser Ala Gly Thr Lys Thr Thr
            420                 425                 430

Arg Phe Phe Asn Arg Asp Thr Asp Ser Pro Tyr Pro Leu Trp Arg Leu
        435                 440                 445

Lys Thr Pro Asp Asp His Glu Ala Glu Thr Gly Ile Lys Ser Lys Glu
450                 455                 460

Ala Arg Lys Tyr Ile Phe Asn Cys Leu Asp Asp Met Ala Gln Val Asn
465                 470                 475                 480

Met Thr Thr Asp Leu Glu Gly Ser Asp Met Leu Val Glu Lys Ala Asp
                485                 490                 495

Arg Arg Glu Phe Ile Asp Leu Leu Lys Lys Met Leu Thr Ile Asp Ala
            500                 505                 510

Asp Lys Arg Ile Thr Pro Ile Glu Thr Leu Asn His Pro Phe Val Thr
        515                 520                 525

Met Thr His Leu Leu Asp Phe Pro His Ser Thr His Val Lys Ser Cys
530                 535                 540

Phe Gln Asn Met Glu Ile Cys Lys Arg Arg Val Asn Met Tyr Asp Thr
545                 550                 555                 560

Val Asn Gln Ser Lys Thr Pro Phe Ile Thr His Val Ala Pro Ser Thr
                565                 570                 575

Ser Thr Asn Leu Thr Met Thr Phe Asn Asn Gln Leu Thr Thr Val His
            580                 585                 590

Asn Gln Ala Pro Ser Ser Thr Ser Ala Thr Ile Ser Leu Ala Asn Pro
        595                 600                 605

Glu Val Ser Ile Leu Asn Tyr Pro Ser Thr Leu Tyr Gln Pro Ser Ala
610                 615                 620

Ala Ser Met Ala Ala Val Ala Gln Arg Ser Met Pro Leu Gln Thr Gly
625                 630                 635                 640

Thr Ala Gln Ile Cys Ala Arg Pro Asp Pro Phe Gln Gln Ala Leu Ile
                645                 650                 655

Val Cys Pro Pro Gly Phe Gln Gly Leu Gln Ala Ser Pro Ser Lys His
            660                 665                 670

Ala Gly Tyr Ser Val Arg Met Glu Asn Ala Val Pro Ile Val Thr Gln
        675                 680                 685

Ala Pro Gly Ala Gln Pro Leu Gln Ile Gln Pro Gly Leu Leu Ala Gln
690                 695                 700

Gln Ala Trp Pro Ser Gly Thr Gln Gln Ile Leu Leu Pro Pro Ala Trp
705                 710                 715                 720
```

-continued

```
Gln Gln Leu Thr Gly Val Ala Thr His Thr Ser Val Gln His Ala Thr
            725                 730                 735
Val Ile Pro Glu Thr Met Ala Gly Thr Gln Gln Leu Ala Asp Trp Arg
            740                 745                 750
Asn Thr His Ala His Gly Ser His Tyr Asn Pro Ile Met Gln Gln Pro
            755                 760                 765
Ala Leu Leu Thr Gly His Val Thr Leu Pro Ala Ala Gln Pro Leu Asn
770                 775                 780
Val Gly Val Ala His Val Met Arg Gln Gln Pro Thr Ser Thr Thr Ser
785                 790                 795                 800
Ser Arg Lys Ser Lys Gln His Gln Ser Ser Val Arg Asn Val Ser Thr
            805                 810                 815
Cys Glu Val Ser Ser Ser Gln Ala Ile Ser Ser Pro Gln Arg Ser Lys
            820                 825                 830
Arg Val Lys Glu Asn Thr Pro Pro Arg Cys Ala Met Val His Ser Ser
            835                 840                 845
Pro Ala Cys Ser Thr Ser Val Thr Cys Gly Trp Gly Asp Val Ala Ser
850                 855                 860
Ser Thr Thr Arg Glu Arg Gln Arg Gln Thr Ile Val Ile Pro Asp Thr
865                 870                 875                 880
Pro Ser Pro Thr Val Ser Val Ile Thr Ile Ser Ser Asp Thr Asp Glu
            885                 890                 895
Glu Glu Glu Gln Lys His Ala Pro Thr Ser Thr Val Ser Lys Gln Arg
            900                 905                 910
Lys Asn Val Ile Ser Cys Val Thr Val His Asp Ser Pro Tyr Ser Asp
            915                 920                 925
Ser Ser Ser Asn Thr Ser Pro Tyr Ser Val Gln Gln Arg Ala Gly His
930                 935                 940
Asn Asn Ala Asn Ala Phe Asp Thr Lys Gly Ser Leu Glu Asn His Cys
945                 950                 955                 960
Thr Gly Asn Pro Arg Thr Ile Ile Val Pro Pro Leu Lys Thr Gln Ala
            965                 970                 975
Ser Glu Val Leu Val Glu Cys Asp Ser Leu Val Pro Val Asn Thr Ser
            980                 985                 990
His His Ser Ser Ser Tyr Lys Ser  Lys Ser Ser Ser Asn  Val Thr Ser
            995                 1000                1005
Thr Ser  Gly His Ser Ser Gly  Ser Ser Ser Gly Ala  Ile Thr Tyr
1010                1015                1020
Arg Gln  Gln Arg Pro Gly Pro  His Phe Gln Gln Gln  Gln Pro Leu
1025                1030                1035
Asn Leu  Ser Gln Ala Gln Gln  His Ile Thr Thr Asp  Arg Thr Gly
1040                1045                1050
Ser His  Arg Arg Gln Gln Ala  Tyr Ile Thr Pro Thr  Met Ala Gln
1055                1060                1065
Ala Pro  Tyr Ser Phe Pro His  Asn Ser Pro Ser His  Gly Thr Val
1070                1075                1080
His Pro  His Leu Ala Ala Ala  Ala Ala Ala His  Leu Pro Thr
1085                1090                1095
Gln Pro  His Leu Tyr Thr Tyr  Thr Ala Pro Ala Ala  Leu Gly Ser
1100                1105                1110
Thr Gly  Thr Val Ala His Leu  Val Ala Ser Gln Gly  Ser Ala Arg
1115                1120                1125
His Thr  Val Gln His Thr Ala  Tyr Pro Ala Ser Ile  Val His Gln
```

-continued

```
                    1130                1135                1140
Val Pro Val Ser Met Gly Pro Arg Val Leu Pro Ser Pro Thr Ile
    1145                1150                1155

His Pro Ser Gln Tyr Pro Ala Gln Phe Ala His Gln Thr Tyr Ile
    1160                1165                1170

Ser Ala Ser Pro Ala Ser Thr Val Tyr Thr Gly Tyr Pro Leu Ser
    1175                1180                1185

Pro Ala Lys Val Asn Gln Tyr Pro Tyr Ile
    1190                1195
```

<210> SEQ ID NO 5
<211> LENGTH: 1371
<212> TYPE: DNA
<213> ORGANISM: Homo sapiens

<400> SEQUENCE: 5

```
agcggagagc cgactcaaca gcgctggaac ccattcggtg gggcctgggg cccctcatcc    60
caagccagga gggtttctgg ggaggggtgc agccctggc agactgacag tgtggcctgg   120
gggtttgggg gtgccaggga agcagggcc aacctcatag gaggagacac gagtgcggtt   180
ctctttcccc cactgggggg cctgctgtgt cagcagccag gcgggaggcc tgggcggcag   240
agccagtggt acaggggcct gggcaggcg gtgtctggca gcagcggcac catgtccacc   300
atccagtcgg agactgactg ctacgacatc atcgaggtct gggcaagggg gaccttcggg   360
gaggtagcca agggctggcg gcggagcacg ggcgagatgg tggccatcaa gatcctcaag   420
aatgacgcct accgcaaccg catcatcaag aacgagctga agctgctgca ctgcatgcga   480
ggcctagacc ctgaagaggc ccacgtcatc cgcttccttg agttcttcca tgacgccctc   540
aagttctacc tggtctttga gctgctggag caaaaccttt cgagttcca aaggagaac    600
aacttcgcgc ccctccccgc ccgccacatc cgtacagtca ccctgcaggt gctcacagcc   660
ctggcccggc tcaaggagct ggctatcatc cacgctgatc tcaagcctga aacatcatg    720
ctggtggacc agacccgctg ccccttcagg gtcaaggtga ttgacttcgg atccgccagc   780
atttcagcg aggtgcgcta cgtgaaggag ccatacatcc agtcgcgctt ctaccgggcc   840
cctgagatcc tgctggggct gcccttctgc gagaaggtgg acgtgtggtc cctgggctgc   900
gtcatggctg agctgcacct gggctggcct ctctaccccg caacaacga gtacgaccag   960
gtgcgctaca tctgcgaaac ccagggcctg cccaagccac acctgttgca cgccgcctgc  1020
aaggcccacc acttcttcaa gcgcaacccc caccctgacg ctgccaaccc ctggcagctc  1080
aagtcctcgg ctgactacct ggccgagacg aaggtgcgcc cattggagcg ccgcaagtat  1140
atgctcaagt cgttggacca gattgagaca gtgaatggtg gcagtgtggc cagtcggcta  1200
accttccctg accgggaggc gctggcggag cacgccgacc tcaagagcat ggtggagctg  1260
atcaagcgca tgctgacctg ggagtcacac gaacgcatca gccccagtgc tgccctgcgc  1320
caccccttcg tgtccatgca gcagctgcgc agtgcccacg agaccaccca c           1371
```

<210> SEQ ID NO 6
<211> LENGTH: 457
<212> TYPE: PRT
<213> ORGANISM: Homo sapiens

<400> SEQUENCE: 6

```
Ser Gly Glu Pro Thr Gln Gln Arg Trp Asn Pro Phe Gly Gly Ala Trp
1               5                   10                  15
```

-continued

Gly Pro Ser Ser Gln Ala Arg Arg Val Ser Gly Glu Gly Cys Ser Pro
             20                  25                  30

Trp Gln Thr Asp Ser Val Ala Trp Gly Phe Gly Gly Ala Arg Glu Ala
         35                  40                  45

Gly Ala Asn Leu Ile Gly Gly Asp Thr Ser Ala Val Leu Phe Pro Pro
50                  55                  60

Leu Gly Leu Leu Cys Gln Gln Pro Gly Gly Arg Pro Gly Arg Gln
65              70                  75                  80

Ser Gln Trp Tyr Arg Gly Leu Gly Arg Ala Val Ser Gly Ser Ser Gly
                 85                  90                  95

Thr Met Ser Thr Ile Gln Ser Glu Thr Asp Cys Tyr Asp Ile Ile Glu
             100                 105                 110

Val Leu Gly Lys Gly Thr Phe Gly Glu Val Ala Lys Gly Trp Arg Arg
         115                 120                 125

Ser Thr Gly Glu Met Val Ala Ile Lys Ile Leu Lys Asn Asp Ala Tyr
130                 135                 140

Arg Asn Arg Ile Ile Lys Asn Glu Leu Lys Leu Leu His Cys Met Arg
145                 150                 155                 160

Gly Leu Asp Pro Glu Glu Ala His Val Ile Arg Phe Leu Glu Phe Phe
                 165                 170                 175

His Asp Ala Leu Lys Phe Tyr Leu Val Phe Glu Leu Leu Glu Gln Asn
             180                 185                 190

Leu Phe Glu Phe Gln Lys Glu Asn Asn Phe Ala Pro Leu Pro Ala Arg
         195                 200                 205

His Ile Arg Thr Val Thr Leu Gln Val Leu Thr Ala Leu Ala Arg Leu
     210                 215                 220

Lys Glu Leu Ala Ile Ile His Ala Asp Leu Lys Pro Glu Asn Ile Met
225                 230                 235                 240

Leu Val Asp Gln Thr Arg Cys Pro Phe Arg Val Lys Val Ile Asp Phe
                 245                 250                 255

Gly Ser Ala Ser Ile Phe Ser Glu Val Arg Tyr Val Lys Glu Pro Tyr
             260                 265                 270

Ile Gln Ser Arg Phe Tyr Arg Ala Pro Glu Ile Leu Leu Gly Leu Pro
         275                 280                 285

Phe Cys Glu Lys Val Asp Val Trp Ser Leu Gly Cys Val Met Ala Glu
290                 295                 300

Leu His Leu Gly Trp Pro Leu Tyr Pro Gly Asn Asn Glu Tyr Asp Gln
305                 310                 315                 320

Val Arg Tyr Ile Cys Glu Thr Gln Gly Leu Pro Lys Pro His Leu Leu
             325                 330                 335

His Ala Ala Cys Lys Ala His His Phe Phe Lys Arg Asn Pro His Pro
         340                 345                 350

Asp Ala Ala Asn Pro Trp Gln Leu Lys Ser Ser Ala Asp Tyr Leu Ala
     355                 360                 365

Glu Thr Lys Val Arg Pro Leu Glu Arg Arg Lys Tyr Met Leu Lys Ser
370                 375                 380

Leu Asp Gln Ile Glu Thr Val Asn Gly Gly Ser Val Ala Ser Arg Leu
385                 390                 395                 400

Thr Phe Pro Asp Arg Glu Ala Leu Ala Glu His Ala Asp Leu Lys Ser
                 405                 410                 415

Met Val Glu Leu Ile Lys Arg Met Leu Thr Trp Glu Ser His Glu Arg
             420                 425                 430

Ile Ser Pro Ser Ala Ala Leu Arg His Pro Phe Val Ser Met Gln Gln

```
                435                 440                 445
Leu Arg Ser Ala His Glu Thr Thr His
    450                 455

<210> SEQ ID NO 7
<211> LENGTH: 254
<212> TYPE: DNA
<213> ORGANISM: Homo sapiens

<400> SEQUENCE: 7
ctgagaagtc ggtacatgtg gtgccacagc aggagtgccc aggccctagc cctgcacaat      60
ggtcaaccct gccccttct  ccatgccccg ccaggtgcgc ccattggagc gccgaaagta     120
tatgctcaag tcgttggacc agattgagac agtgcatggt ggcagtgtgg ccagtcggct     180
aaccttccct gaccggggag gcgctggcgg acacacgccg acctcaagag catggtagac     240
ctgagcaagc cagg                                                       254

<210> SEQ ID NO 8
<211> LENGTH: 374
<212> TYPE: DNA
<213> ORGANISM: Homo sapiens

<400> SEQUENCE: 8
cacgaggccc agctccaaaa aaaaaaaga aagaaagaaa tctggtacaa gaggaaaaac       60
tggagaattg aagcagcaag agagcttcaa gtcagatcat gggcagaagc agggcaata     120 ctatttggct cccacaacag gtgattttgg gagccctgag tccagataca tgtccggctg     180
gtgtctccca caccccacca ggtacgccca ctggagcgcc gcaagtacat gctcaaatcc     240
ttggaccaaa ttgagacggt gaatggtggc ggcgctgtga atcggttgag ttttccagac     300
cgggaggcac tggctggaac acgcggacct caagagcatg gtggagctga ttaaacgcat     360
gctgacatgg gagt                                                      374

<210> SEQ ID NO 9
<211> LENGTH: 806
<212> TYPE: DNA
<213> ORGANISM: Homo sapiens

<400> SEQUENCE: 9
agcggatcat cccaagccag gagggtttct ggggaggggt gcagcccctg gcagactgac       60
agtgtggcct gggggtttgg gggtgccagg gaagcagggg ccaacctcat aggaggagac     120
acgagtgcgg ttctctttcc cccactgggg ggcctgctgt gtcagcagcc aggcgggagg     180
cctgggcggc agagccagtg gtacaggggc ctggcaggg cggtgtctgg cagcagcggc      240
accatgtcca ccatccagtc ggagactgac tgctacgaca tcatcgaggt cttgggcaag     300 gggacctteg gggaggtagc caagggctgg cggcggagca cgggcgagat ggtggccatc     360
aagatcctca gaatgacgc ctaccgcaac cgcatcatca gaacgagct gaagctgctg      420 cactgcatgc gaggcctaga ccctgaagag gcccacgtca tccgcttcct tgagttcttc     480
catgacgccc tcaagttcta cctggtcttt gagctgctgg agcaaaacct tttcgagttc     540
cagaaggaga caactttcg gcgcccctcc ccgcccgcca catccgtaca gtcaccctgc     600
aggtgctcac agccctggcc cggctcaagg agctggctat catccacgct gatctcaagg     660
cctgagaaca tcatgctggt ggaccagacc cgctgcccc ttcagggtca aggtgattga      720
cttcggatcc ggcagcattt tcagcgaggt gcgctacgtg aaggagccat aaatcaggtc     780
```

```
                                                -continued gagcttctac acggggccct gagatc                                           806

<210> SEQ ID NO 10
<211> LENGTH: 605
<212> TYPE: DNA
<213> ORGANISM: Homo sapiens

<400> SEQUENCE: 10
agcggagagc cactcaacag cgctggaacc cattcggtgg ggcctggggc ccctcatccc       60
aagccaggag ggtttctggg gaggggtgca gcccctggca gactgacagt gtggcctggg      120
ggtttggggg tgccagggaa gcaggggcca acctcatagg aggagacacg agtgcggttc      180
tctttccccc actgggggc ctgctgtgtc agcagccagg cgggaggcct gggcggcaga       240
gccagtggta caggggcctg gcagggcgg tgtctggcag cagcggcacc atgtccacca       300
tccagtcgga gactgactgc tacgacatca tcgaggtctt gggcaagggg accttcgggg      360
caggtagcca agggctggcg gcggagcacg ggcgagatgg tggccatcaa gatcctcaag      420
actgacgcct accgcaaccg catcatcaaa acacgagctg aagctgctgc actgcatgcg      480
aggcctagac cctgaccgac ggcccacgtc atccgcttcc ttgagttctt ccatgacgcc      540
ctcaagttct acctggtctt cgagctgctg agcaaaaacc tttccgagtt ccagaaggag      600
aacaa                                                                  605

<210> SEQ ID NO 11
<211> LENGTH: 605
<212> TYPE: DNA
<213> ORGANISM: Homo sapiens

<400> SEQUENCE: 11
agcggactca acagcgctgg aacccattcg gtggggcctg ggcccctca tcccaagcca       60 ggagggtttc tggggagggg tgcagcccct ggcagactga cagtgtggcc tgggggtttg      120
ggggtgccag gaagcagggg ccaacctcat aggaggagac acgagtgcgg ttctctttcc      180
cccactgggg ggcctgctgt gtcagcagcc aggcgggagg cctgggcggc agagccagtg      240
gtacaggcgc ctgggcaggg cggtgtctgg cagcagcggc accatgtcca ccatccagtc      300
ggagactgac tgctacgaca tcatcgaggt cttgggcaag gggaccttcg ggaggtagc      360 caagggctgg cggcggagca cgggcgagat ggtggccatc aagatcctca gaatgacgc      420 ctaccgcaac cgcgatcatc aagaacgagc tgaagctgct gcactgcatg cgaggcctag      480
accctgaaga ggcccacgtc atccgcttcc ttgagttctt ccatgacgcc ctcaagttct      540
acctggtctt tgagctgctg agcaaaaagc ttttcgagtt ccagaaggag aacaaccttg      600
ggccc                                                                  605

<210> SEQ ID NO 12
<211> LENGTH: 483
<212> TYPE: PRT
<213> ORGANISM: Homo sapiens

<400> SEQUENCE: 12

Met Ser Gly Gly Gly Pro Ser Gly Gly Pro Gly Gly Ser Gly Arg
 1               5                  10                  15

Ala Arg Thr Ser Ser Phe Ala Glu Pro Gly Gly Gly Gly Gly Gly
                20                  25                  30

Gly Gly Gly Pro Gly Gly Ser Ala Ser Gly Pro Gly Gly Thr Gly Gly
                35                  40                  45
```

```
Gly Lys Ala Ser Val Gly Ala Met Gly Gly Gly Val Gly Ala Ser Ser
 50                  55                  60

Ser Gly Gly Gly Pro Gly Gly Ser Gly Gly Gly Ser Gly Gly Pro
 65                  70                  75                  80

Gly Ala Gly Thr Ser Phe Pro Pro Gly Val Lys Leu Gly Arg Asp
                 85                  90                  95

Ser Gly Lys Val Thr Thr Val Ala Thr Leu Gly Gln Gly Pro Glu
            100                 105                 110

Arg Ser Gln Glu Val Ala Tyr Thr Asp Ile Lys Val Ile Gly Asn Gly
            115                 120                 125

Ser Phe Gly Val Val Tyr Gln Ala Arg Leu Ala Glu Thr Arg Glu Leu
            130                 135                 140

Val Ala Ile Lys Lys Val Leu Gln Asp Lys Arg Phe Lys Asn Arg Glu
145                 150                 155                 160

Leu Gln Ile Met Arg Lys Leu Asp His Cys Asn Ile Val Arg Leu Arg
                165                 170                 175

Tyr Phe Phe Tyr Ser Ser Gly Glu Lys Lys Asp Glu Leu Tyr Leu Asn
                180                 185                 190

Leu Val Leu Glu Tyr Val Pro Glu Thr Val Tyr Arg Val Ala Arg His
                195                 200                 205

Phe Thr Lys Ala Lys Leu Thr Ile Pro Ile Leu Tyr Val Lys Val Tyr
210                 215                 220

Met Tyr Gln Leu Phe Arg Ser Leu Ala Tyr Ile His Ser Gln Gly Val
225                 230                 235                 240

Cys His Arg Asp Ile Lys Pro Gln Asn Leu Leu Val Asp Pro Asp Thr
                245                 250                 255

Ala Val Leu Lys Leu Cys Asp Phe Gly Ser Ala Lys Gln Leu Val Arg
                260                 265                 270

Gly Glu Pro Asn Val Ser Tyr Ile Cys Ser Arg Tyr Tyr Arg Ala Pro
                275                 280                 285

Glu Leu Ile Phe Gly Ala Thr Asp Tyr Thr Ser Ser Ile Asp Val Trp
                290                 295                 300

Ser Ala Gly Cys Val Leu Ala Glu Leu Leu Leu Gly Gln Pro Ile Phe
305                 310                 315                 320

Pro Gly Asp Ser Gly Val Asp Gln Leu Val Glu Ile Ile Lys Val Leu
                325                 330                 335

Gly Thr Pro Thr Arg Glu Gln Ile Arg Glu Met Asn Pro Asn Tyr Thr
                340                 345                 350

Glu Phe Lys Phe Pro Gln Ile Lys Ala His Pro Trp Thr Lys Val Phe
                355                 360                 365

Lys Ser Arg Thr Pro Pro Glu Ala Ile Ala Leu Cys Ser Ser Leu Leu
370                 375                 380

Glu Tyr Thr Pro Ser Ser Arg Leu Ser Pro Leu Glu Ala Cys Ala His
385                 390                 395                 400

Ser Phe Phe Asp Glu Leu Arg Cys Leu Gly Thr Gln Leu Pro Asn Asn
                405                 410                 415

Arg Pro Leu Pro Pro Leu Phe Asn Phe Ser Ala Gly Glu Leu Ser Ile
                420                 425                 430

Gln Pro Ser Leu Asn Ala Ile Leu Ile Pro Pro His Leu Arg Ser Pro
                435                 440                 445

Ala Gly Thr Thr Thr Leu Thr Pro Ser Ser Gln Ala Leu Thr Glu Thr
                450                 455                 460

Pro Thr Ser Ser Asp Trp Gln Ser Thr Asp Ala Thr Pro Thr Leu Thr
```

-continued

```
         465                 470                 475                 480

Asn Ser Ser

<210> SEQ ID NO 13
<211> LENGTH: 22
<212> TYPE: DNA
<213> ORGANISM: Homo sapiens
<220> FEATURE:
<221> NAME/KEY: misc_feature
<223> OTHER INFORMATION: forward primer

<400> SEQUENCE: 13
agacagtgaa tggtggcagt gt                                              22

<210> SEQ ID NO 14
<211> LENGTH: 20
<212> TYPE: DNA
<213> ORGANISM: Homo sapiens
<220> FEATURE:
<221> NAME/KEY: misc_feature
<223> OTHER INFORMATION: Reverse primer

<400> SEQUENCE: 14
gctgatgcgt tcgtgtgact                                                 20
```

US 7,049,118 B2

REGULATION OF HUMAN SERINE-THREONINE PROTEIN KINASE

This application is a National Stage application of now abandoned PCT application PCT/EP01/15320 filed Dec. 27, 2001, which was published in English under PCT Article 21(2) on Jul. 11, 2002, which claims the benefit of U.S. provisional application Ser. No. 60/259,215 filed Jan. 3, 2001, Ser. No. 60/306,468 filed Jul. 20, 2001, and Ser. No. 60/308,098 filed Jul. 30, 2001. These applications are incorporated herein by reference in their entireties.

This application incorporates by reference now abandoned U.S. provisional application Ser. No. 60/259,215 filed Jan. 3, 2001, Ser. No. 60/306,468 filed Jul. 20, 2001 and Ser. No. 60/308,098 filed Jul. 30, 2001.

TECHNICAL FIELD OF THE INVENTION

The invention relates to the regulation of human serine-threonine protein kinase.

BACKGROUND OF THE INVENTION

Intercellular signaling regulates a variety of important biological functions. For example, transforming growth factor type beta (TGF-β) regulates the proliferation and differentiation of a variety of cell types binding to and activating cell surface receptors which possess serine-threonine kinase activity. Atfi et al. (*Proc. Natl. Acad. Sci. U.S.A.* 92, 12110–04, 1995) have shown that TGF-β activates a 78-kDa protein (p78) serine/threonine kinase; the p78 kinase was activated only in cells for which TGF-β acts as a growth inhibitory factor. Because of the important functions of kinases such as p78, there is a need in the art to identify new kinases and methods of regulating these new kinases for therapeutic effects.

SUMMARY OF THE INVENTION

It is an object of the invention to provide reagents and methods of regulating a human serine-threonine protein kinase. This and other objects of the invention are provided by one or more of the embodiments described below.

One embodiment of the invention is a serine-threonine protein kinase polypeptide comprising an amino acid sequence selected from the group consisting of:
amino acid sequences which are at least about 51% identical to the amino acid sequence shown in SEQ ID NO: 2;
the amino acid sequence shown in SEQ ID NO: 2;
amino acid sequences which are at least about 51% identical to the amino acid sequence shown in SEQ ID NO: 6; and
the amino acid sequence shown in SEQ ID NO: 6.

Yet another embodiment of the invention is a method of screening for agents which decrease extracellular matrix degradation. A test compound is contacted with a serine-threonine protein kinase polypeptide comprising an amino acid sequence selected from the group consisting of:
amino acid sequences which are at least about 51% identical to the amino acid sequence shown in SEQ ID NO: 2;
the amino acid sequence shown in SEQ ID NO: 2;
amino acid sequences which are at least about 51% identical to the amino acid sequence shown in SEQ ID NO: 6; and
the amino acid sequence shown in SEQ ID NO: 6.

Binding between the test compound and the serine-threonine protein kinase polypeptide is detected. A test compound which binds to the serine-threonine protein kinase polypeptide is thereby identified as a potential agent for decreasing extra-cellular matrix degradation. The agent can work by decreasing the activity of the serine-threonine protein kinase.

Another embodiment of the invention is a method of screening for agents which decrease extracellular matrix degradation. A test compound is contacted with a polynucleotide encoding a serine-threonine protein kinase polypeptide, wherein the polynucleotide comprises a nucleotide sequence selected from the group consisting of:
nucleotide sequences which are at least about 50% identical to the nucleotide sequence shown in SEQ ID NO: 1;
the nucleotide sequence shown in SEQ ID NO: 1;
nucleotide sequences which are at least about 50% identical to the nucleotide sequence shown in SEQ ID NO: 5; and
the nucleotide sequence shown in SEQ ID NO: 5.

Binding of the test compound to the polynucleotide is detected. A test compound which binds to the polynucleotide is identified as a potential agent for decreasing extracellular matrix degradation. The agent can work by decreasing the amount of the serine-threonine protein kinase through interacting with the serine-threonine protein kinase mRNA.

Another embodiment of the invention is a method of screening for agents which regulate extracellular matrix degradation. A test compound is contacted with a serine-threonine protein kinase polypeptide comprising an amino acid sequence selected from the group consisting of:
amino acid sequences which are at least about 51% identical to the amino acid sequence shown in SEQ ID NO: 2;
the amino acid sequence shown in SEQ ID NO: 2;
amino acid sequences which are at least about 51% identical to the amino acid sequence shown in SEQ ID NO: 6; and
the amino acid sequence shown in SEQ ID NO: 6.

A serine-threonine protein kinase activity of the polypeptide is detected. A test compound which increases serine-threonine protein kinase activity of the polypeptide relative to serine-threonine protein kinase activity in the absence of the test compound is thereby identified as a potential agent for increasing extracellular matrix degradation. A test compound which decreases serine-threonine protein kinase activity of the polypeptide relative to serine-threonine protein kinase activity in the absence of the test compound is thereby identified as a potential agent for decreasing extra-cellular matrix degradation.

Even another embodiment of the invention is a method of screening for agents which decrease extracellular matrix degradation. A test compound is contacted with a serine-threonine protein kinase product of a polynucleotide which comprises a nucleotide sequence selected from the group consisting of:
nucleotide sequences which are at least about 50% identical to the nucleotide sequence shown in SEQ ID NO: 1;
the nucleotide sequence shown in SEQ ID NO: 1;
nucleotide sequences which are at least about 50% identical to the nucleotide sequence shown in SEQ ID NO: 5; and
the nucleotide sequence shown in SEQ ID NO: 5.

Binding of the test compound to the serine-threonine protein kinase product is detected. A test compound which binds to the serine-threonine protein kinase product is thereby identified as a potential agent for decreasing extra-cellular matrix degradation.

Still another embodiment of the invention is a method of reducing extracellular matrix degradation. A cell is contacted with a reagent which specifically binds to a polynucleotide encoding a serine-threonine protein kinase polypeptide or the product encoded by the polynucleotide, wherein the polynucleotide comprises a nucleotide sequence selected from the group consisting of:

nucleotide sequences which are at least about 50% identical to the nucleotide sequence shown in SEQ ID NO: 1;
the nucleotide sequence shown in SEQ ID NO: 1;
nucleotide sequences which are at least about 50% identical to the nucleotide sequence shown in SEQ ID NO: 5; and
the nucleotide sequence shown in SEQ ID NO: 5.

Serine-threonine protein kinase activity in the cell is thereby decreased.

The invention thus provides a human serine-threonine protein kinase that can be used to identify test compounds that may act, for example, as activators or inhibitors at the enzyme's active site. Human serine-threonine protein kinase and fragments thereof also are useful in raising specific antibodies that can block the enzyme and effectively reduce its activity.

BRIEF DESCRIPTION OF THE DRAWINGS

FIG. 1 shows the DNA-sequence encoding a serine-threonine protein kinase Poly-peptide (SEQ ID NO: 1).

FIG. 2 shows the amino acid sequence deduced from the DNA-sequence of FIG. 1 (SEQ ID NO: 2).

FIG. 3 shows the amino acid sequence of the protein identified by trembl Accession No. AF144573|144573_1 (SEQ ID NO: 3).

FIG. 4 shows the amino acid sequence of a serine-threonine protein kinase Poly-peptide (SEQ ID NO: 4).

FIG. 5 shows the DNA-sequence encoding a serine-threonine protein kinase Poly-peptide (SEQ ID NO: 5).

FIG. 6 shows the amino acid sequence deduced from the DNA-sequence of FIG. 5 (SEQ ID NO: 6).

FIG. 7 shows the DNA-sequence encoding a serine-threonine protein kinase Poly-peptide (SEQ ID NO: 7).

FIG. 8 shows the DNA-sequence encoding a serine-threonine protein kinase Poly-peptide (SEQ ID NO: 8).

FIG. 9 shows the DNA-sequence encoding a serine-threonine protein kinase Poly-peptide (SEQ ID NO: 9).

FIG. 10 shows the DNA-sequence encoding a serine-threonine protein kinase Poly-peptide (SEQ ID NO: 10).

FIG. 11 shows the DNA-sequence encoding a serine-threonine protein kinase Poly-peptide (SEQ ID NO: 11).

FIG. 12 shows the amino acid sequence of the protein identified by Swissnew Accession No. P49840|KG3A_HUMAN GLYCOGEN SYNTHASE KINASE_3 ALPHA (EC 2.7.1.37) (GSK-3-ALPHA) (SEQ ID NO: 12).

FIG. 13 shows the BLASTP—alignment of SEQ ID NO: 2 against trembl|AF144573|AF144573_1 (SEQ ID NO: 3).

FIG. 14 shows the HMMPFAM—alignment of SEQ ID NO: 2 against pfam|hmm|pkinase.

FIG. 15 shows the BLASTP—alignment of SEQ ID NO: 2 against pdb|1JST|1JST-A.

FIG. 16 shows the Genewise analysis.

FIG. 17 shows the BLASTP—alignment of 426_protc (SEQ ID NO. 6) against swissnew|P49840|KG3A_HUMAN GLYCOGEN SYNTHASE KINASE-3 ALPHA (EC 2.7.1.37) (GSK-3 ALPHA) (SEQ ID NO. 12).

FIG. 18 shows the BLASTP—alignment of 426_protc (SEQ ID NO. 6) against swissnew|Q9H2X6|HIK2_HUMAN HOMEODOMAIN-INTERACTING PROTEIN KINASE 2 (EC 2.7.1.-) SEQ ID NO. 4).

FIG. 19 shows the BLASTP—alignment of 426_protc (SEQ ID NO.6) against pdb|1CM8|1CM8-A.

DETAILED DESCRIPTION OF THE INVENTION

Figure 20:
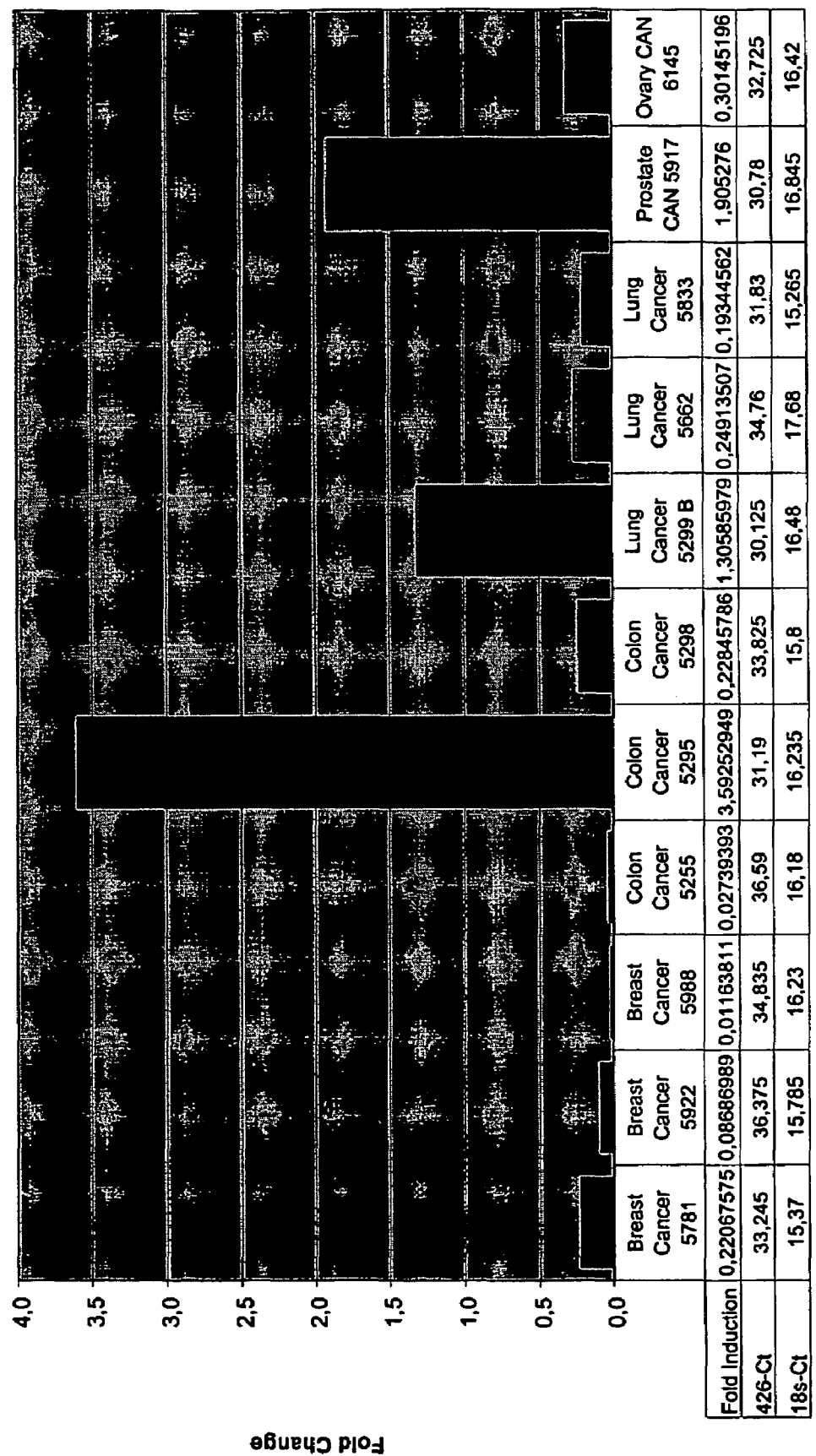
FIG. 20 shows the human serine/threonine kinase relative mRNA expression in cancer tissues.

The invention relates to an isolated polynucleotide being selected from the group consisting of:
a) a polynucleotide encoding a serine-threonine protein kinase polypeptide comprising an amino acid sequence selected from the group consisting of:
  amino acid sequences which are at least about 51% identical to the amino acid sequence shown in SEQ ID NO: 2;
  the amino acid sequence shown in SEQ ID NO: 2;
  amino acid sequences which are at least about 51% identical to the amino acid sequence shown in SEQ ID NO: 6; and
  the amino acid sequence shown in SEQ ID NO: 6.
b) a polynucleotide comprising the sequence of SEQ ID NOS: 1 or 5;
c) a polynucleotide which hybridizes under stringent conditions to a polynucleotide specified in (a) and (b) and encodes a serine-threonine protein kinase polypeptide;
d) a polynucleotide the sequence of which deviates from the polynucleotide sequences specified in (a) to (c) due to the degeneration of the genetic code and encodes a serine-threonine protein kinase polypeptide; and
e) a polynucleotide which represents a fragment, derivative or allelic variation of a polynucleotide sequence specified in (a) to (d) and encodes a serine-threonine protein kinase polypeptide.

Furthermore, it has been discovered by the present applicant that a novel serine-threonine protein kinase, particularly a human serine-threonine protein kinase, can be used in therapeutic methods to treat cancer, diabetes, COPD, or peripheral and central nervous system disorders. Human serine-threonine protein kinase comprises the amino acid sequence shown in SEQ ID NOS: 2 or 6. A coding sequence for human serine-threonine protein kinase is shown in SEQ ID NOS: 1 or 5. This sequence is located on chromosome 19. Related ESTs (SEQ ID NOS: 9–11) are expressed in testis.

Human serine-threonine protein kinase (SEQ ID NO: 2) is 50% identical over 356 amino acids to trembl|AF144573|AF144573_1 (SEQ ID NO: 3), annotated as "Mx-interacting protein kinase PKM" (FIG. 13). Human serine-threonine protein kinase also is 32% identical over 222 amino acids to pdb|1JST|1JST-A, annotated as "cyclin-dependent kinase-2 cyclin fragment" (FIG. 15). HMMP-FAM alignments are shown in FIG. 14. Human serine-threonine protein kinase (SEQ ID NO: 6) is 29% identical over 397 amino acids to swissnew|P49840|KG3A human glycogen synthase kinase-3 alpha (SEQ ID NO: 12) (FIG. 17). Human serine-threonine protein kinase (SEQ ID NO: 6) is 48% identical over 372 amino acids to homeodomain-interacting protein kinase 2 (SEQ ID NO: 4) (FIG. 18).

Human serine-threonine protein kinase of the invention is expected to be useful for the same purposes as previously identified serine-threonine protein kinase enzymes. Human serine-threonine protein kinase is believed to be useful in therapeutic methods to treat disorders such as cancer, diabetes, chronic obstructive pulmonary disease (COPD), and peripheral and central nervous system disorders. Human serine-threonine protein kinase also can be used to screen for human serine-threonine protein kinase activators and inhibitors.

Polypeptides

Human serine-threonine protein kinase polypeptides according to the invention comprise at least 6, 10, 15, 20, 25, 50, 75, 100, 125, 150, 175, 200, 225, 250, 275, 300, 325, 350, or 355 contiguous amino acids selected from the amino acid sequence shown in SEQ ID NO: 2 or a biologically active variant thereof, as defined below. Human serine-threonine protein kinase polypeptides according to the invention comprise at least 6, 10, 15, 20, 25, 50, 75, 100, 125, 150, 175, 200, 225, 250, 275, 300, 325, 350, 375, 400, 425, 450, or 457 contiguous amino acids selected from the amino acid sequence shown in SEQ ID NO: 6 or a biologically active variant thereof, as defined below. A serine-threonine protein kinase polypeptide of the invention therefore can be a portion of a serine-threonine protein kinase protein, a full-length serine-threonine protein kinase protein, or a fusion protein comprising all or a portion of a serine-threonine protein kinase protein.

Biologically Active Variants

Human serine-threonine protein kinase polypeptide variants that are biologically active, e.g., retain a serine-threonine protein kinase activity, also are serine-threonine protein kinase polypeptides. Preferably, naturally or non-naturally occurring serine-threonine protein kinase polypeptide variants have amino acid sequences which are at least about 51, 55, 60, 65, or 70, preferably about 75, 80, 85, 90, 96, 96, 98, or 99% identical to the amino acid sequence shown in SEQ ID NOS: 2 or 6 or a fragment thereof. Percent identity between a putative serine-threonine protein kinase polypeptide variant and an amino acid sequence of SEQ ID NOS: 2 or 6 is determined by conventional methods. See, for example, Altschul et al., Bull. Math. Bio. 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant. The FASTA algorithm is described y Pearson and Lipman, Proc. Nat'l Acad. Sci. USA 85:2444(1988), and by Pearson, Meth. Enzymol. 183:63 (1990). Briefly, FASTA first characterizes sequence similarity by identifying regions shared by the query sequence (e.g. SEQ ID NO: 2, 7 or 8) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to for man approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Preferred parameters for FASTA analysis are: ktup=1, gapopening-penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990). FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a serine-threonine protein kinase polypeptide can be found using computer programs well known in the art, such as DNASTAR software. Whether an amino acid change results in a biologically active serine-threonine protein kinase polypeptide can readily be determined by assaying for kinase activity, as described for example, in Trost et al., J. Biol. Chem. 275, 7373–77, 2000; Hayashi et al., Biochem. Biophys. Res. Commun. 264, 449–56, 1999; Masure et al., Eur. J. Biochem. 265, 353–60, 1999; and Mukhopadhyay et al., J. Bacteriol. 181, 6615–22, 1999.

Fusion Proteins

Fusion proteins are useful for generating antibodies against serine-threonine protein kinase polypeptide amino acid sequences and for use in various assay systems. For example, fusion proteins can be used to identify proteins that interact with portions of a serine-threonine protein kinase polypeptide. Protein affinity chromatography or library-based assays for protein-protein interactions, such as the yeast two-hybrid or phage display systems, can be used for this purpose. Such methods are well known in the art and also can be used as drug screens.

A serine-threonine protein kinase polypeptide fusion protein comprises two poly-peptide segments fused together by means of a peptide bond. The first polypeptide segment comprises at least 6, 10, 15, 20, 25, 50, 75, 100, 125, 150, 175, 200, 225, 250, 275, 300, 325, 350, or 355 contiguous amino acids of SEQ ID NO: 2 or of a biologically active variant, such as those described above. The first polypeptide segment comprises at least 6, 10, 15, 20, 25, 50, 75, 100, 125, 150, 175, 200, 225, 250, 275, 300, 325, 350, 375, 400, 425, 450, or 457 contiguous amino acids of SEQ ID NO: 6 or of a biologically active variant, such as those described above. The first polypeptide segment also can comprise full-length serine-threonine protein kinase protein.

The second polypeptide segment can be a full-length protein or a protein fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horse-radish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the serine-threonine protein kinase polypeptide-encoding sequence and the heterologous protein sequence, so that the serine-threonine protein kinase polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from SEQ ID NOS: 1 or 5 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif), MBL International Corporation (MIC; Watertown, Mass.), and Quantum Biotechnologies (Montreal, Canada; 1-888-DNA-KITS).

Identification of Species Homologs

Species homologs of human serine-threonine protein kinase polypeptide can be obtained using serine-threonine protein kinase polypeptide polynucleotides (described below) to make suitable probes or primers for screening cDNA expression libraries from other species, such as mice, monkeys, or yeast, identifying cDNAs which encode homologs of serine-threonine protein kinase polypeptide, and expressing the cDNAs as is known in the art.

Polynucleotides

A serine-threonine protein kinase polynucleotide can be single- or double-stranded and comprises a coding sequence or the complement of a coding sequence for a serine-threonine protein kinase polypeptide. A coding sequence for the human serine-threonine protein kinase of SEQ ID NO: 2 is shown in SEQ ID NO: 1; a coding sequence for the human serine-threonine protein kinase of SEQ ID NO: 6 is shown in SEQ ID NO: 5. The serine-threonine protein kinase gene is located on chromosome 19.

Degenerate nucleotide sequences encoding human serine-threonine protein kinase polypeptides, as well as homologous nucleotide sequences which are at least about 50, 55, 60, 65, 70, preferably about 75, 90, 96, 98, or 99% identical to the nucleotide sequence shown in SEQ ID NOS: 1 or 5 or its complement also are serine-threonine protein kinase polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of serine-threonine protein kinase polynucleotides that encode biologically active serine-threonine protein kinase polypeptides also are serine-threonine protein kinase polynucleotides. Polynucleotide fragments comprising at least 8, 9, 10, 11, 12, 15, 20, or 25 contiguous nucleotides of SEQ ID NOS: 1 or 5 or its complement also are serine-threonine protein kinase polynucleotides. These fragments can be used, for example, as hybridization probes or as antisense oligonucleotides.

Identification of Polynucleotide Variants and Homologs

Variants and homologs of the serine-threonine protein kinase polynucleotides described above also are serine-threonine protein kinase polynucleotides. Typically, homologous serine-threonine protein kinase polynucleotide sequences can be identified by hybridization of candidate polynucleotides to known serine-threonine protein kinase polynucleotides under stringent conditions, as is known in the art. For example, using the following wash conditions— 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the serine-threonine protein kinase polynucleotides disclosed herein also can be identified by making suitable probes or primers and screening cDNA expression libraries from other species, such as mice, monkeys, or yeast. Human variants of serine-threonine protein kinase polynucleotides can be identified, for example, by screening human cDNA expression libraries. It is well known that the $T_m$ of a double-stranded DNA decreases by 1–1.5° C. with every 1% decrease in homology (Bonner et al., J. Mol. Biol. 81, 123 (1973). Variants of human serine-threonine protein kinase polynucleotides or serine-threonine protein kinase poly-nucleotides of other species can therefore be identified by hybridizing a putative homologous serine-threonine protein kinase polynucleotide with a polynucleotide having a nucleotide sequence of SEQ ID NOS: 1 or 5 or the complement thereof to form a test hybrid. The melting temperature of the test hybrid is compared with the melting temperature of a hybrid comprising polynucleotides having perfectly complementary nucleotide sequences, and the number or percent of basepair mis-matches within the test hybrid is calculated.

Nucleotide sequences which hybridize to serine-threonine protein kinase poly-nucleotides or their complements following stringent hybridization and/or wash conditions also are serine-threonine protein kinase polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a serine-threonine protein kinase polynucleotide having a nucleotide sequence shown in SEQ ID NOS: 1 or 5 or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$T_m$=81.5° C.−16.6($\log_{10}$[Na⁺])+0.41(% G+C)−
0.63(% formamide)−600/l), where l=the length
of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A serine-threonine protein kinase polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated serine-threonine protein kinase polynucleotides. For example, restriction enzymes and probes can be used to isolate polynucleotide fragments which comprises serine-threonine protein kinase nucleotide sequences. Isolated polynucleotides are in preparations that are free or at least 70, 80, or 90% free of other molecules.

Human serine-threonine protein kinase cDNA molecules can be made with standard molecular biology techniques, using serine-threonine protein kinase mRNA as a template. Human serine-threonine protein kinase cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesize serine-threonine protein kinase polynucleotides. The degeneracy of the genetic code allows alternate nucleotide sequences to be synthesized which will encode a serine-threonine protein kinase polypeptide having, for example, an amino acid sequence shown in SEQ ID NOS: 2 or 6 or a biologically active variant thereof.

Extending Polynucleotides

The partial sequence disclosed herein can be used to identify the corresponding full length gene from which it was derived. The partial sequence can be nick-translated or end-labeled with $^{32}$P using polynucleotide kinase using labeling methods known to those with skill in the art (BASIC METHODS IN MOLECULAR BIOLOGY, Davis et al., eds., Elsevier Press, N.Y., 1986). A lambda library prepared from human tissue can be directly screened with the labeled sequences of interest or the library can be converted en masse to pBluescript (Stratagene Cloning Systems, La Jolla, Calif. 92037) to facilitate bacterial colony screening (see Sambrook et al., MOLECULAR CLONING: A LABORATORY MANUAL, Cold Spring Harbor Laboratory Press (1989, pg. 1.20).

Both methods are well known in the art. Briefly, filters with bacterial colonies containing the library in pBluescript or bacterial lawns containing lambda plaques are denatured, and the DNA is fixed to the filters. The filters are hybridized with the labeled probe using hybridization conditions described by Davis et al., 1986. The partial sequences, cloned into lambda or pBluescript, can be used as positive controls to assess background binding and to adjust the hybridization and washing stringencies necessary for accurate clone identification. The resulting autoradiograms are compared to duplicate plates of colonies or plaques; each exposed spot corresponds to a positive colony or plaque. The colonies or plaques are selected, expanded and the DNA is isolated from the colonies for further analysis and sequencing.

Positive cDNA clones are analyzed to determine the amount of additional sequence they contain using PCR with one primer from the partial sequence and the other primer from the vector. Clones with a larger vector-insert PCR product than the original partial sequence are analyzed by restriction digestion and DNA sequencing to determine whether they contain an insert of the same size or similar as the mRNA size determined from Northern blot Analysis.

Once one or more overlapping cDNA clones are identified, the complete sequence of the clones can be determined, for example after exonuclease III digestion (McCombie et al., Methods 3, 33–40, 1991). A series of deletion clones are generated, each of which is sequenced. The resulting overlapping sequences are assembled into a single contiguous sequence of high redundancy (usually three to five overlapping sequences at each nucleotide position), resulting in a highly accurate final sequence.

Various PCR-based methods can be used to extend the nucleic acid sequences disclosed herein to detect upstream sequences such as promoters and regulatory elements. For example, restriction-site PCR uses universal primers to retrieve unknown sequence adjacent to a known locus (Sarkar, PCR Methods Applic. 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., Nucleic Acids Res. 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., PCR Methods Applic. 1, 111–119, 1991). In this method, multiple restriction enzyme digestions and ligations also can be used to place an engineered double-stranded sequence into an unknown fragment of the DNA molecule before performing PCR.

Another method which can be used to retrieve unknown sequences is that of Parker et al., Nucleic Acids Res. 19, 3055–3060, 1991). Additionally, PCR, nested primers, and PROMOTERFINDER libraries (CLONTECH, Palo Alto, Calif.) can be used to walk genomic DNA (CLONTECH, Palo Alto, Calif.). This process avoids the need to screen libraries and is useful in finding intron/exon junctions.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) that are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA that might be present in limited amounts in a particular sample.

Obtaining Polypeptides

Human serine-threonine protein kinase polypeptides can be obtained, for example, by purification from human cells, by expression of serine-threonine protein kinase polynucleotides, or by direct chemical synthesis.

Protein Purification

Human serine-threonine protein kinase polypeptides can be purified from any cell that expresses the enzyme, including host cells that have been transfected with serine-threonine protein kinase expression constructs. A purified serine-threonine protein kinase polypeptide is separated from other compounds that normally associate with the serine-threonine protein kinase polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified serine-threonine protein kinase polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express a serine-threonine protein kinase polynucleotide, the polynucleotide can be inserted into an expression vector that contains the necessary elements for the transcription and translation of the inserted coding sequence. Methods that are well known to those skilled in the art can be used to construct expression vectors containing sequences encoding serine-threonine protein kinase polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a serine-threonine protein kinase polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a serine-threonine protein kinase polypeptide, vectors based on SV40 or EBV can be used with an appropriate selectable marker.

Bacterial and Yeast Expression Systems

In bacterial systems, a number of expression vectors can be selected depending upon the use intended for the serine-threonine protein kinase polypeptide. For example, when a large quantity of a serine-threonine protein kinase polypeptide is needed for the induction of antibodies, vectors which direct high level expression of fusion proteins that are readily purified can be used. Such vectors include, but are not limited to, multifunctional E. coli cloning and expression vectors such as BLUESCRIPT (Stratagene). In a BLUESCRIPT vector, a sequence encoding the serine-threonine protein kinase polypeptide can be ligated into the vector in frame with sequences for the amino-terminal Met and the subsequent 7 residues of β-galactosidase so that a hybrid protein is produced. pIN vectors (Van Heeke & Schuster, J. Biol. Chem. 264, 5503–5509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding serine-threonine protein kinase polypeptides can be driven by any of a number of promoters. For example, viral promoters such as the $^{35}$S and 19S promoters of CaMV can be used alone or in combination with the omega leader sequence from TMV (Takamatsu, EMBO J. 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (e.g., Hobbs or Murray, in McGraw Hill Yearbook of Science and Technology, McGraw Hill, New York, N.Y., pp. 191–196, 1992).

An insect system also can be used to express a serine-threonine protein kinase polypeptide. For example, in one such system Autographa californica nuclear poly-hedrosis virus (AcNPV) is used as a vector to express foreign genes in Spodoptera frugiperda cells or in Trichoplusia larvae. Sequences encoding serine-threonine protein-kinase polypeptides can be cloned into a non-essential region of the virus, such as the polyhedrin gene, and placed under control of the polyhedrin promoter. Successful insertion of serine-threonine protein kinase polypeptides will render the polyhedrin gene inactive and produce recombinant virus lacking coat protein. The recombinant viruses can then be used to infect S. frugiperda cells or Trichoplusia larvae in which serine-threonine protein kinase polypeptides can be expressed (Engelhard et al., Proc. Nat. Acad. Sci. 91, 3224–3227, 1994).

Mammalian Expression Systems

A number of viral-based expression systems can be used to express serine-threonine protein kinase polypeptides in mammalian host cells. For example, if an adenovirus is used as an expression vector, sequences encoding serine-threonine protein kinase polypeptides can be ligated into an adenovirus transcription/translation complex comprising the late promoter and tripartite leader sequence. Insertion in a non-essential E1 or E3 region of the viral genome can be used to obtain a viable virus that is capable of expressing a serine-threonine protein kinase polypeptide in infected host cells (Logan & Shenk, Proc. Natl. Acad. Sci. 81, 3655–3659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding serine-threonine protein kinase polypeptides. Such signals include the ATG initiation codon and adjacent sequences. In cases where sequences encoding a serine-threonine protein kinase polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., Results Probl. Cell Differ. 20, 125–162, 1994).

Host Cells

A host cell strain can be chosen for its ability to modulate the expression of the inserted sequences or to process the expressed serine-threonine protein kinase polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells that have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express serine-threonine protein kinase polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells that successfully express the introduced serine-threonine protein kinase sequences. Resistant clones of stably transformed cells can be proliferated using tissue culture techniques appropriate to the cell type. See, for example, Animal Cell Culture, R. I. Freshney, ed., 1986.

Any number of selection systems can be used to recover transformed cell lines.

These include, but are not limited to, the herpes simplex virus thymidine kinase (Wigler et al., Cell 11, 223–32, 1977) and adenine phosphoribosyltransferase (Lowy et al., Cell 22, 817–23, 1980) genes which can be employed in tk⁻ or aprt⁻ cells, respectively. Also, antimetabolite, antibiotic, or herbicide resistance can be used as the basis for selection. For example, dhfr confers resistance to methotrexate (Wigler et al., Proc. Natl. Acad. Sci. 77, 3567–70, 1980), npt confers resistance to the aminoglycosides, neomycin and G-418 (Colbere-Garapin et al., J. Mol. Biol. 150, 1–14, 1981), and als and pat confer resistance to chlorsulfuron and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, Proc. Natl. Acad. Sci. 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., Methods Mol. Biol. 55, 121–131, 1995).

Detecting Expression

Although the presence of marker gene expression suggests that the serine-threonine protein kinase polynucleotide is also present, its presence and expression may need to be confirmed. For example, if a sequence encoding a serine-threonine protein kinase polypeptide is inserted within a marker gene sequence, transformed cells containing sequences that encode a serine-threonine protein kinase polypeptide can be identified by the absence of marker gene function. Alternatively, a marker gene can be placed in tandem with a sequence encoding a serine-threonine protein kinase polypeptide under the control of a single promoter. Expression of the marker gene in response to induction or selection usually indicates expression of the serine-threonine protein kinase polynucleotide.

Alternatively, host cells which contain a serine-threonine protein kinase poly-nucleotide and which express a serine-threonine protein kinase polypeptide can be identified by a variety of procedures known to those of skill in the art. These procedures include, but are not limited to, DNA-DNA or DNA-RNA hybridizations and protein bioassay or immunoassay techniques that include membrane, solution, or chip-based technologies for the detection and/or quantification of nucleic acid or protein. For example, the presence of a polynucleotide sequence encoding a serine-threonine protein kinase polypeptide can be detected by DNA-DNA or DNA-RNA hybridization or amplification using probes or fragments or fragments of poly-nucleotides encoding a serine-threonine protein kinase polypeptide. Nucleic acid amplification-based assays involve the use of oligonucleotides selected from sequences encoding a serine-threonine protein kinase polypeptide to detect transformants that contain a serine-threonine protein kinase polynucleotide.

A variety of protocols for detecting and measuring the expression of a serine-threonine protein kinase polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a serine-threonine protein kinase polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., *J. Exp. Med.* 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding serine-threonine protein kinase polypeptides include oligolabeling, nick translation, end-labeling, or PCR amplification using a labeled nucleotide. Alternatively, sequences encoding a serine-threonine protein kinase polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding a serine-threonine protein kinase polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode serine-threonine protein kinase poly-peptides can be designed to contain signal sequences which direct secretion of soluble serine-threonine protein kinase polypeptides through a prokaryotic or eukaryotic cell membrane or which direct the membrane insertion of membrane-bound serine-threonine protein kinase polypeptide.

As discussed above, other constructions can be used to join a sequence encoding a serine-threonine protein kinase polypeptide to a nucleotide sequence encoding a polypeptide domain that will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the serine-threonine protein kinase polypeptide also can be used to facilitate purification. One such expression vector provides for expression of a fusion protein containing a serine-threonine protein kinase polypeptide and 6 histidine residues preceding a thioredoxin or an enterokinase cleavage site. The histidine residues facilitate purification by IMAC (immobilized metal ion affinity chromatography, as described in Porath et al., *Prot. Exp. Purif.* 3, 263–281, 1992), while the enterokinase cleavage site provides a means for purifying the serine-threonine protein kinase polypeptide from the fusion protein. Vectors that contain fusion proteins are disclosed in Kroll et al., *DNA Cell Biol.* 12, 441–453, 1993.

Chemical Synthesis

Sequences encoding a serine-threonine protein kinase polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, a serine-threonine protein kinase polypeptide itself can be produced using chemical methods to synthesize its amino acid sequence, such as by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Optionally, fragments of serine-threonine protein kinase polypeptides can be separately synthesized and combined using chemical methods to produce a full-length molecule.

The newly synthesized peptide can be substantially purified by preparative high performance liquid chromatography (e.g., Creighton, PROTEINS: STUCTURES AND MOLECULAR PRINCIPLES, WH Freeman and Co., New York, N.Y., 1983). The composition of a synthetic serine-threonine protein kinase polypeptide can be confirmed by amino acid analysis or sequencing (e.g., the Edman degradation procedure; see Creighton, supra). Additionally, any portion of the amino acid sequence of the serine-threonine protein kinase polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce serine-threonine protein kinase polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life that is longer than that of a transcript generated from the naturally occurring sequence.

The nucleotide sequences disclosed herein can be engineered using methods generally known in the art to alter serine-threonine protein kinase polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of a serine-threonine protein kinase polypeptide. "Antibody" as used herein includes intact immunoglobulin molecules, as well as fragments thereof, such as Fab, F(ab')$_2$, and Fv, which are capable of binding an epitope of a serine-threonine protein kinase polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a serine-threonine protein kinase polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody that specifically binds to the immunogen.

Typically, an antibody that specifically binds to a serine-threonine protein kinase polypeptide provides a detection signal at least 5-, 10-, or 20-fold higher than a detection signal provided with other proteins when used in an immunochemical assay. Preferably, antibodies that specifically bind to serine-threonine protein kinase polypeptides do not detect other proteins in immunochemical assays and can immunoprecipitate a serine-threonine protein kinase polypeptide from solution.

Human serine-threonine protein kinase polypeptides can be used to immunize a mammal, such as a mouse, rat, rabbit, guinea pig, monkey, or human, to produce polyclonal antibodies. If desired, a serine-threonine protein kinase polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies that specifically bind to a serine-threonine protein kinase polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci.* 80, 2026–2030, 1983; Cole et al., *Mol. Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies that specifically bind to a serine-threonine protein kinase polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies that specifically bind to serine-threonine protein kinase polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81–91).

Antibodies which specifically bind to serine-threonine protein kinase polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which a serine-threonine protein kinase polypeptide is bound. The bound antibodies can then be eluted from the column using a buffer with a high salt concentration.

Antisense Oligonucleotides

Antisense oligonucleotides are nucleotide sequences that are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of serine-threonine protein kinase gene products in the cell.

Anti sense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkyl-phosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of serine-threonine protein kinase gene expression can be obtained by designing antisense oligonucleotides that will form duplexes to the control, 5', or regulatory regions of the serine-threonine protein kinase gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of a serine-threonine protein kinase polynucleotide. Antisense oligonucleotides which comprise, for example, 2, 3, 4, or 5 or more stretches of contiguous nucleotides which are precisely complementary to a serine-threonine protein kinase polynucleotide, each separated by a stretch of contiguous nucleotides which are not complementary to adjacent serine-threonine protein kinase nucleotides, can provide sufficient targeting specificity for serine-threonine protein kinase mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular serine-threonine protein kinase polynucleotide sequence.

Antisense oligonucleotides can be modified without affecting their ability to hybridize to a serine-threonine protein kinase polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a serine-threonine protein kinase polynucleotide can be used to generate ribozymes that will specifically bind to mRNA transcribed from the serine-threonine protein kinase polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a serine-threonine protein kinase RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate serine-threonine protein kinase RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease serine-threonine protein kinase expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors that induce expression of a target gene. Ribozymes also can be engineered to provide an additional level of regulation, so that destruction of mRNA occurs only when both a ribozyme and a target gene are induced in the cells.

Differentially Expressed Genes

Described herein are methods for the identification of genes whose products interact with human serine-threonine protein kinase. Such genes may represent genes that are differentially expressed in disorders including, but not limited to, cancer, diabetes, COPD, and peripheral and central nervous system disorders. Further, such genes may represent genes that are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human serine-threonine protein kinase gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

Identification of Differentially Expressed Genes

To identify differentially expressed genes total RNA or, preferably, mRNA is isolated from tissues of interest. For example, RNA samples are obtained from tissues of experimental subjects and from corresponding tissues of control subjects. Any RNA isolation technique that does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples that represent RNA produced by differentially expressed genes are identified by methods well known to those of skill in the art. They include, for example, differential screening (Tedder et al., Proc. Natl. Acad. Sci. U.S.A. 85, 208–12, 1988), sub-tractive hybridization (Hedrick et al., Nature 308, 149–53; Lee et al., Proc. Natl. Acad. Sci. U.S.A. 88, 2825, 1984), differential display (Liang & Pardee, Science 257, 967–71, 1992; U.S. Pat. No. 5,262,311), and microarrays.

The differential expression information may itself suggest relevant methods for the treatment of disorders involving the human serine-threonine protein kinase. For example, treatment may include a modulation of expression of the differentially expressed genes and/or the gene encoding the human serine-threonine protein kinase. The differential expression information may indicate whether the expression or activity of the differentially expressed gene or gene product or the human serine-threonine protein kinase gene or gene product are up-regulated or down-regulated.

Screening Methods

The invention provides assays for screening test compounds that bind to or modulate the activity of a serine-threonine protein kinase polypeptide or a serine-threonine protein kinase polynucleotide. A test compound preferably binds to a serine-threonine protein kinase polypeptide or polynucleotide. More preferably, a test compound decreases or increases serine-threonine protein kinase activity by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl. Acad Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al, Angew. Chem. Int. Ed. Engl. 33, 2059, 1994; Carell et al., Angew. Chem. Int. Ed. Engl. 33, 2061; Gallop et al., J. Med. Chem. 37, 1233, 1994). Libraries of compounds can be presented in solution (see, e.g., Houghten, BioTechniques 13, 412–421, 1992), or on beads (Lam, Nature 354, 82–84, 1991), chips (Fodor, Nature 364, 555–556, 1993), bacteria or spores (Ladner, U.S. Pat. No. 5,223,409), plasmids (Cull et al., Proc. Natl. Acad. Sci. U.S.A. 89, 1865–1869, 1992), or phage (Scott & Smith, Science 249, 386–390, 1990; Devlin, Science 249, 404–406, 1990); Cwirla et al., Proc. Natl. Acad. Sci. 97, 6378–6382, 1990; Felici, J. Mol. Biol. 222, 301–310, 1991; and Ladner, U.S. Pat. No. 5,223,409).

High Throughput Screening

Test compounds can be screened for the ability to bind to serine-threonine protein kinase polypeptides or polynucleotides or to affect serine-threonine protein kinase activity or serine-threonine protein kinase gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 μl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule that binds to and occupies, for example, the active site of the serine-threonine protein kinase polypeptide, such that normal biological activity is prevented. Examples of such small molecules include, but are not limited to, small peptides or peptide-like molecules.

In binding assays, either the test compound or the serine-threonine protein kinase polypeptide can comprise a detectable label, such as a fluorescent, radioisotopic, chemiluminescent, or enzymatic label, such as horseradish peroxidase, alkaline phosphatase, or luciferase. Detection of a test compound that is bound to the serine-threonine protein kinase polypeptide can then be accomplished, for example, by direct counting of radioemmission, by scintillation counting, or by determining conversion of an appropriate substrate to a detectable product.

Alternatively, binding of a test compound to a serine-threonine protein kinase polypeptide can be determined without labeling either of the interactants. For example, a microphysiometer can be used to detect binding of a test compound with a serine-threonine protein kinase polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a serine-threonine protein kinase polypeptide (McConnell et al., *Science* 257, 1906–1912, 1992).

Determining the ability of a test compound to bind to a serine-threonine protein kinase polypeptide also can be accomplished using a technology such as real-time Bimolecular Interaction Analysis (BIA) (Sjolander & Urbaniczky, *Anal. Chem.* 63, 2338–2345, 1991, and Szabo et al., *Curr. Opin. Struct. Biol.* 5, 699–705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a serine-threonine protein kinase polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO94/10300), to identify other proteins which bind to or interact with the serine-threonine protein kinase polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding a serine-threonine protein kinase polypeptide can be fused to a poly-nucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein that interacts with the serine-threonine protein kinase polypeptide.

It may be desirable to immobilize either the serine-threonine protein kinase poly-peptide (or polynucleotide) or the test compound to facilitate separation of bound from unbound forms of one or both of the interactants, as well as to accommodate automation of the assay. Thus, either the serine-threonine protein kinase polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a serine-threonine protein kinase polypeptide (or polynucleotide) can be accomplished in any vessel suitable for containing the reactants. Examples of such vessels include microtiter plates, test tubes, and microcentrifuge tubes.

In one embodiment, the serine-threonine protein kinase polypeptide is a fusion protein comprising a domain that allows the serine-threonine protein kinase polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed serine-threonine protein kinase polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a serine-threonine protein kinase polypeptide (or polynucleotide) or a test compound can be immobilized utilizing conjugation of biotin and streptavidin. Biotinylated serine-threonine protein kinase polypeptides (or polynucleotides) or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a serine-threonine protein kinase polypeptide, polynucleotide, or a test compound, but which do not interfere with a desired binding site, such as the active site of the serine-threonine protein kinase polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the serine-threonine protein kinase polypeptide or test compound, enzyme-linked assays which rely on detecting an activity of the serine-threonine protein kinase polypeptide, and SDS gel electrophoresis under non-reducing conditions.

Screening for test compounds which bind to a serine-threonine protein kinase polypeptide or polynucleotide also can be carried out in an intact cell. Any cell which comprises a serine-threonine protein kinase polypeptide or polynucleotide can be used in a cell-based assay system. A serine-threonine protein kinase poly-nucleotide can be naturally occurring in the cell or can be introduced using techniques such as those described above. Binding of the test compound to a serine-threonine protein kinase polypeptide or polynucleotide is determined as described above.

Enzyme Assays

Test compounds can be tested for the ability to increase or decrease the serine-threonine protein kinase activity of a human serine-threonine protein kinase poly-peptide. Kinase activity can be measured, for example, as taught in Trost et al., *J. Biol. Chem.* 275, 7373–77, 2000; Hayashi et al., *Biochem. Biophys. Res. Commun.* 264, 449–56, 1999; Masure et al., *Eur. J. Biochem.* 265, 353–60, 1999; and Mukhopadhyay et al., *J. Bacteriol.* 181, 6615–22, 1999. Enzyme assays can be carried out after contacting either a purified serine-threonine protein kinase polypeptide, a cell membrane preparation, or an intact cell with a test compound. A test compound that decreases a serine-threonine protein kinase activity of a serine-threonine protein kinase polypeptide by at least about 10, preferably about 50, more preferably about 75, 90, or 100% is identified as a potential therapeutic agent for decreasing serine-threonine protein kinase activity. A test compound which increases a serine-threonine protein kinase activity of a human serine-threonine protein kinase poly-peptide by at least about 10, preferably about 50, more preferably about 75, 90, or 100% is identified as a potential therapeutic agent for increasing human serine-threonine protein kinase activity.

Gene Expression

In another embodiment, test compounds that increase or decrease serine-threonine protein kinase gene expression are identified. A serine-threonine protein kinase polynucleotide is contacted with a test compound, and the expression of an RNA or polypeptide product of the serine-threonine protein kinase polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of serine-threonine protein kinase mRNA or polypeptide expression in the cells can be determined by methods well known in the art for detecting mRNA or polypeptide. Either qualitative or quantitative methods can be used. The presence of polypeptide products of a serine-threonine protein kinase polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a serine-threonine protein kinase polypeptide.

Such screening can be carried out either in a cell-free assay system or in an intact cell. Any cell that expresses a serine-threonine protein kinase polynucleotide can be used in a cell-based assay system. The serine-threonine protein kinase polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also provides pharmaceutical compositions that can be administered to a patient to achieve a therapeutic effect. Pharmaceutical compositions of the invention can comprise, for example, a serine-threonine protein kinase polypeptide, serine-threonine protein kinase polynucleotide, ribozymes or antisense oligonucleotides, antibodies which specifically bind to a serine-threonine protein kinase polypeptide, or mimetics, activators, or inhibitors of a serine-threonine protein kinase polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

Human serine-threonine protein kinase can be regulated to treat cancer, diabetes, COPD, and peripheral and central nervous system disorders.

Cancer

Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Agonists and/or antagonists of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

Diabetes

Diabetes mellitus is a common metabolic disorder characterized by an abnormal elevation in blood glucose, alterations in lipids and abnormalities (complications) in the cardiovascular system, eye, kidney and nervous system. Diabetes is divided into two separate diseases: type 1 diabetes juvenile onset), which results from a loss of cells which make and secrete insulin, and type 2 diabetes (adult onset), which is caused by a defect in insulin secretion and a defect in insulin action.

Type 1 diabetes is initiated by an autoimmune reaction that attacks the insulin secreting cells (beta cells) in the pancreatic islets. Agents that prevent this reaction from occurring or that stop the reaction before destruction of the beta cells has been accomplished are potential therapies for this disease. Other agents that induce beta cell proliferation and regeneration also are potential therapies.

Type II diabetes is the most common of the two diabetic conditions (6% of the population). The defect in insulin secretion is an important cause of the diabetic condition and results from an inability of the beta cell to properly detect and respond to rises in blood glucose levels with insulin release. Therapies that increase the response by the beta cell to glucose would offer an important new treatment for this disease.

The defect in insulin action in Type II diabetic subjects is another target for therapeutic intervention. Agents that increase the activity of the insulin receptor in muscle, liver, and fat will cause a decrease in blood glucose and a normalization of plasma lipids. The receptor activity can be increased by agents that directly stimulate the receptor or that increase the intracellular signals from the receptor. Other therapies can directly activate the cellular end process, i.e. glucose transport or various enzyme systems, to generate an insulin-like effect and therefore a produce beneficial outcome. Because overweight subjects have a greater susceptibility to Type II diabetes, any agent that reduces body weight is a possible therapy.

Both Type I and Type diabetes can be treated with agents that mimic insulin action or that treat diabetic complications by reducing blood glucose levels. Likewise, agents that reduces new blood vessel growth can be used to treat the eye complications that develop in both diseases.

COPD

Chronic obstructive pulmonary (or airways) disease (COPD) is a condition defined physiologically as airflow obstruction that generally results from a mixture of emphysema and peripheral airway obstruction due to chronic bronchitis (Senior & Shapiro, *Pulmonary Diseases and Disorders*, 3d ed., New York, McGraw-Hill, 1998, pp. 659–681, 1998; Barnes, *Chest* 117, 10S–14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

Chronic inflammation of the airways is a key pathological feature of COPD (Senior & Shapiro, 1998). The inflammatory cell population comprises increased numbers of macrophages, neutrophils, and $CD8^+$ lymphocytes. Inhaled irritants, such as cigarette smoke, activate macrophages that are resident in the respiratory tract, as well as epithelial cells leading to release of chemokines (e.g., interleukin-8) and other chemotactic factors. These chemotactic factors act to increase the neutrophil/-monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

Peripheral and Central Nervous System Disorders

Central and peripheral nervous system disorders also can be treated, such as primary and secondary disorders after brain injury, disorders of mood, anxiety disorders, disorders of thought and volition, disorders of sleep and wakefulness, diseases of the motor unit, such as neurogenic and myopathic disorders, neurodegenerative disorders such as Alzheimer's and Parkinson's disease, and processes of peripheral and chronic pain.

Pain that is associated with peripheral or central nervous system disorders also can be treated by regulating the activity of human serine-threonine protein kinase. Pain which can be treated includes that associated with central nervous system disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular mal-formation). Non-central neuropathic pain includes that associated with post mastectomy pain, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with cancer and cancer treatment also can be treated, as can headache pain (for example, migraine with aura, migraine without aura, and other migraine disorders), episodic and chronic tension-type headache, tension-type like headache, cluster headache, and chronic paroxysmal hemicrania.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a serine-threonine protein kinase polypeptide binding molecule) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects serine-threonine protein kinase activity can be administered to a human cell, either in vitro or in vivo, to reduce serine-threonine protein kinase activity. The reagent preferably binds to an expression product of a human serine-threonine protein kinase gene. If the expression product is a protein, the reagent is preferably an antibody. For treatment of human cells ex vivo, an antibody can be added to a preparation of stem cells that have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 μg of DNA per 16 nmole of liposome delivered to about $10^6$ cells, more preferably about 1.0 μg of DNA per 16 nmole of liposome delivered to about $10^6$ cells, and even more preferably about 2.0 μg of DNA per 16 nmol of liposome delivered to about $10^6$ cells. Preferably, a liposome is between about 100 and 500 nm, more preferably between about 150 and 450 μm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods that are standard in the art (see, for example, U.S. Pat. No. 5,705,151). Preferably, from about 0.1 μg to about 10 μg of polynucleotide is combined with about 8 nmol of liposomes, more preferably from about 0.5 μg to about 5 μg of polynucleotides are combined with about 8 mmol liposomes, and even more preferably about 1.0 μg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

Determination of a Therapeutically Effective Dose

The determination of a therapeutically effective dose is well within the capability of those skilled in the art. A therapeutically effective dose refers to that amount of active ingredient which increases or decreases serine-threonine protein kinase activity relative to the serine-threonine protein kinase activity which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of poly-nucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 μg to about 50 μg/kg, about 50 μg to about 5 mg/kg, about 100 μg to about 500 μg/kg of patient body weight, and about 200 to about 250 μg/kg of patient body weight. For administration of polynucleotides encoding single-chain antibodies, effective in vivo dosages are in the range of about 100 ng to about 200 ng, 500 ng to about 50 mg, about 1 μg to about 2 mg, about 5 μg to about 500 μg, and about 20 μg to about 100 μg of DNA.

If the expression product is mRNA, the reagent is preferably an antisense oligo-nucleotide or a ribozyme. Polynucleotides that express antisense oligonucleotides or ribozymes can be introduced into cells by a variety of methods, as described above.

Preferably, a reagent reduces expression of a serine-threonine protein kinase gene or the activity of a serine-threonine protein kinase polypeptide by at least about 10, preferably about 50, more preferably about 75, 90, or 100% relative to the absence of the reagent. The effectiveness of the mechanism chosen to decrease the level of expression of a serine-threonine protein kinase gene or the activity of a serine-threonine protein kinase polypeptide can be assessed using methods well known in the art, such as hybridization of nucleotide probes to serine-threonine protein kinase-specific mRNA, quantitative RT-PCR, immunologic detection of a serine-threonine protein kinase polypeptide, or measurement of serine-threonine protein kinase activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

Human serine-threonine protein kinase also can be used in diagnostic assays for detecting diseases and abnormalities or susceptibility to diseases and abnormalities related to the presence of mutations in the nucleic acid sequences that encode the enzyme. For example, differences can be determined between the cDNA or genomic sequence encoding serine-threonine protein kinase in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., *Science* 230, 1242, 1985). Sequence changes at specific locations can also be revealed by nuclease protection assays, such as RNase and S 1 protection or the chemical cleavage method (e.g., Cotton et al., *Proc. Natl. Acad. Sci. USA* 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of a serine-threonine protein kinase also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

EXAMPLE 1

Detection of Serine-threonine Protein Kinase Activity

For high level expression of a FLAG-tagged serine-threonine protein kinase poly-peptide, COS-1 cells are transfected with the expression vector serine-threonine protein kinase polypeptide (expressing the DNA-sequence of ID NO: 1) using the calcium phosphate method. After 5 h, the cells are infected with recombinant vaccinia virus vTF7-3 (10 plaque-forming units/cell). The cells are harvested 20 h after infection and lysed in 50 mM Tris, pH 7.5, 5 mM MgCl2, 0.1% Nonidet P-40, 0.5 mM dithiothreitol, 1 mM phenylmethylsulfonyl fluoride, 10 μg/ml aprotinin. Serine-threonine protein kinase polypeptide is immunoprecipitated from the lysate using anti-FLAG antibodies. In vitro kinase assay and phosphoamino acid analysis are performed in a volume of 40 μl with immunoprecipitated FLAG-serine-threonine protein kinase polypeptide in 50 mM Tris-HCl, pH 8.0, 50 mM NaCl, 5 mM MgCl2, 1 mM dithiothreitol. The reaction is started by the addition of 4 μl of 1 mM ATP supplemented with 5 μCi of (−32P)ATP and incubated for 30 min at 37° C. Afterward, the samples are subjected to SDS-PAGE and phosphorylated proteins are detected by autoradiography. Histone type III-S, casein, bovine serum albumin, or myelin basic proteins are used as substrates. It is shown that the polypeptide with the amino acid sequence of SEQ ID NO.: 2 has serine-threonine protein kinase activity.

EXAMPLE 2

Expression of Recombinant Human Serine-threonine Protein Kinase

The *Pichia pastoris* expression vector pPICZB (Invitrogen, San Diego, Calif.) is used to produce large quantities of recombinant human serine-threonine protein kinase polypeptides in yeast. The serine-threonine protein kinase-encoding DNA sequence is derived from SEQ ID NOS: 1 or 5. Before insertion into vector pPICZB, the DNA sequence is modified by well known methods in such a way that it contains at its 5'-end an initiation codon and at its 3'-end an enterokinase cleavage site, a His6 reporter tag and a termination codon. Moreover, at both termini recognition sequences for restriction endonucleases are added and after digestion of the multiple cloning site of pPICZ B with the corresponding restriction enzymes the modified DNA sequence is ligated into pPICZB. This expression vector is designed for inducible expression in *Pichia pastoris*, driven by a yeast promoter. The resulting pPICZ/md-His6 vector is used to transform the yeast.

The yeast is cultivated under usual conditions in 5 liter shake flasks and the recombinantly produced protein isolated from the culture by affinity chromatography (Ni-NTA-Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human serine-threonine protein kinase polypeptide is obtained.

EXAMPLE 3

Identification of Test Compounds that Bind to Serine-threonine Protein Kinase Poly-peptides Purified serine-threonine protein kinase polypeptides comprising a glutathione-S-transferase protein and absorbed onto glutathione-derivatized wells of 96-well microtiter plates are contacted with test compounds from a small molecule library at pH 7.0 in a physiological buffer solution. Human serine-threonine protein kinase polypeptides comprise the amino acid sequence shown in SEQ ID NOS: 2 or 6. The test compounds comprise a fluorescent tag. The samples are incubated for 5 minutes to one hour. Control samples are incubated in the absence of a test compound.

The buffer solution containing the test compounds is washed from the wells. Binding of a test compound to a serine-threonine protein kinase polypeptide is detected by fluorescence measurements of the contents of the wells. A test compound that increases the fluorescence in a well by at least 15% relative to fluorescence of a well in which a test compound is not incubated is identified as a compound which binds to a serine-threonine protein kinase polypeptide.

EXAMPLE 4

Identification of a Test Compound which Decreases Serine-threonine Protein Kinase Gene Expression A test compound is administered to a culture of human cells transfected with a serine-threonine protein kinase expression construct and incubated at 37° C. for 10 to 45 minutes. A culture of the same type of cells that have not been transfected is incubated for the same time without the test compound to provide a negative control.

RNA is isolated from the two cultures as described in Chirgwin et al., *Biochem.* 18, 5294–99, 1979). Northern blots are prepared using 20 to 30 μg total RNA and hybridized with a $^{32}$P-labeled serine-threonine protein kinase-specific probe at 65° C. in Express-hyb (CLONTECH). The probe comprises at least 11 contiguous nucleotides selected from the complement of SEQ ID NOS: 1 or 5. A test compound that decreases the serine-threonine protein kinase-specific signal relative to the signal obtained in the absence of the test compound is identified as an inhibitor of serine-threonine protein kinase gene expression.

EXAMPLE 5

Identification of a Test Compound which Decreases Serine-threonine Protein Kinase Activity A test compound is administered to a culture of human cells transfected with a serine-threonine protein kinase expression construct and incubated at 37° C. for 10 to 45 minutes. A culture of the same type of cells that have not been transfected is incubated for the same time without the test compound to provide a negative control. Kinase activity can be measured, for example, as taught in Trost et al., *J. Biol. Chem.* 275, 7373–77, 2000; Hayashi et al., *Biochem. Biophys. Res. Commun.* 264, 449–56, 1999; Masure et al., *Eur. J. Biochem.* 265, 353–60, 1999; and Mukhopadhyay et al., *J. Bacteriol.* 181, 6615–22, 1999.

A test compound which decreases the serine-threonine protein kinase activity of the serine-threonine protein kinase relative to the serine-threonine protein kinase activity in the absence of the test compound is identified as an inhibitor of serine-threonine protein kinase activity.

EXAMPLE 6

Tissue-specific Expression of Serine-threonine Protein Kinase

The qualitative expression pattern of serine-threonine protein kinase in various tissues is determined by Reverse Transcription-Polymerase Chain Reaction (RT-PCR).

To demonstrate that serine-threonine protein kinase is involved in cancer, expression is determined in the following tissues: adrenal gland, bone marrow, brain, cerebellum, colon, fetal brain, fetal liver, heart, kidney, liver, lung, mammary gland, pancreas, placenta, prostate, salivary gland, skeletal muscle, small intestine, spinal cord, spleen, stomach, testis, thymus, thyroid, trachea, uterus, and peripheral blood lymphocytes. Expression in the following cancer cell lines also is determined: DU-145 (prostate), NCI-H125 (lung), HT-29 (colon), COLO-205 (colon), A-549 (lung), NCI-H460 (lung), HT-116 (colon), DLD-1 (colon), MDA-MD-231 (breast), LS174T (colon), ZF-75 (breast), MDA-MN-435 (breast), HT-1080, MCF-7 (breast), and U87. Matched pairs of malignant and normal tissue from the same patient also are tested.

To demonstrate that serine-threonine protein kinase is involved in the disease process of diabetes, the following whole body panel is screened to show predominant or relatively high expression: subcutaneous and mesenteric adipose tissue, adrenal gland, bone marrow, brain, colon, fetal brain, heart, hypothalamus, kidney, liver, lung, mammary gland, pancreas, placenta, prostate, salivary gland, skeletal muscle, small intestine, spleen, stomach, testis, thymus, thyroid, trachea, and uterus. Human islet cells and an islet cell library also are tested. As a final step, the expression of serine-threonine protein kinase in cells derived from normal individuals with the expression of cells derived from diabetic individuals is compared.

To demonstrate that serine-threonine protein kinase is involved in the disease process of COPD, the initial expression panel consists of RNA samples from respiratory tissues and inflammatory cells relevant to COPD: lung (adult and fetal), trachea, freshly isolated alveolar type II cells, cultured human bronchial epithelial cells, cultured small airway epithelial cells, cultured bronchial sooth muscle cells, cultured H441 cells (Clara-like), freshly isolated neutrophils and monocytes, and cultured monocytes (macrophage-like). Body map profiling also is carried out, using total RNA panels purchased from Clontech. The tissues are adrenal gland, bone marrow, brain, colon, heart, kidney, liver, lung, mammary gland, pancreas, prostate, salivary gland, skeletal muscle, small intestine, spleen, stomach, testis, thymus, trachea, thyroid, and uterus. As a final step, the expression of serine-threonine protein kinase in cells derived from normal individuals with the expression of cells derived from COPD affected individuals is compared.

To demonstrate that serine-threonine protein kinase is involved in peripheral or central nervous system disorders, the following tissues are screened: fetal and adult brain, muscle, heart, lung, kidney, liver, thymus, testis, colon, placenta, trachea, pancreas, kidney, gastric mucosa, colon, liver, cerebellum, skin, cortex (Alzheimer's and normal), hypothalamus, cortex, amygdala, cerebellum, hippocampus, choroid, plexus, thalamus, and spinal cord.

Quantitative expression profiling. Quantitative expression profiling is performed by the form of quantitative PCR analysis called "kinetic analysis" firstly described in Higuchi et al., *BioTechnology* 10, 413–17, 1992, and Higuchi et al., *BioTechnology* 11, 1026–30, 1993. The principle is that at any given cycle within the exponential phase of PCR, the amount of product is proportional to the initial number of template copies.

If the amplification is performed in the presence of an internally quenched fluorescent oligonucleotide (TaqMan probe) complementary to the target sequence, the probe is cleaved by the 5'-3' endonuclease activity of Taq DNA polymerase and a fluorescent dye released in the medium (Holland et al., *Proc. Natl. Acad. Sci. U.S.A.* 88, 7276–80, 1991). Because the fluorescence emission will increase in direct proportion to the amount of the specific amplified product, the exponential growth phase of PCR product can be detected and used to determine the initial template concentration (Heid et al., *Genome Res.* 6, 986–94, 1996, and Gibson et al., *Genome Res.* 6,995–1001, 1996).

The amplification of an endogenous control can be performed to standardize the amount of sample RNA added to a reaction. In this kind of experiment, the control of choice is the 18S ribosomal RNA. Because reporter dyes with differing emission spectra are available, the target and the endogenous control can be independently quantified in the same tube if probes labeled with different dyes are used.

All "real time PCR" measurements of fluorescence are made in the ABI Prism 7700.

RNA extraction and cDNA preparation. Total RNA from the tissues listed above are used for expression quantification. RNAs labeled "from autopsy" were extracted from autoptic tissues with the TRIzol reagent (Life Technologies, MD) according to the manufacturer's protocol.

Fifty µg of each RNA were treated with DNase I for 1 hour at 37° C. in the following reaction mix: 0.2 U/µl RNase-free DNase I (Roche Diagnostics, Germany); 0.4 U/µl RNase inhibitor (PE Applied Biosystems, CA); 10 mM Tris-HCl pH 7.9; 10 mM $MgCl_2$; 50 mM NaCl; and 1 mM DTT.

After incubation, RNA is extracted once with 1 volume of phenol:chloroform:-isoamyl alcohol (24:24:1) and once with chloroform, and precipitated with 1/10 volume of 3 M NaAcetate, pH5.2, and 2 volumes of ethanol.

Fifty µg of each RNA from the autoptic tissues are DNase treated with the DNA-free kit purchased from Ambion (Ambion, Tex.). After resuspension and spectrophoto-metric quantification, each sample is reverse transcribed with the TaqMan Reverse Transcription Reagents (PE Applied Biosystems, CA) according to the manufacturer's protocol. The final concentration of RNA in the reaction mix is 200 ng/µL. Reverse transcription is carried out with 2.5 µM of random hexamer primers.

TaqMan quantitative analysis. Specific primers and probe are designed according to the recommendations of PE Applied Biosystems; the probe can be labeled at the 5' end FAM (6-carboxy-fluorescein) and at the 3' end with TAMRA (6-carboxy-tetramethyl-rhodamine). Quantification experiments are performed on 10 ng of reverse transcribed RNA from each sample. Each determination is done in triplicate.

Total cDNA content is normalized with the simultaneous quantification (multiplex PCR) of the 18S ribosomal RNA using the Pre-Developed TaqMan Assay Reagents (PDAR) Control Kit (PE Applied Biosystems, CA).

The assay reaction mix is as follows: 1× final TaqMan Universal PCR Master Mix (from 2× stock) (PE Applied Biosystems, CA); 1× PDAR control—18S RNA (from 20× stock); 300 nM forward primer; 900 nM reverse primer; 200 nM probe; 10 ng cDNA; and water to 25 µl.

Each of the following steps are carried out once: pre PCR, 2 minutes at 50° C., and 10 minutes at 95° C. The following steps are carried out 40 times: denaturation, 15 seconds at 95° C., annealing/extension, 1 minute at 60° C.

The experiment is performed on an ABI Prism 7700 Sequence Detector (PE Applied Biosystems, CA). At the end of the run, fluorescence data acquired during PCR are processed as described in the ABI Prism 7700 user's manual in order to achieve better background subtraction as well as signal linearity with the starting target quantity.

EXAMPLE 7

In vivo Testing of Compounds/target Validation

1. Acute Mechanistic Assays 1.1. Reduction in Mitogenic Plasma Hormone Levels

This non-tumor assay measures the ability of a compound to reduce either the endogenous level of a circulating hormone or the level of hormone produced in response to a biologic stimulus. Rodents are administered test compound (p.o., i.p., iv., i.m., or s.c.). At a predetermined time after administration of test compound, blood plasma is collected. Plasma is assayed for levels of the hormone of interest. If the normal circulating levels of the hormone are too low and/or variable to provide consistent results, the level of the hormone may be elevated by a pre-treatment with a biologic stimulus (i.e., LHRH may be injected i.m. into mice at a dosage of 30 ng/mouse to induce a burst of testosterone synthesis). The timing of plasma collection would be adjusted to coincide with the peak of the induced hormone response. Compound effects are compared to a vehicle-treated control group. An F-test is preformed to determine if the variance is equal or unequal followed by a Student's t-test. Significance is p value $\leq 0.05$ compared to the vehicle control group.

1.2. Hollow Fiber Mechanism of Action Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol, these may include assays for gene expression (bDNA, PCR, or Taqman), or a specific biochemical activity (i.e., cAMP levels. Results are analyzed by Student's t-test or Rank Sum test after the variance between groups is compared by an F-test, with significance at $p \leq 0.05$ as compared to the vehicle control group.

2. Subacute Functional In Vivo Assays 2.1. Reduction in Mass of Hormone Dependent Tissues This is another non-tumor assay that measures the ability of a compound to reduce the mass of a hormone dependent tissue (i.e., seminal vesicles in males and uteri in females). Rodents are administered test compound (p.o., i.p., i.v., i.m., or s.c.) according to a predetermined schedule and for a predetermined duration (i.e., 1 week). At termination of the study, animals are weighed, the target organ is excised, any fluid is expressed, and the weight of the organ is recorded. Blood plasma may also be collected. Plasma may be assayed for levels of a hormone of interest or for levels of test agent. Organ weights may be directly compared or they may be normalized for the body weight of the animal. Compound effects are compared to a vehicle-treated control group. An F-test is preformed to determine if the variance is equal or unequal followed by a Student's t-test. Significance is p value$\leq 0.05$ compared to the vehicle control group.

2.2. Hollow Fiber Proliferation Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol. Cell proliferation is determined by measuring a marker of cell number (i.e., MTT or LDH). The cell number and change in cell number from the starting inoculum are analyzed by Student's t-test or Rank Sum test after the variance between groups is compared by an F-test, with significance at $p \leq 0.05$ as compared to the vehicle control group.

2.3. Anti-angiogenesis Models 2.3.1. Corneal Angiogenesis

Hydron pellets with or without growth factors or cells are implanted into a micropocket surgically created in the rodent cornea. Compound administration may be systemic or local (compound mixed with growth factors in the hydron pellet). Corneas are harvested at 7 days post implantation immediately following intracardiac infusion of colloidal carbon and are fixed in 10% formalin. Readout is qualitative scoring and/or image analysis. Qualitative scores are compared by Rank Sum test. Image analysis data is evaluated by measuring the area of neovascularization (in pixels) and group averages are compared by Student's t-test (2 tail). Significance is $p \leq 0.05$ as compared to the growth factor or cells only group.

2.3.2. Matrigel Angiogenesis

Matrigel, containing cells or growth factors, is injected subcutaneously. Compounds are administered p.o., i.p., i.v., i.m., or s.c. Matrigel plugs are harvested at predetermined time point(s) and prepared for readout. Readout is an ELISA-based assay for hemoglobin concentration and/or histological examination (i.e. vessel count, special staining for endothelial surface markers: CD31, factor-8). Readouts are analyzed by Student's t-test, after the variance between groups is compared by an F-test, with significance determined at $p \leq 0.05$ as compared to the vehicle control group.

3. Primary Antitumor Efficacy 3.1. Early Therapy Models 3.1.1. Subcutaneous Tumor Tumor cells or fragments are implanted subcutaneously on Day 0. Vehicle and/or compounds are administered p.o., i.p., i.v., i.m., or s.c. according to a predetermined schedule starting at a time, usually on Day 1, prior to the ability to measure the tumor burden. Body weights and tumor measurements are recorded 2–3 times weekly. Mean net body and tumor weights are calculated for each data collection day. Anti-tumor efficacy may be initially determined by comparing the size of treated (T) and control (C) tumors on a given day by a Student's t-test, after the variance between groups is compared by an F-test, with significance determined at $p \leq 0.05$. The experiment may also be continued past the end of dosing in which case tumor measurements would continue to be recorded to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is $p \leq 0.05$.

3.1.2. Intraperitoneal/Intracranial Tumor Models

Tumor cells are injected intraperitoneally or intracranially on Day 0. Compounds are administered p.o., i.p., i.v., i.m., or s.c. according to a predetermined schedule starting on Day 1. Observations of morbidity and/or mortality are recorded twice daily. Body weights are measured and recorded twice weekly. Morbidity/mortality data is expressed in terms of the median time of survival and the number of long-term survivors is indicated separately. Survival times are used to generate Kaplan-Meier curves. Significance is $p \leq 0.05$ by a log-rank test compared to the control group in the experiment.

3.2. Established Disease Model

Tumor cells or fragments are implanted subcutaneously and grown to the desired size for treatment to begin. Once at the predetermined size range, mice are randomized into treatment groups. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group. Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group.

3.3. Orthotopic Disease Models

3.3.1. Mammary Fat Pad Assay

Tumor cells or fragments, of mammary adenocarcinoma origin, are implanted directly into a surgically exposed and reflected mammary fat pad in rodents. The fat pad is placed back in its original position and the surgical site is closed. Hormones may also be administered to the rodents to support the growth of the tumors. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group.

Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group. In addition, this model provides an opportunity to increase the rate of spontaneous metastasis of this type of tumor. Metastasis can be assessed at termination of the study by counting the number of visible foci per target organ, or measuring the target organ weight. The means of these endpoints are compared by Student's t-test after conducting an F-test, with significance determined at $p \leq 0.05$ compared to the control group in the experiment.

3.3.2. Intraprostatic Assay

Tumor cells or fragments, of prostatic adenocarcinoma origin, are implanted directly into a surgically exposed dorsal lobe of the prostate in rodents. The prostate is externalized through an abdominal incision so that the tumor can be implanted specifically in the dorsal lobe while verifying that the implant does not enter the seminal vesicles. The successfully inoculated prostate is replaced in the abdomen and the incisions throught e abdomen and skin are closed. Hormones may also be administered to the rodents to support the growth of the tumors. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the lungs), or measuring the target organ weight (i.e., the regional lymph nodes). The means of these endpoints are compared by Student's t-test after conducting an F-test, with significance determined at $p \leq 0.05$ compared to the control group in the experiment.

3.3.3. Intrabronchial Assay

Tumor cells of pulmonary origin may be implanted intrabronchially by making an incision through the skin and exposing the trachea. The trachea is pierced with the beveled end of a 25 gauge needle and the tumor cells are inoculated into the main bronchus using a flat-ended 27 gauge needle with a 90° bend. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the contralateral lung), or measuring the target organ weight. The means of these endpoints are compared by Student's t-test after conducting an F-test, with significance determined at $p \leq 0.05$ compared to the control group in the experiment.

3.3.4. Intracecal Assay

Tumor cells of gastrointestinal origin may be implanted intracecally by making an abdominal incision through the skin and externalizing the intestine. Tumor cells are inoculated into the cecal wall without penetrating the lumen of the intestine using a 27 or 30 gauge needle. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the liver), or measuring the target organ weight. The means of these endpoints are compared by Student's t-test after conducting an F-test, with significance determined at $p \leq 0.05$ compared to the control group in the experiment.

4. Secondary (Metastatic) Antitumor Efficacy

4.1. Spontaneous Metastasis

Tumor cells are inoculated s.c. and the tumors allowed to grow to a predetermined range for spontaneous metastasis studies to the lung or liver. These primary tumors are then excised. Compounds are administered p.o., i.p., i.v., i.m., or s.c. according to a predetermined schedule which may include the period leading up to the excision of the primary tumor to evaluate therapies directed at inhibiting the early stages of tumor metastasis. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance determined at $p \leq 0.05$ compared to the control group in the experiment for both of these endpoints.

4.2. Forced Metastasis

Tumor cells are injected into the tail vein, portal vein, or the left ventricle of the heart in experimental (forced) lung, liver, and bone metastasis studies, respectively. Compounds are administered p.o., i.p., i.v., i.m., or s.c. according to a predetermined schedule. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance at $p \leq 0.05$ compared to the vehicle control group in the experiment for both endpoints.

EXAMPLE 8

Proliferation Inhibition Assay: Antisense Oligonucleotides Suppress the Growth of Cancer Cell Lines The cell line used for testing is the human colon cancer cell line HCT116. Cells are cultured in RPMI-1640 with 10–15% fetal calf serum at a concentration of 10,000 cells per milliliter in a volume of 0.5 ml and kept at 37° C. in a 95% air/5% $CO_2$ atmosphere.

Phosphorothioate oligoribonucleotides are synthesized on an Applied Biosystems Model 380B DNA synthesizer using phosphoroamidite chemistry. A sequence of 24 bases complementary to the nucleotides at position 1 to 24 of SEQ ID NOS: 1 or 5 is used as the test oligonucleotide. As a control, another (random) sequence is used: 5'-TCA ACT OAC TAG ATG TAC ATG GAC-3'. Following assembly and deprotection, oligonucleotides are ethanol-precipitated twice, dried, and suspended in phosphate buffered saline at the desired concentration. Purity of the oligonucleotides is tested by capillary gel electrophoresis and ion exchange HPLC. The purified oligonucleotides are added to the culture medium at a concentration of 10 µM once per day for seven days.

The addition of the test oligonucleotide for seven days results in significantly reduced expression of human serine-threonine protein kinase as determined by Western blotting. This effect is not observed with the control oligonucleotide. After 3 to 7 days, the number of cells in the cultures is counted using an automatic cell counter. The number of cells in cultures treated with the test oligonucleotide (expressed as 100%) is compared with the number of cells in cultures treated with the control oligonucleotide. The number of cells in cultures treated with the test oligonucleotide is not more than 30% of control, indicating that the inhibition of human serine-threonine protein kinase has an anti-proliferative effect on cancer cells.

EXAMPLE 9

In vivo Testing of Compounds/target Validation

1. Pain

Acute Pain

Acute pain is measured on a hot plate mainly in rats. Two variants of hot plate testing are used: In the classical variant animals are put on a hot surface (52 to 56° C.) and the latency time is measured until the animals show nocifensive behavior, such as stepping or foot licking. The other variant is an increasing temperature hot plate where the experimental animals are put on a surface of neutral temperature. Subsequently this surface is slowly but constantly heated until the animals begin to lick a hind paw. The temperature which is reached when hind paw licking begins is a measure for pain threshold.

Compounds are tested against a vehicle treated control group. Substance application is performed at different time points via different application routes (i.v., i.p., p.o., i.t., i.c.v., s.c., intradermal, transdermal) prior to pain testing.

Persistent Pain

Persistent pain is measured with the formalin or capsaicin test, mainly in rats. A solution of 1 to 5% formalin or 10 to 100 µg capsaicin is injected into one hind paw of the experimental animal. After formalin or capsaicin application the animals show nocifensive reactions like flinching, licking and biting of the affected paw. The number of nocifensive reactions within a time frame of up to 90 minutes is a measure for intensity of pain.

Compounds are tested against a vehicle treated control group. Substance application is performed at different time points via different application routes (i.v., i.p., p.o., i.t., i.c.v., s.c., intradermal, transdermal) prior to formalin or capsaicin administration.

Neuropathic Pain

Neuropathic pain is induced by different variants of unilateral sciatic nerve injury mainly in rats. The operation is performed under anesthesia. The first variant of sciatic nerve injury is produced by placing loosely constrictive ligatures around the common sciatic nerve. The second variant is the tight ligation of about the half of the diameter of the common sciatic nerve. In the next variant, a group of models is used in which tight ligations or transections are made of either the L5 and L6 spinal nerves, or the L % spinal nerve only. The fourth variant involves an axotomy of two of the three terminal branches of the sciatic nerve (tibial and common peroneal nerves) leaving the remaining sural nerve intact whereas the last variant comprises the axotomy of only the tibial branch leaving the sural and common nerves uninjured. Control animals are treated with a sham operation.

Postoperatively, the nerve injured animals develop a chronic mechanical allodynia, cold allodynioa, as well as a thermal hyperalgesia. Mechanical allodynia is measured by means of a pressure transducer (electronic von Frey Anesthesiometer, IITC Inc.-Life Science Instruments, Woodland Hills, SA, USA; Electronic von Frey System, Somedic Sales AB, Hörby, Sweden). Thermal hyperalgesia is measured by means of a radiant heat source (Plantar Test, Ugo Basile, Comerio, Italy), or by means of a cold plate of 5 to 10° C. where the nocifensive reactions of the affected hind paw are counted as a measure of pain intensity. A further test for cold induced pain is the counting of nocifensive reactions, or duration of nocifensive responses after plantar administration of acetone to the affected hind limb. Chronic pain in general is assessed by registering the circadanian rhythms in activity (Surjo and Arndt, Universität zu Köln, Cologne, Germany), and by scoring differences in gait (foot print patterns; FOOTPRINTS program, Klapdor et al., 1997. A low cost method to analyze footprint patterns. J. Neurosci. Methods 75, 49–54).

Compounds are tested against sham operated and vehicle treated control groups. Substance application is performed at different time points via different application routes (i.v., i.p., p.o., i.t., i.c.v., s.c., intradermal, transdermal) prior to pain testing.

Inflammatory Pain

Inflammatory pain is induced mainly in rats by injection of 0.75 mg carrageenan or complete Freund's adjuvant into one hind paw. The animals develop an edema with mechanical allodynia as well as thermal hyperalgesia. Mechanical allodynia is measured by means of a pressure transducer (electronic von Frey Anesthesiometer, IITC Inc.-Life Science Instruments, Woodland Hills, SA, USA). Thermal hyperalgesia is measured by means of a radiant heat source (Plantar Test, Ugo Basile, Comerio, Italy, Paw thermal stimulator, G. Ozaki, University of California, USA). For edema measurement two methods are being used. In the first method, the animals are sacrificed and the affected hindpaws sectioned and weighed. The second method comprises differences in paw volume by measuring water displacement in a plethysmometer (Ugo Basile, Comerio, Italy).

Compounds are tested against uninflamed as well as vehicle treated control groups. Substance application is performed at different time points via different application routes (i.v., i.p., p.o., i.t., i.c.v., s.c., intradermal, transdermal) prior to pain testing.

Diabetic Neuropathic Pain

Rats treated with a single intraperitoneal injection of 50 to 80 mg/kg streptozotocin develop a profound hyperglycemia and mechanical allodynia within 1 to 3 weeks. Mechanical allodynia is measured by means of a pressure transducer (electronic von Frey Anesthesiometer, IITC Inc.-Life Science Instruments, Woodland Hills, SA, USA).

Compounds are tested against diabetic and non-diabetic vehicle treated control groups. Substance application is performed at different time points via different application routes (i.v., i.p., p.o., i.t., i.c.v., s.c., intradermal, transdermal) prior to pain testing.

2. Parkinson's disease

6-Hydroxydopamine (6-OH-DA) Lesion

Degeneration of the dopaminergic nigrostriatal and striatopallidal pathways is the central pathological event in Parkinson's disease. This disorder has been mimicked experimentally in rats using single/sequential unilateral stereotaxic injections of 6-OH-DA into the medium forebrain bundle (MFB).

Male Wistar rats (Harlan Winkelmann, Germany), weighing 200±250 g at the beginning of the experiment, are used. The rats are maintained in a temperature- and humidity-controlled environment under a 12 h light/dark cycle with free access to food and water when not in experimental sessions. The following in vivo protocols are approved by the governmental authorities. All efforts are made to minimize animal suffering, to reduce the number of animals used, and to utilize alternatives to in vivo techniques.

Animals are administered pargyline on the day of surgery (Sigma, St. Louis, Mo., USA; 50 mg/kg i.p.) in order to inhibit metabolism of 6-OHDA by monoamine oxidase and desmethylimipramine HCl (Sigma; 25 mg/kg i.p.) in order to prevent uptake of 6-OHDA by noradrenergic terminals. Thirty minutes later the rats are anesthetized with sodium pentobarbital (50 mg/kg) and placed in a stereotaxic frame. In order to lesion the DA nigrostriatal pathway 4 µl of 0.01% ascorbic acid-saline containing 8 µg of 6-OHDA HBr (Sigma) are injected into the left medial fore-brain bundle at a rate of 1 µl/min (2.4 mm anterior, 1.49 mm lateral, −2.7 mm ventral to Bregma and the skull surface). The needle is left in place an additional 5 min to allow diffusion to occur.

Stepping Test

Forelimb akinesia is assessed three weeks following lesion placement using a modified stepping test protocol. In brief, the animals are held by the experimenter with one hand fixing the hindlimbs and slightly raising the hind part above the surface. One paw is touching the table, and is then moved slowly sideways (5 s for 1 m), first in the forehand and then in the backhand direction. The number of adjusting steps is counted for both paws in the backhand and forehand direction of movement. The sequence of testing is right paw forehand and backhand adjusting stepping, followed by left paw forehand and backhand directions. The test is repeated three times on three consecutive days, after an initial training period of three days prior to the first testing. Forehand adjusted stepping reveals no consistent differences between lesioned and healthy control animals. Analysis is therefore restricted to backhand adjusted stepping.

Balance Test

Balance adjustments following postural challenge are also measured during the stepping test sessions. The rats are held in the same position as described in the stepping test and, instead of being moved sideways, tilted by the experimenter towards the side of the paw touching the table. This maneuver results in loss of balance and the ability of the rats to regain balance by forelimb movements is scored on a scale ranging from 0 to 3. Score 0 is given for a normal forelimb placement. When the forelimb movement is delayed but recovery of postural balance detected, score 1 is given. Score 2 represents a clear, yet insufficient, forelimb reaction, as evidenced by muscle contraction, but lack of success in recovering balance, and score 3 is given for no reaction of movement. The test is repeated three times a day on each side for three consecutive days after an initial training period of three days prior to the first testing.

Staircase Test (Paw Reaching)

A modified version of the staircase test is used for evaluation of paw reaching behavior three weeks following primary and secondary lesion placement. Plexiglass test boxes with a central platform and a removable staircase on each side are used. The apparatus is designed such that only the paw on the same side at each staircase can be used, thus providing a measure of independent forelimb use. For each test the animals are left in the test boxes for 15 min. The double staircase is filled with 7×3 chow pellets (Precision food pellets, formula: P, purified rodent diet, size 45 mg; Sandown Scientific) on each side. After each test the number of pellets eaten (successfully retrieved pellets) and the number of pellets taken (touched but dropped) for each paw and the success rate (pellets eaten/pellets taken) are counted separately. After three days of food deprivation (12 g per animal per day) the animals are tested for 11 days. Full analysis is conducted only for the last five days.

MPTP Treatment

The neurotoxin 1-methyl-4-phenyl-1,2,3,6-tetrahydro-pyridine (MPTP) causes degeneration of mesencephalic dopaminergic (DAergic) neurons in rodents, non-human primates, and humans and, in so doing, reproduces many of the symptoms of Parkinson's disease. MPTP leads to a marked decrease in the levels of dopamine and its metabolites, and in the number of dopaminergic terminals in the striatum as well as severe loss of the tyrosine hydroxylase (TH)-immunoreactive cell bodies in the substantia nigra, pars compacta.

In order to obtain severe and long-lasting lesions, and to reduce mortality, animals receive single injections of MPTP, and are then tested for severity of lesion 7–10 days later. Successive MPTP injections are administered on days 1, 2 and 3. Animals receive application of 4 mg/kg MPTP hydrochloride (Sigma) in saline once daily. All injections are intraperitoneal (i.p.) and the MPTP stock solution is frozen between injections. Animals are decapitated on day 11.

Immunohistology

At the completion of behavioral experiments, all animals are anaesthetized with 3 ml thiopental (1 g/40 ml i.p., Tyrol Pharma). The mice are perfused transcardially with 0.01 M PBS (pH 7.4) for 2 min, followed by 4% paraformaldehyde (Merck) in PBS for 15 min. The brains are removed and placed in 4% paraformaldehyde for 24 h at 4° C. For dehydration they are then transferred to a 20% sucrose (Merck) solution in 0.1 M PBS at 4° C. until they sink. The brains are frozen in methylbutan at −20° C. for 2 min and stored at −70° C. Using a sledge microtome (mod. 3800-Frigocut, Leica), 25 µm sections are taken from the genu of the corpus callosum (AP 1.7 mm) to the hippocampus (AP 21.8 mm) and from AP 24.16 to AP 26.72. Forty-six sections are cut and stored in assorters in 0.25 M Tris buffer (pH 7.4) for immunohistochemistry.

A series of sections is processed for free-floating tyrosine hydroxylase (TH) immunohistochemistry. Following three rinses in 0.1 M PBS, endogenous peroxidase activity is quenched for 10 min in 0.3% $H_2O_2$±PBS. After rinsing in PBS, sections are preincubated in 10% normal bovine serum (Sigma) for 5 min as blocking agent and transferred to either primary anti-rat TH rabbit antiserum (dilution 1:2000).

Following overnight incubation at room temperature, sections for TH immunoreactivity are rinsed in PBS (2×10 min) and incubated in biotinylated anti-rabbit immunoglobulin G raised in goat (dilution 1:200) (Vector) for 90 min, rinsed repeatedly and transferred to Vectastain ABC (Vector) solution for 1 h. 3,.3'-Diaminobenzidine tetrahydrochloride (DAB; Sigma) in 0.1 M PBS, supplemented with 0.005% $H_2O_2$, serves as chromogen in the subsequent visualization reaction. Sections are mounted on to gelatin-coated slides, left to dry overnight, counter-stained with hematoxylin dehydrated in ascending alcohol concentrations and cleared in butylacetate. Coverslips are mounted on entellan.

Rotarod Test

We use a modification of the procedure described by Rozas and Labandeira-Garcia (1997), with a CR-1 Rotamex system (Columbus Instruments, Columbus, Ohio) comprising an IBM-compatible personal computer, a CIO-24 data acquisition card, a control unit, and a four-lane rotarod unit. The rotarod unit consists of a rotating spindle (diameter 7.3 cm) and individual compartments for each mouse. The system software allows preprogramming of session protocols with varying rotational speeds (0–80 rpm). Infrared beams are used to detect when a mouse has fallen onto the base grid beneath the rotarod. The system logs the fall as the end of the experiment for that mouse, and the total time on the rotarod, as well as the time of the fall and all the set-up parameters, are recorded. The system also allows a weak current to be passed through the base grid, to aid training.

3. Dementia

The Object Recognition Task

The object recognition task has been designed to assess the effects of experimental manipulations on the cognitive performance of rodents. A rat is placed in an open field, in which two identical objects are present. The rats inspects both objects during the first trial of the object recognition task. In a second trial, after a retention interval of for example 24 hours, one of the two objects used in the first trial, the 'familiar' object, and a novel object are placed in the open field. The inspection time at each of the objects is registered. The basic measures in the OR task is the time spent by a rat exploring the two object the second trial. Good retention is reflected by higher exploration times towards the novel than the 'familiar' object.

Administration of the putative cognition enhancer prior to the first trial predominantly allows assessment of the effects on acquisition, and eventually on consolidation processes. Administration of the testing compound after the first trial allows to assess the effects on consolidation processes, whereas administration before the second trial allows to measure effects on retrieval processes.

The Passive Avoidance Task

The passive avoidance task assesses memory performance in rats and mice. The inhibitory avoidance apparatus consists of a two-compartment box with a light compartment and a dark compartment. The two compartments are separated by a guillotine door that can be operated by the experimenter. A threshold of 2 cm separates the two compartments when the guillotine door is raised. When the door is open, the illumination in the dark compartment is about 2 lux. The light intensity is about 500 lux at the center of the floor of the light compartment.

Two habituation sessions, one shock session, and a retention session are given, separated by inter-session intervals of 24 hours. In the habituation sessions and the retention session the rat is allowed to explore the apparatus for 300 sec. The rat is placed in the light compartment, facing the wall opposite to the guillotine door. After an accommodation period of 15 sec. the guillotine door is opened so that all parts of the apparatus can be visited freely. Rats normally avoid brightly lit areas and will enter the dark compartment within a few seconds.

In the shock session the guillotine door between the compartments is lowered as soon as the rat has entered the dark compartment with its four paws, and a scrambled 1 mA footshock is administered for 2 sec. The rat is removed from the apparatus and put back into its home cage. The procedure during the retention session is identical to that of the habituation sessions.

The step-through latency, that is the first latency of entering the dark compartment (in sec.) during the retention session is an index of the memory performance of the animal; the longer the latency to enter the dark compartment, the better the retention is. A testing compound in given half an hour before the shock session, together with 1 mg*$kg^{-1}$ scopolamine.

Scopolamine impairs the memory performance during the retention session 24 hours later. If the test compound increases the enter latency compared with the scopolamine-treated controls, is likely to possess cognition enhancing potential.

The Morris Water Escape Task

The Morris water escape task measures spatial orientation learning in rodents. It is a test system that has extensively been used to investigate the effects of putative therapeutic on the cognitive functions of rats and mice. The performance of an animal is assessed in a circular water tank with an escape platform that is submerged about 1 cm below the surface of the water. The escape platform is not visible for an animal swimming in the water tank. Abundant extra-maze cues are provided by the furniture in the room, including desks, computer equipment, a second water tank, the presence of the experimenter, and by a radio on a shelf that is playing softly.

The animals receive four trials during five daily acquisition sessions. A trial is started by placing an animal into the pool, facing the wall of the tank. Each of four starting positions in the quadrants north, east, south, and west is used once in a series of four trials; their order is randomized. The escape platform is always in the same position. A trial is terminated as soon as the animal had climbs onto the escape platform or when 90 seconds have elapsed, whichever event occurs first. The animal is allowed to stay on the platform for 30 seconds. Then it is taken from the platform and the next trial is started. If an animal did not find the platform within 90 seconds it is put on the platform by the experimenter and is allowed to stay there for 30 seconds. After the fourth trial of the fifth daily session, an additional trial is given as a probe trial: the platform is removed, and the time the animal spends in the four quadrants is measured for 30 or 60 seconds. In the probe trial, all animals start from the same start position, opposite to the quadrant where the escape platform had been positioned during acquisition.

Four different measures are taken to evaluate the performance of an animal during acquisition training: escape latency, traveled distance, distance to platform, and swimming speed. The following measures are evaluated for the probe trial: time (s) in quadrants and traveled distance (cm) in the four quadrants. The probe trial provides additional information about how well an animal learned the position of the escape platform. If an animal spends more time and swims a longer distance in the quadrant where the platform had been positioned during the acquisition sessions than in any other quadrant, one concludes that the platform position has been learned well.

In order to assess the effects of putative cognition enhancing compounds, rats or mice with specific brain lesions which impair cognitive functions, or animals treated with compounds such as scopolamine or MK-801, which interfere with normal learning, or aged animals which suffer from cognitive deficits, are used.

The T-maze Spontaneous Alternation Task

The T-maze spontaneous alternation task (TeMCAT) assesses the spatial memory performance in mice. The start arm and the two goal arms of the T-maze are provided with guillotine doors which can be operated manually by the experimenter. A mouse is put into the start arm at the beginning of training. The guillotine door is closed. In the first trial, the 'forced trial', either the left or right goal arm is blocked by lowering the guillotine door. After the mouse has been released from the start arm, it will negotiate the maze, eventually enter the open goal arm, and return to the start position, where it will be confined for 5 seconds, by lowering the guillotine door. Then, the animal can choose freely between the left and right goal arm (all guillotine-doors opened) during 14 'free choice' trials. As soon a the mouse has entered one goal arm, the other one is closed. The mouse eventually returns to the start arm and is free to visit whichever go alarm it wants after having been confined to the start arm for 5 seconds. After completion of 14 free choice trials in one session, the animal is removed from the maze. During training, the animal is never handled.

The percent alternations out of 14 trials is calculated. This percentage and the total time needed to complete the first forced trial and the subsequent 14 free choice trials (in s) is analyzed. Cognitive deficits are usually induced by an injection of scopolamine, 30 min before the start of the training session. Scopolamine reduced the per-cent alternations to chance level, or below. A cognition enhancer, which is always administered before the training session, will at least partially, antagonize the scopolamine-induced reduction in the spontaneous alternation rate.

EXAMPLE 10

Diabetes: In vivo Testing of Compounds/target Validation

1. Glucose Production

Over-production of glucose by the liver, due to an enhanced rate of gluconeogenesis, is the major cause of fasting hyperglycemia in diabetes. Overnight fasted normal rats or mice have elevated rates of gluconeogenesis as do streptozotocin-induced diabetic rats or mice fed ad libitum. Rats are made diabetic with a single intravenous injection of 40 mg/kg of streptozotocin while C57BL/KsJ mice are given 40–60 mg/kg i.p. for 5 consecutive days. Blood glucose is measured from tail-tip blood and then compounds are administered via different routes (p.o., i.p., i.v., s.c.). Blood is collected at various times thereafter and glucose measured. Alternatively, compounds are administered for several days, then the animals are fasted overnight, blood is collected and plasma glucose measured. Compounds that inhibit glucose production will decrease plasma glucose levels compared to the vehicle-treated control group.

2. Insulin Sensitivity

Both ob/ob and db/db mice as well as diabetic Zucker rats are hyperglycemic, hyperinsulinemic and insulin resistant. The animals are pre-bled, their glucose levels measured, and then they are grouped so that the mean glucose level is the same for each group. Compounds are administered daily either q.d. or b.i.d. by different routes (p.o., i.p., s.c.) for 7–28 days. Blood is collected at various times and plasma glucose and insulin levels determined. Compounds that improve insulin sensitivity in these models will decrease both plasma glucose and insulin levels when compared to the vehicle-treated control group.

3. Insulin Secretion

Compounds that enhance insulin secretion from the pancreas will increase plasma insulin levels and improve the disappearance of plasma glucose following the administration of a glucose load. When measuring insulin levels, compounds are administered by different routes (p.o., i.p., s.c. or i.v.) to overnight fasted normal rats or mice. At the appropriate time an intravenous glucose load (0.4 g/kg) is given, blood is collected one minute later. Plasma insulin levels are determined. Compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60 and 90 minutes and plasma glucose levels determined. Compounds that increase insulin levels will decrease glucose levels and the area-under-the glucose curve when compared to the vehicle-treated group given only glucose.

Compounds that enhance insulin secretion from the pancreas will increase plasma insulin levels and improve the disappearance of plasma glucose following the administration of a glucose load. When measuring insulin levels, test compounds which regulate serine-threonine protein kinase are administered by different routes (p.o., i.p., s.c., or i.v.) to overnight fasted normal rats or mice. At the appropriate time an intravenous glucose load (0.4 g/kg) is given, blood is collected one minute later. Plasma insulin levels are determined. Test compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60, and 90 minutes and plasma glucose levels determined. Test compounds that increase insulin levels will decrease glucose levels and the area-under-the glucose curve when compared to the vehicle-treated group given only glucose.

4. Glucose Production

Over-production of glucose by the liver, due to an enhanced rate of gluconeogenesis, is the major cause of fasting hyperglycemia in diabetes. Overnight fasted normal rats or mice have elevated rates of gluconeogenesis as do streptozotocin-induced diabetic rats or mice fed ad libitum. Rats are made diabetic with a single intravenous injection of 40 mg/kg of streptozotocin while C57BL/KsJ mice are given 40–60 mg/kg i.p. for 5 consecutive days. Blood glucose is measured from tail-tip blood and then compounds are administered via different routes (p.o., i.p., i.v., s.c.). Blood is collected at various times thereafter and glucose measured. Alternatively, compounds are administered for several days, then the animals are fasted overnight, blood is collected and plasma glucose measured. Compounds that inhibit glucose production will decrease plasma glucose levels compared to the vehicle-treated control group.

5. Insulin Sensitivity

Both ob/ob and db/db mice as well as diabetic Zucker rats are hyperglycemic, hyperinsulinemic and insulin resistant. The animals are pre-bled, their glucose levels measured, and then they are grouped so that the mean glucose level is the same for each group. Compounds are administered daily either q.d. or b.i.d. by different routes (p.o., i.p., s.c.) for 7–28 days. Blood is collected at various times and plasma glucose and insulin levels determined. Compounds that improve insulin sensitivity in these models will decrease both plasma glucose and insulin levels when compared to the vehicle-treated control group.

6. Insulin Secretion

Compounds that enhance insulin secretion from the pancreas will increase plasma insulin levels and improve the disappearance of plasma glucose following the administration of a glucose load. When measuring insulin levels, compounds are administered by different routes (p.o., i.p., s.c. or i.v.) to overnight fasted normal rats or mice. At the appropriate time an intravenous glucose load (0.4 g/kg) is given, blood is collected one minute later. Plasma insulin levels are determined. Compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60 and 90 minutes and plasma glucose levels determined. Compounds that increase insulin levels will decrease glucose levels and the area-under-the glucose curve when compared to the vehicle-treated group given only glucose.

EXAMPLE 11

Identification of Test Compound Efficacy in a COPD Animal Model

Guinea pigs are exposed on a single occasion to tobacco smoke for 50 minutes. Animals are sacrificed between 10 minutes and 24 hour following the end of the exposure and their lungs placed in RNAlater™. The lung tissue is homogenized, and total RNA was extracted using a Qiagens RNeasy™ Maxi kit. Molecular Probes RiboGreen™ RNA quantitation method is used to quantify the amount of RNA in each sample.

Total RNA is reverse transcribed, and the resultant cDNA is used in a real-time polymerase chain reaction (PCR). The cDNA is added to a solution containing the sense and anti-sense primers and the 6-carboxy-tetramethyl-rhodamine labeled probe of the serine-threonine protein kinase gene. Cyclophilin is used as the housekeeping gene. The expression of the serine-threonine protein kinase gene is measured using the TaqMan real-time PCR system that generates an amplification curve for each sample. From this curve a threshold cycle value is calculated: the fractional cycle number at which the amount of amplified target reaches a fixed threshold. A sample containing many copies of the serine-threonine protein kinase gene will reach this threshold earlier than a sample containing fewer copies. The threshold is set at 0.2, and the threshold cycle $C_T$ is calculated from the amplification curve. The $C_T$ value for the serine-threonine protein kinase gene is normalized using the $C_T$ value for the housekeeping gene.

Expression of the serine-threonine protein kinase gene is increased by at least 3-fold between 10 minutes and 3 hours post tobacco smoke exposure compared to air exposed control animals.

Test compounds are evaluated as follows. Animals are pre-treated with a test compound between 5 minutes and 1 hour prior to the tobacco smoke exposure and they are then sacrificed up to 3 hours after the tobacco smoke exposure has been completed. Control animals are pre-treated with the vehicle of the test compound via the route of administration chosen for the test compound. A test compound that reduces the tobacco smoke induced upregulation of serine-threonine protein kinase gene relative to the expression seen in vehicle treated tobacco smoke exposed animals is identified as an inhibitor of serine-threonine protein kinase gene expression.

EXAMPLE 12

Quantitative RT-PCR Analysis of Cancer Tissues and Obesity and Diabetes Tissues. RNA Extraction and cDNA Preparation Total RNA used for Taqman quantitative analysis were either purchased (Clontech, CA) or extracted from tissues using TRIzol reagent (Life Technologies, MD) according to a modified vendor protocol which utilizes the Rneasy protocol (Qiagen, CA).

One hundred µg of each RNA were treated with DNase I using RNase free-DNase (Qiagen, CA) for use with RNeasy or QiaAmp columns.

After elution and quantitation with Ribogreen (Molecular Probes Inc., OR) each sample was reverse transcribed using the GibcoBRL Superscript II First Strand Synthesis System for RT-PCR according to vendor protocol (Life Technologies, MD). The final concentration of RNA in the reaction mix was 50 ng/µL. Reverse transcription was performed with 0.5 µg of Oligo dT primer for the cancer panel and 50 ng of Random Hexamers for the obesity and diabetes panel.

TaqMan Quantitative Analysis

Specific primers and probe were designed according to PE Applied Biosystems recommendations and are listed below:

```
forward primer:
5'-(AGACAGTGAATGGTGGCAGTGT)-3'    (SEQ ID NO: 13)

reverse primer:
5'-(GCTGATGCGTTCGTGTGACT)-3'      (SEQ ID NO: 14)
probe: SYBR Green
```

The expected length of the PCR product was 136 bp.

Quantitation experiments were performed on 25 ng of reverse transcribed RNA from each sample. Each determination was done in duplicate. 18S ribosomal RNA was measured as a control using the Pre-Developed TaqMan Assay Reagents (PDAR)(PE Applied Biosystems, CA). Assay reaction mix was as follows:

|  | final |
|---|---|
| TaqMan SYBR Green PCR Master Mix (2×) (PE Applied Biosystems, CA) | 1× |
| Forward primer (SEQ ID NO: 13) | 300 nM |
| Reverse primer (SEQ ID NO: 14) | 300 nM |
| cDNA | 25 ng |
| Water to 25 µL | |

18s control:

| Taqman Universal PCR Master Mix (2×) (PE Applied Biosystems, CA) | 1× |
|---|---|
| PDAR control - 18S RNA (20×) | 1× |
| 18S ribosomal forward primer | 300 nM |
| 18S ribosomal reverse primer | 300 nM |
| cDNA | 25 ng |
| Water to 25 µl | |

PCR conditions:

Once: 2 minutes at 50° C.

10 minutes at 95° C.

40 cycles: 15 sec. at 95° C.

1 minute at 60° C.

The experiment was performed on an ABI Prism 7700 Sequence Detector (PE Applied Biosystems, CA). At the end of the run, fluorescence data acquired during PCR were processed as described in the ABI Prism 7700 user's manual.

For cancer tissues, fold change was calculated using the delta-delta CT method with normalization to the 18S RNA values. Results are shown in FIG. 20.

Figure 21:
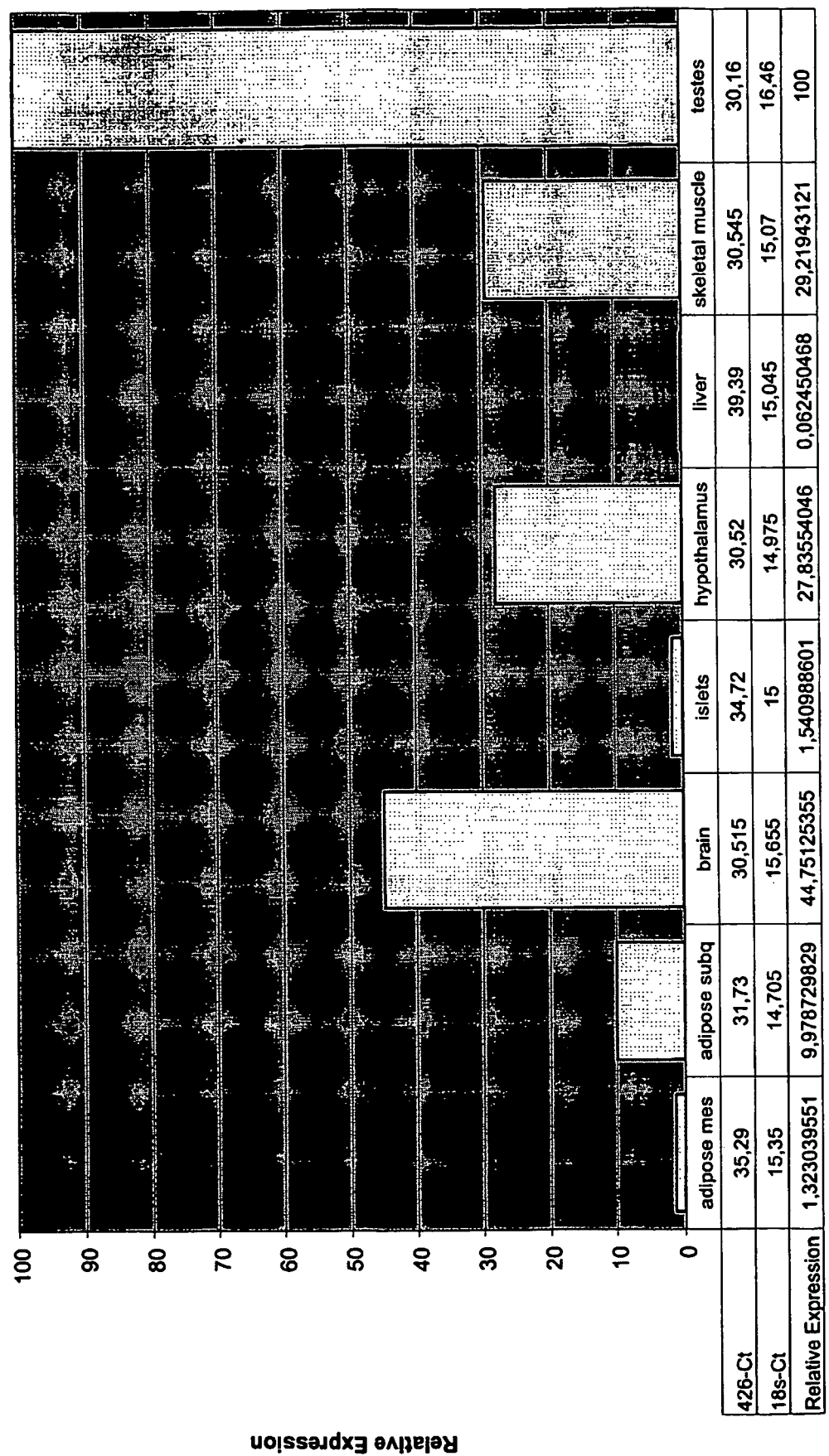
FIG. 21 shows the human serine/threonine kinase relative mRNA expression in obesity and diabetes tissues.
Figure 22:
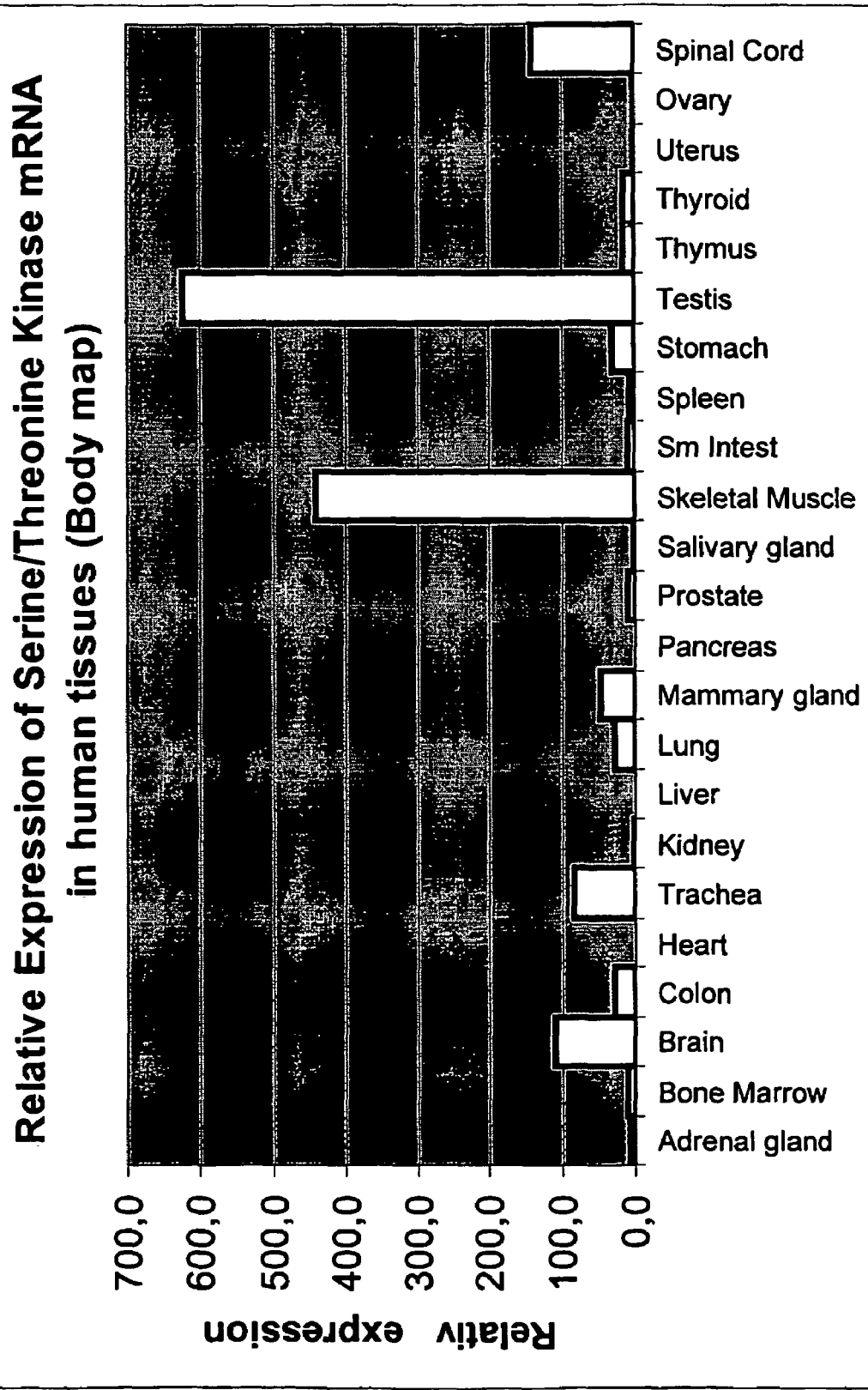
FIG. 22 shows the human serine/threonine kinase relative mRNA expression in human tissues (Body map).

For obesity and diabetes tissues, relative expression was determined as follows. Ct values were normalized to 18S RNA values. The highest expressing tissue was then assigned a value of 100. Expression levels for the remaining tissues were then expressed as percentages of the highest expressing tissue ([$\Delta C_T$ of tissue x/$\Delta C_T$ of highest expresser]×100). Results are shown in FIG. 21.

REFERENCES

1. Bossemeyer et al. (1993) Phosphotransferase and substrate binding mechanism of the cAMP-dependent protein kinase catalytic subunit from porcine heart as deduced from the 2.0 A structure of the complex with Mn2+ adenylylimidodiphosphate and inhibitor peptide PKI (5–24). *EMBO J.* 12(3):849–59.

2. Hanks and Hunter (1995) Protein kinases 6. The eukaryotic protein kinase superfamily: kinase (catalytic) domain structure and classification.) *FASEB J.* 9(8):576–96.

3. Johnson et al. (1998) The structural basis for substrate recognition and control by protein kinases. *FEBS Lett.* 430(1–2): 1–11.

4. Wang et al. (2001) Isolation and characterization of cDNAs for the protein kinase HIPK2(1). *Biochim Biophys Acta* 1518(1–2):168–72.

5. Kim et al. (1998) Homeodomain-interacting protein kinases, a novel family of co-repressors for homeodomain transcription factors. *J Biol Chem* 273(40):25875–9.

The invention claimed is:

1. An isolated and purified protein comprising a first polypeptide segment comprising an amino acid sequence shown in SEQ ID NO:6.

2. The protein of claim 1 further comprising a second polypeptide segment comprising an amino acid sequence which is not an amino acid sequence shown in SEQ ID NO:6, wherein the second polypeptide segment is joined to the first polypeptide segment by means of a peptide bond.

3. An isolated and purified polynucleotide which encodes an amino acid sequence shown in SEQ ID NO:6.

4. The polynucleotide of claim 3 which comprises a nucleotide sequence shown in SEQ ID NO:5.

5. The polynucleotide of claim 3 which is a cDNA.

6. An isolated single stranded polynucleotide sequence coding for SEQ ID NO:6, wherein the coding sequence comprises the nucleotide sequence shown in SEQ ID NO: 5.

7. An expression construct, comprising;
 a coding sequence for an amino acid sequence shown in SEQ ID NO:6; and
 a promoter which is located upstream from the coding sequence and which controls expression of the coding sequence.

8. The expression construct of claim 7 wherein the coding sequence comprises a nucleotide sequence shown in SEQ ID NO:5.

9. A host cell comprising an expression construct, wherein the expression construct comprises:
 a coding sequence for a protein comprising an amino acid sequence shown in SEQ ID NO:6; and
 a promoter which is located upstream from the coding sequence and which controls expression of the coding sequence.

10. The host cell of claim 9 which is prokaryotic.

11. The host cell of claim 9 which is eukaryotic.

12. A method of producing a protein, comprising the steps of:
 culturing a host cell in a culture medium, wherein the host cell comprises an expression construct comprising (a) a coding sequence for a protein comprising an amino acid sequence shown in SEQ ID NO:6 and (b) a promoter which is located upstream from the coding sequence and which controls expression of the coding sequence, wherein the step of culturing is carried out under conditions whereby the protein is expressed; and
 recovering the protein.

13. A composition comprising:
 a protein comprising an amino acid sequence shown in SEQ ID NO:6; and
 a pharmaceutically acceptable carrier.

14. A composition comprising:
 a polynucleotide encoding a protein comprising an amino acid sequence shown in SEQ ID NO:6; and
 a pharmaceutically acceptable carrier.

15. The composition of claim 14 wherein the polynucleotide comprises a nucleotide sequence shown in SEQ ID NO:5.

* * * * *